(12) United States Patent
Chen et al.

(10) Patent No.: US 12,186,755 B2
(45) Date of Patent: Jan. 7, 2025

(54) MULTI-WELL SEPARATION APPARATUS AND REAGENT DELIVERY DEVICE

(71) Applicant: DrugArray, Inc., La Jolla, CA (US)

(72) Inventors: Ning Chen, Richmond, CA (US); Robert Keith Shanahan, Carlsbad, CA (US); Dayu Teng, San Diego, CA (US); Daniel Joseph Braun, San Diego, CA (US)

(73) Assignee: DrugArray, Inc., La Jolla, CA (US)

( * ) Notice: Subject to any disclaimer, the term of this patent is extended or adjusted under 35 U.S.C. 154(b) by 379 days.

(21) Appl. No.: 17/334,544

(22) Filed: May 28, 2021

(65) Prior Publication Data

US 2021/0283598 A1    Sep. 16, 2021

Related U.S. Application Data

(62) Division of application No. 15/120,057, filed as application No. PCT/US2015/016435 on Feb. 18, 2015, now Pat. No. 11,090,654.

(Continued)

(51) Int. Cl.
*B01L 3/00* (2006.01)
*B01F 31/441* (2022.01)
(Continued)

(52) U.S. Cl.
CPC .......... *B01L 3/5085* (2013.01); *B01F 31/441* (2022.01); *B01F 31/85* (2022.01);
(Continued)

(58) Field of Classification Search
CPC ............. B01L 2200/028; B01L 3/5085; B01L 2300/0829
(Continued)

(56) References Cited

U.S. PATENT DOCUMENTS 3,883,398 A    5/1975    Ono
4,891,321 A    1/1990    Hubscher
(Continued)

FOREIGN PATENT DOCUMENTS

CN    1239905        12/1999
CN    101236203 A    8/2008
(Continued)

OTHER PUBLICATIONS

European Communication Pursuant to Article 94(3): EPC, mailed on Oct. 19, 2021, for European Patent Application No. 20154686.8, filed Jan. 30, 2020, 5 pages.

(Continued)

*Primary Examiner* — Natalia Levkovich
(74) *Attorney, Agent, or Firm* — Morrison & Foerster LLP

(57) ABSTRACT

Described herein are multi-well separation devices configured to allow a composition comprising a target agent to be separated into multiple wells, subdivided, recombined into a single well, and/or re-separated into the same or a different configuration of wells. Also described herein are reagent loading devices configured to simultaneously deliver one or more test agents to a plurality of volumes without having to individually deliver the test agents. Together, these devices allow high throughput parallel processes without repetitive pipetting or liquid handling robotics, though they may also be used separately. Also described herein are kits and systems for chemical or biological assays, as well as methods for using the multi-well separation devices and reagent loading devices described herein.

18 Claims, 27 Drawing Sheets

Related U.S. Application Data

(60) Provisional application No. 61/941,368, filed on Feb. 18, 2014.

(51) Int. Cl.
*B01F 31/85* (2022.01)
*G01N 33/50* (2006.01)
*B01F 101/23* (2022.01)

(52) U.S. Cl.
CPC .......... *B01L 3/527* (2013.01); *G01N 33/5008* (2013.01); *B01F 2101/23* (2022.01); *B01L 2200/025* (2013.01); *B01L 2200/028* (2013.01); *B01L 2200/0689* (2013.01); *B01L 2200/16* (2013.01); *B01L 2300/0609* (2013.01); *B01L 2300/0829* (2013.01); *B01L 2300/0851* (2013.01); *B01L 2400/0433* (2013.01); *G01N 2500/10* (2013.01)

(58) Field of Classification Search
USPC .................................................. 422/552, 553
See application file for complete search history.

(56) References Cited

U.S. PATENT DOCUMENTS

| | | | |
|---|---|---|---|
| 4,988,618 A | 1/1991 | Li | |
| 5,219,528 A * | 6/1993 | Clark | B01L 3/5025 422/527 |
| 5,882,930 A | 3/1999 | Baier | |
| 6,027,873 A | 2/2000 | Schellenberger | |
| 6,171,555 B1 | 1/2001 | Cargill | |
| 6,592,819 B1 | 7/2003 | Ogura | |
| 7,344,877 B1 | 3/2008 | Camacho | |
| 7,736,594 B1 | 6/2010 | Grudzien | |
| 11,090,654 B2 | 8/2021 | Chen et al. | |
| 2002/0094304 A1 | 7/2002 | Yang | |
| 2003/0166263 A1 | 9/2003 | Haushalter | |
| 2004/0037748 A1 | 2/2004 | Hasan | |
| 2004/0037750 A1 | 2/2004 | Stimpson | |
| 2004/0079580 A1 | 4/2004 | Manna | |
| 2004/0137605 A1 | 7/2004 | Mcgarry | |
| 2004/0226885 A1 | 11/2004 | Chen | |
| 2006/0078463 A1 | 4/2006 | Shea | |
| 2007/0280860 A1 | 12/2007 | Goodwin | |
| 2008/0286161 A1 | 11/2008 | Heaney | |
| 2010/0083778 A1 | 4/2010 | Bell | |
| 2010/0151511 A1 | 6/2010 | Greenizen | |
| 2017/0136456 A1 | 5/2017 | Chen | |

FOREIGN PATENT DOCUMENTS

| | | |
|---|---|---|
| CN | 101472940 A | 7/2009 |
| CN | 101506643 A | 8/2009 |
| CN | 101529246 | 9/2009 |
| CN | 102382765 A | 3/2012 |
| JP | 1201156 A2 | 8/1989 |
| JP | 2001099847 A2 | 4/2001 |
| JP | 2004340971 A | 12/2004 |
| JP | 2005509737 A | 4/2005 |
| JP | 2005536727 T2 | 12/2005 |
| JP | 2008200037 A | 9/2008 |
| WO | 199815356 A1 | 4/1998 |
| WO | 2003018854 A2 | 3/2003 |
| WO | 2003100421 A1 | 12/2003 |
| WO | 2004018104 A1 | 3/2004 |
| WO | 2005016532 A2 | 2/2005 |
| WO | 2005016532 A3 | 10/2005 |
| WO | 2008057111 A2 | 5/2008 |
| WO | 2009034927 A1 | 3/2009 |
| WO | 2008057111 A3 | 4/2009 |
| WO | 2011012859 A1 | 2/2011 |
| WO | 2015126979 A1 | 8/2015 |

OTHER PUBLICATIONS

European Examination Report mailed on Mar. 19, 2021, for European Application No. 20154686.8, filed on Jan. 30, 2020, 6 pages.
European Extended Search Report mailed on Sep. 29, 2017, for EP Application No. 15752342.4, filed on Sep. 8, 2016, fifteen pages.
Extended European Search Report, mailed on Jun. 16, 2020, for European Application No. 20154686.8, filed on Jan. 30, 2020, 13 pages.
International Preliminary Report on Patentability Sep. 1, 2016, for PCT Patent Application No. PCT/US2015/16435, Internationally filed on Feb. 18, 2015, eleven pages.
International Search Report mailed on Jul. 14, 2015, for PCT Patent Application No. PCT/US2015/16435, Internationally filed on Feb. 18, 2015, five pages.
Written Opinion mailed on Jul. 14, 2015, for PCT Patent Application No. PCT/US2015/16435, internationally filed on Feb. 18, 2015, twelve pages.

* cited by examiner

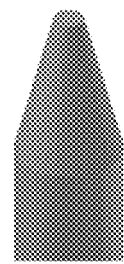
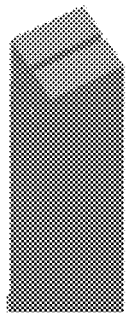
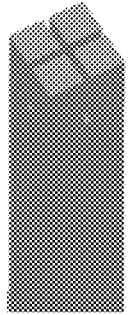
FIG. 12A  FIG. 12B  FIG. 12C
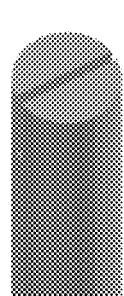
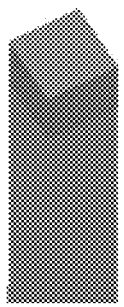
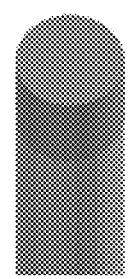
FIG. 12D  FIG. 12E  FIG. 12F
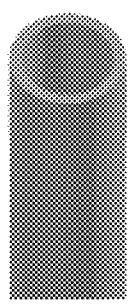
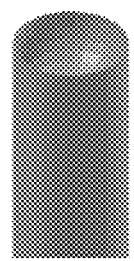
FIG. 12G  FIG. 12H

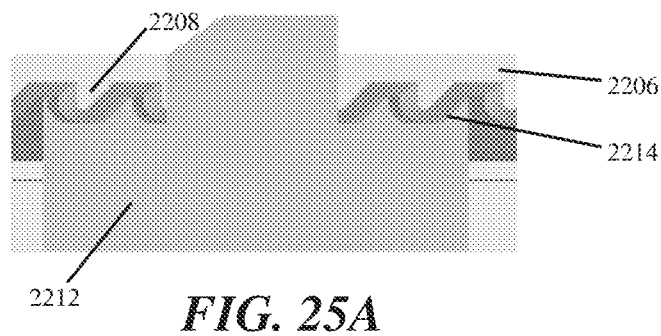
*FIG. 25A*
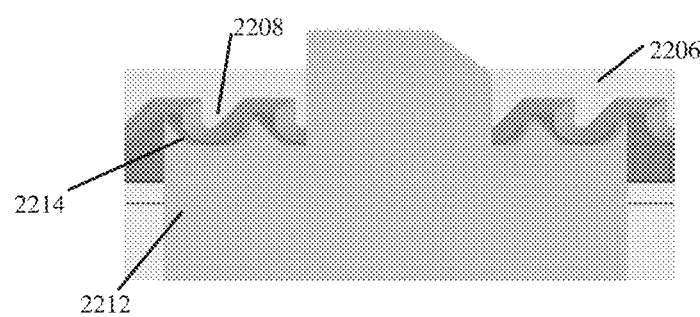
*FIG. 25B*
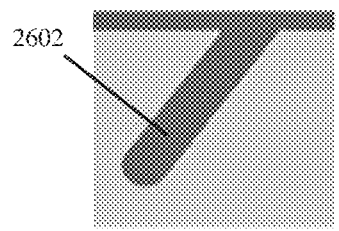 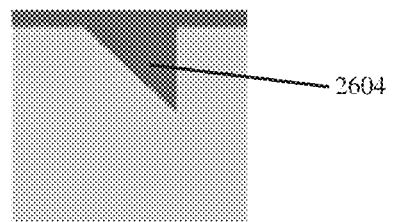
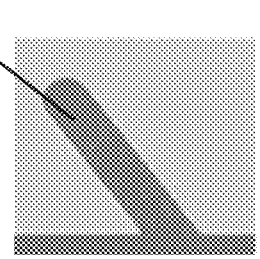 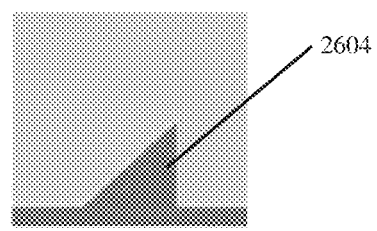
*FIG. 26A*  *FIG. 26B*

MULTI-WELL SEPARATION APPARATUS AND REAGENT DELIVERY DEVICE

CROSS-REFERENCE TO RELATED APPLICATIONS

This application is a divisional of U.S. application Ser. No. 15/120,057, filed Aug. 18, 2016, which is the U.S. National Phase application under 35 U.S.C. § 371 of International Application No. PCT/US2015/016435, filed internationally on Feb. 18, 2015, which claims priority benefit from Provisional Application No. 61/941,368, filed Feb. 18, 2014, the disclosures of which are hereby incorporated by reference in their entirety.

FIELD

Described herein are devices, kits, systems, and methods for efficiently and reversibly separating a composition comprising a target agent into a plurality of volumes without needing to individually separate the composition into each of the plurality of volumes, such that processes may be efficiently performed on each of the plurality of volumes, as well as on the composition as a whole. Also described herein are devices, kits, systems, and methods for efficiently delivering test agents to a plurality of volumes, without needing to individually deliver the test agents into each of the plurality of volumes.

BACKGROUND

High-throughput screening allows researchers to quickly conduct a large number of chemical, biological, or pharmacological tests in parallel and is an important aspect of biological and chemical research—for example, in the development of new drugs. Such screening can be conducted manually or performed in an automated fashion using robotics or liquid handling devices to manipulate the samples of interest. Multi-well plates, also known as microtiter or microwell plates, are generally used to hold the samples under evaluation. Such multi-well plates, which are usually disposable and made of plastic and/or glass, typically include a grid of small, open divots or wells. The desire to screen a large number of chemical or biological assays in parallel has resulted in the development of multi-well plates having large numbers of identical wells, such as 96, 384, 1536, or 3456 individual wells.

When performing screening operations, a target agent—for example, cells or chemical compounds—is often placed in each well of the multi-well plate being used. Different reagents or test agents may then also be added to various wells of the plate in order to screen for the effects of the reagents or test agents on the target agent. After all of the reaction components have been placed into the wells of a multi-well plate, and the necessary conditions for the reaction have been satisfied, the results of the reactions can be analyzed manually or by machine across all of the plate's wells.

Although robotic equipment exists for use in these processes, such equipment is generally expensive, and it can be slow if the pipette channels on the liquid handler are fewer than the number of wells to be transferred. The manual method, on the other hand, is slow, laborious, and prone to errors. Moreover, traditional methods for mixing reagents or test agents into the wells containing the target agents have limitations. Traditional mixing involves a shaker that shakes or vibrates the entire multi-well plate. For small volume wells, shaking or vibrating the entire multi-well plate does not create enough mixing in the individual wells; the higher the viscosity of the fluid and the smaller the well, the less effective the shaking or vibrating will be. The traditional alternative is to pipette a portion of the liquid in each individual well up and down, in and out of the wells, through the pipette tips. Using pipetting to mix the well contents creates large shear stresses at the bottom of the well, especially directly under the pipette opening. These fluidic shearing stresses may detach the target agent (e.g., cells), damage the target agent, or impose excess mechanical stimulation on the target agent, and the non-uniform shearing force and flow may induce non-uniform distribution of the target agent on the bottom surface of the wells. It is thus desirable have more efficient and accurate methods of manipulating target agents and test agents for screening and similar processes.

BRIEF SUMMARY

The multi-well separation devices described herein allow a composition comprising a target agent to be separated into multiple wells, to be subdivided, to be recombined into a single well, and/or to be re-separated into the same or a different configuration of wells. This is achieved by the devices having—unlike existing multi-well plates with fixed walls—separation wall structures that may be reversibly removed from a holding cavity containing the composition comprising the target agent. As such, the devices may allow for reversible and repeated separation and combination of volumes without needing to transfer the composition from one well to another via pipette or the like.

Also described herein are reagent loading devices configured to simultaneously deliver a test agent to each individual well of the multi-well separation devices. The reagent loading devices described herein allow one or more test agents to be simultaneously delivered to a plurality of volumes without having to individually deliver the one or more test agents to each of the plurality of volumes. This is achieved by the reagent loading devices having a plurality of protrusions, each comprising a stem and a closed tip suitable for holding a reagent. As such, the closed tips may each be loaded with a reagent, in a configuration corresponding to the desired delivery configuration to the plurality of volumes. The reagent loading devices may be configured to promote mixing of the reagents with the plurality of volumes, such as by being configured to vibrate, and may comprise a containment element or other design configured to protect the reagents loaded on the closed tips.

Together, these devices allow high throughput parallel processes without repetitive pipetting or liquid handling robotics. However, it should be appreciated that in some variations the multi-well separation devices described herein may be used separately from the reagent loading devices described here. Similarly, it should be appreciated that in some variations the reagent loading devices described herein may be used separately from the multi-well separation devices described herein. Also described herein are kits and systems for chemical or biological assays, as well as methods for using the multi-well separation devices and reagent loading devices described herein.

Generally, the multi-well separation devices described herein may comprise a substrate, and a removable separation well structure coupled to the substrate. In some of these variations, the separation well structure may comprise a plurality of walls defining a plurality of openings. In some of these variations, the substrate and the separation well structure may form a plurality of wells.

In some variations, the multi-well separation devices described herein may comprise a substrate, a boundary wall, and a removable separation well structure coupled to the substrate. In some of these variations, the separation well structure may comprise a plurality of walls defining a plurality of openings. In some of these variations, the substrate and the separation well structure may form a plurality of wells, and the boundary wall and the substrate may form a holding cavity.

In some variations, the multi-well separation devices described herein may comprise a substrate, a boundary wall, a boundary seal, and a removable separation well structure coupled to the substrate. In some of these variations, the separation well structure may comprise a plurality of walls defining a plurality of openings, the substrate and the separation well structure may form a plurality of wells, and the boundary seal may form a leak-proof seal with the boundary wall and the substrate to form a holding cavity.

In some variations, the multi-well separation devices described herein may comprise a substrate, a removable separation well structure coupled to the substrate, and a separation seal. In some of these variations, the separation well structure may comprise a plurality of walls defining a plurality of openings. In some of these variations, the separation seal may form a leak-proof seal between the substrate and the separation well structure to form a plurality of wells.

In some variations, the multi-well separation devices described here may comprise a substrate, a boundary wall, a boundary seal, a removable separation well structure coupled to the substrate, and a separation seal. In some of these variations, the separation well structure may comprise a plurality of walls defining a plurality of openings. In some of these variations, the separation seal may form a leak-proof seal between the substrate and the separation well structure to form a plurality of wells. In some of these variations, the boundary seal may form a leak-proof seal between the boundary wall and the substrate to form a holding cavity. In some of these variations, the boundary seal may be located between the substrate holder and the substrate.

In some variations, the multi-well separation devices described here may comprise a substrate, a removable separation well structure coupled to the substrate, and a concentrating well structure located between the substrate and the separation well structure. In some of these variations, the separation well structure may comprise a plurality of walls defining a plurality of openings. In some of these variations, the substrate and the separation well structure may form a plurality of wells. In some of these variations, the concentrating well structure may comprise a plurality of openings, and each of the plurality of openings of said concentrating well structure may correspond to one of the plurality of openings defined by the separation well structure. In some of these variations, each of the plurality of openings of said concentrating well structure may have a proximal cross-sectional area and a distal cross-sectional area, and the proximal cross-sectional area may be greater than the distal cross-sectional area.

In some of these variations, the separation well structure may be reversibly removably coupled to the substrate. In some of these variations, the plurality of walls may define at least about 96 openings. In some of these variations, the plurality of walls may define at least about 480 openings. In other variations, the plurality of walls may define at least about 6 openings, at least about 12 openings, at least about 24 openings, at least about 48 openings, at least about 384 openings, at least about 1536 openings, at least about 3456 openings, or more than 3456 openings. In some of these variations, the multi-well separation device may further comprise a boundary wall coupled to the substrate. In some of these variations, the substrate and the boundary wall may define at least one holding cavity. In some of these variations, the substrate and the boundary wall may further define at least two separated regions within the holding cavity. In some of these variations, the boundary wall may be removably coupled to the substrate. In some of these variations, the multi-well separation device may further comprise a substrate holder configured to couple the substrate to the boundary wall. In some of these variations, the substrate holder may comprise at least one clip, wherein the at least one clip may be configured to attach to a portion of the boundary wall. In some of these variations, the boundary wall may be reversibly removably coupled to the substrate. In some of these variations, the boundary wall may be fixedly coupled to the substrate. In some of these variations, the boundary wall may be integral to the substrate.

In some of these variations, the separation well structure may be coupled to the substrate via attachment to the boundary wall. In some of these variations, the separation well structure may comprise at least one clip, wherein the at least one clip may be configured to attach to a portion of the boundary wall. In some of these variations, the multi-well separation device may further comprise a second removable separation well structure coupled to the substrate. In some of these variations, the second separation well structure may comprise a second plurality of walls defining of second plurality of openings. In some of these variations, the substrate and the second separation well structure may form a second plurality of wells. In some of these variations, the second separation well structure may fit within one of the plurality of openings defined by the separation well structure. In some of these variations, the each of the second plurality of wells may have a smaller volume than each of the plurality of wells defined by the first separation well structure.

In some of these variations, the multi-well separation device may further comprise a concentrating well structure located between the separation well structure and the substrate. In some of these variations, the concentrating well structure may comprise a plurality of openings, wherein each of the plurality of openings of said concentrating well structure may correspond to one of the plurality of openings defined by the separation well structure. In some of these variations, each of the plurality of openings may have a proximal cross-sectional area and a distal cross-sectional area, and the proximal cross-sectional area may be greater than the distal cross-sectional area. In some of these variations, the distal cross-sectional area may be zero. In some of these variations, each of the plurality of openings defined by the separation well structure may have a first cross-sectional area, and each of the plurality of openings of the concentrating well structure may have a second cross-sectional area at a distal end, and the first cross-sectional area may be greater than the second cross-sectional area. In some of these variations, each of the plurality of openings of the concentrating well structure may contain a protein. In some of these variations, each of the plurality of openings of the concentrating well structure may contain a polymer. In some of these variations, each of the plurality of openings in the concentrating well structure may contain a hydrogel. In some of these variations, each of the plurality of openings in the concentrating well structure may contain a chemical coating.

In some of these variations, the concentrating well structure may be fixedly attached to the substrate. In some of these variations, the concentrating well structure may be fixedly attached to the boundary wall. In some of these variations, the multi-well separation device may further comprise a seal located between the boundary wall and the substrate. In some of these variations, the seal may be fixedly attached to the boundary wall. In some of these variations, the seal may be fixedly attached to the substrate. In some of these variations, the seal may comprise rubber. In some of these variations, the seal may comprise plastic. In some of these variations, the seal may comprise a polymer. In some of these variations, the multi-well separation device may further comprise a separation seal located between the separation well structure and the substrate. In some of these variations, the separation seal may be fixedly attached to the boundary wall. In some of these variations, the separation seal may be fixedly attached to the substrate. In some of these variations, the separation seal may be fixedly attached to the separation well structure. In some of these variations, the separation seal may comprise rubber. In some of these variations, the separation seal may comprise plastic. In some of these variations, the separation seal may comprise a polymer.

In some of these variations, each of the plurality of openings of the separation well structure may have a hexagonal cross-sectional shape. In some of these variations, each of the plurality of openings of the separation well structure may have a rectangular cross-sectional shape. In some of these variations, each of the plurality of openings of the separation well structure may have a circular cross-sectional shape. In some of these variations, the separation well structure may comprise rubber. In some of these variations, the separation well structure may comprise plastic. In some of these variations, the separation well structure may comprise silicon. In some of these variations, the separation well structure may comprise metal. In some of these variations, the separation well structure may comprise a polymer. In some of these variations, the separation well structure may comprise glass. In some of these variations, the separation well structure may comprise rubber. In some of these variations, each of the plurality of wells may have a volume of about 100 µL to 100 mL. In some of these variations, each of the plurality of wells may have a volume of less than about 100 µL, about 100 µL to about 200 µL, about 200 µL to about 400 µL, about 400 µL to about 600 µL, about 600 µL to about 800 µL, about 800 µL to about 1 mL, about 1 mL to about 10 mL, about 10 mL to about 20 mL, about 20 mL to about 40 mL, about 40 mL to about 60 mL, about 60 mL to about 80 mL, about 80 mL to about 100 mL, or more than about 100 mL. In some of these variations, each of the plurality of wells may have a depth of about 1 mm to about 40 mm. In some of these variations, each of the plurality of wells may have a depth of about 5 mm to about 15 mm, about 10 mm to about 20 mm, about 15 mm to about 25 mm, about 20 mm to about 30 mm, about 25 mm to about 35 mm, about 30 mm to about 40 mm, or more than about 40 mm.

In some of these variations, the substrate may be a planar structure. In some of these variations, the substrate may comprise glass. In some of these variations, the substrate may comprise plastic. In some of these variations, the substrate may comprise silicon. In some of these variations, the substrate may comprise ceramic. In some of these variations, the substrate may comprise metal. In some of these variations, the substrate may comprise a combination of one or more materials selected from the group consisting of glass, plastic, silicon, ceramic, and metal. In some of these variations, the substrate may be suitable for holding a target agent in a fixed position. In some of these variations, the substrate may be coated with a protein. In some of these variations, the substrate may be coated with a hydrogel. In some of these variations, the substrate may be coated with a polymer. In some of these variations, the substrate may be immobilized with chemical compounds. In some of these variations, the substrate may be immobilized with proteins. In some of these variations, the substrate may be immobilized with fixed cells. In some of these variations, the substrate may be immobilized with micro-organisms. In some of these variations, the substrate may be less than about 13 cm in a largest dimension. In some of these variations, the substrate may be about 11 cm to about 15 cm in a largest dimension, about 7.5 cm in a largest dimension, about 1 cm to about 30 cm in a largest dimension, about 5 cm to about 25 cm in a largest dimension, about 10 cm to about 20 cm in a largest dimension, or greater than about 30 cm in a largest dimension.

In some of these variations, the target agent may comprise a cell. In some of these variations, the target agent may comprise proteins. In some of these variations, the target agent may comprise chemical compounds. In some of these variations, the target agent may comprise a polymer. In some of these variations, the multi-well separation device may further comprise a cover. In some of these variations, the multi-well separation device may be configured for a single use.

Also described herein are kits for a chemical or biological assay. Generally, the kits for a chemical or biological assay may comprise a substrate and a separation well structure configured to reversibly and removably couple to the substrate. In some of these variations, the separation well structure may comprise a plurality of walls defining a plurality of openings. In some of these variations, the substrate and the separation well structure may be configured to form a plurality of wells when coupled. In some of these variations, the separation well structure may be configured to be reversibly and removably coupled to the substrate. In some of these variations, the plurality of walls may define at least about 96 openings. In some of these variations, the plurality of walls may define at least about 480 openings. In some of these variations, the plurality of walls may define at least about 6 openings, at least about 12 openings, at least about 24 openings, at least about 48 openings, at least about 384 openings, at least about 1536 openings, at least about 3456 openings, or more than 3456 openings.

In some of these variations, the kit for a chemical or biological assay may further comprise a boundary wall configured to be coupled to the substrate. In some of these variations, the substrate and the boundary wall may be configured to define at least one holding cavity when coupled. In some of these variations, the substrate and the boundary wall may be further configured to define at least two separated regions within the holding cavity when coupled. In some of these variations, the boundary wall may be configured to be removably coupled to the substrate.

In some of these variations, the kit for a chemical or biological assay may further comprise a substrate holder configured to couple the substrate to the boundary wall. In some of these variations, the substrate holder may comprise at least one clip, wherein the at least one clip may be configured to attach to a portion of the boundary wall. In some of these variations, the boundary wall may be configured to be reversibly and removably coupled to the substrate. In some of these variations, the boundary wall may be fixedly coupled to the substrate. In some of these variations, the boundary wall may be integral to the substrate. In some of these variations, the separation well structure may be configured to be coupled to the substrate via attachment to the boundary wall. In some of these variations, the separation well structure may comprise at least one clip, and the at least one clip may be configured to attach to a portion of the boundary wall.

In some of these variations, the kit for a chemical or biological assay may further comprise a second removable separation well structure coupled to the substrate, wherein the second separation well structure may comprise a second plurality of walls defining of second plurality of openings. In some of these variations, the substrate and the second separation well structure may be configured to form a second plurality of wells when coupled. In some of these variations, the second separation well structure may be configured to fit within one of the plurality of openings defined by the first separation well structure. In some of these variations, each of the second plurality of wells may have a smaller volume than each of the plurality of wells defined by the first separation well structure.

In some of these variations, the kit for a chemical or biological assay may further comprise a concentrating well structure configured to be located between the separation well structure and the substrate. In some of these variations, the concentrating well structure may comprise a plurality of openings, wherein each of the plurality of openings may correspond to one of the plurality of openings defined by the separation well structure. In some of these variations, each of the plurality of openings of said concentrating well structure may have a proximal cross-sectional area and a distal cross-sectional area, wherein the proximal cross-sectional area may be greater than the distal cross-sectional area. In some of these variations, the distal cross-sectional area may be zero. In some of these variations, each of the plurality of openings defined by the separation well structure may have a first cross-sectional area, and each of the plurality of openings of the concentrating well structure may have a second cross-sectional area at a distal end, wherein the first cross-sectional area may be greater than the second cross-sectional area. In some of these variations, each of the plurality of openings of the concentrating well structure may contain a protein. In some of these variations, the concentrating well structure may be fixedly attached to the substrate. In some of these variations, the concentrating well structure may be fixedly attached to the boundary wall.

In some of these variations, the kit for a chemical or biological assay may further comprise a seal configured to be located between the boundary wall and the substrate. In some of these variations, the seal may be fixedly attached to the boundary wall. In some of these variations, the seal may be fixedly attached to the substrate. In some of these variations, the seal may comprise rubber. In some of these variations, the seal may comprise plastic. In some of these variations, the seal may comprise a polymer. In some of these variations, the kit for a chemical or biological assay may further comprise a separation seal configured to be located between the separation well structure and the substrate. In some of these variations, the separation seal may be fixedly attached to the boundary wall. In some of these variations, the separation seal may be fixedly attached to the substrate. In some of these variations, the separation seal may be fixedly attached to the separation well structure. In some of these variations, the separation seal may comprise rubber. In some of these variations, the separation seal may comprise plastic. In some of these variations, the separation seal may comprise a polymer.

In some of these variations, each of the plurality of openings of the separation well structure may have a hexagonal cross-sectional shape. In some of these variations, each of the plurality of openings of the separation well structure may have a rectangular cross-sectional shape. In some of these variations, each of the plurality of openings of the separation well structure may have a circular cross-sectional shape. In some of these variations, the separation well structure may comprise rubber. In some of these variations, the separation well structure may comprise plastic. In some of these variations, the separation well structure may comprise silicon. In some of these variations, the separation well structure may comprise metal. In some of these variations, the separation well structure may comprise polymer. In some of these variations, the separation well structure may comprise glass. In some of these variations, the separation well structure may comprise rubber. In some of these variations, each of the plurality of wells may have a volume of about 100 µL to 100 mL. In some of these variations, each of the plurality of wells may have a volume of less than about 100 µL, about 100 µL to about 200 µL, about 200 µL to about 400 µL, about 400 µL to about 600 µL, about 600 µL to about 800 µL, about 800 µL to about 1 mL, about 1 mL to about 10 mL, about 10 mL to about 20 mL, about 20 mL to about 40 mL, about 40 mL to about 60 mL, about 60 mL to about 80 mL, about 80 mL to about 100 mL, or more than about 100 mL. In some of these variations, each of the plurality of wells may have a depth of about 1 mm to about 40 mm. In some of these variations, each of the plurality of wells may have a depth of about 5 mm to about 15 mm, about 10 mm to about 20 mm, about 15 mm to about 25 mm, about 20 mm to about 30 mm, about 25 mm to about 35 mm, about 30 mm to about 40 mm, or more than about 40 mm.

In some of these variations, the substrate may be a planar structure. In some of these variations, the substrate may comprise glass. In some of these variations, the substrate may comprise plastic. In some of these variations, the substrate may comprise silicon. In some of these variations, the substrate may comprise ceramic. In some of these variations, the substrate may comprise metal. In some of these variations, the substrate may comprise a combination of one or more materials selected from the group consisting of glass, plastic, silicon, ceramic, and metal. In some of these variations, the substrate may be suitable for holding a target agent in a fixed position. In some of these variations, the substrate may be coated with a protein. In some of these variations, the substrate may be coated with a hydrogel. In some of these variations, the substrate may be coated with a polymer. In some of these variations, the substrate may be immobilized with chemical compounds. In some of these variations, the substrate may be immobilized with proteins. In some of these variations, the substrate may be immobilized with fixed cells. In some of these variations, the substrate may be immobilized with micro-organisms. In some of these variations, the substrate may be less than about 13 cm in a largest dimension. In some of these variations, the substrate may be about 11 cm to about 15 cm in a largest dimension, about 7.5 cm in a largest dimension, about 1 cm to about 30 cm in a largest dimension, about 5 cm to about 25 cm in a largest dimension, about 10 cm to about 20 cm in a largest dimension, or greater than about 30 cm in a largest dimension.

In some of these variations, the target agent may comprise a cell. In some of these variations, the target agent may comprise proteins. In some of these variations, the target agent may comprise chemical compounds. In some of these variations, the target agent may comprise a polymer. In some of these variations, the kit for a chemical or biological assay may further comprise a cover. In some of these variations, the kit for a chemical or biological assay may be configured for a single use.

Also described herein are systems for a chemical or biological assay. Generally, the systems for a chemical or biological assay may comprise a reagent loading device and a separation device. In some variations, the separation device may be any of the multi-well separation devices described herein. In some variations, the reagent loading device may be any of the reagent loading devices described herein. In some variations, the reagent loading device may comprise a plurality of protrusions, wherein each protrusion may comprise a stem and a closed tip suitable for holding a reagent. In some of these variations, each of the plurality of protrusions may be configured to fit within one of the plurality of wells of any of the multi-well separation devices described herein.

Also described herein are methods for performing a chemical or biological assay. Generally, the methods for performing a chemical or biological assay may comprise applying a target agent to a substrate, coupling a first separation well structure to the substrate, wherein the separation well structure may comprise a plurality of walls defining a plurality of openings, and the substrate and the first separation well structure may form a first plurality of wells, thereby dividing the target agent into a first plurality of subpopulations, and applying a first plurality of test agents to the first plurality of subpopulations, wherein the effects of the first plurality of test agents on the target agent may be analyzed.

In some variations, the methods for performing a chemical or biological assay may comprise applying a cell suspension comprising cells to a substrate, coupling a separation well structure to the substrate, wherein the separation well structure may comprise a plurality of walls defining a plurality of openings, and the substrate and the separation well structure may form a plurality of wells, thereby dividing the cells into a plurality of subpopulations, and applying a plurality of drugs to the plurality of subpopulations, and wherein the effects of the plurality of drugs on the cells may be analyzed.

In some variations, the methods for performing a chemical or biological assay may comprise applying a cell suspension comprising cells to a substrate, coupling a separation well structure to the substrate, wherein the separation well structure may comprise a plurality of walls defining a plurality of openings, and the substrate and the separation well structure may form a plurality of wells, thereby dividing the cells into a plurality of subpopulations, and simultaneously applying a plurality of drugs to the plurality of subpopulations using a reagent loading device comprising a plurality of protrusions, wherein the effects of the plurality of drugs on the cells may be analyzed.

In some variations, the methods for performing a chemical or biological assay may comprise applying a hydrogel comprising cells to a substrate, coupling a separation well structure to the substrate, wherein the separation well structure may comprise a plurality of walls defining a plurality of openings, and the substrate and the separation well structure may form a plurality of wells, thereby dividing the hydrogel and dividing the cells into a plurality of subpopulations, and applying a plurality of drugs to the plurality of subpopulations, wherein the effects of the plurality of drugs on the cells may be analyzed.

In some variations, the methods for performing a chemical or biological assay may comprise applying a hydrogel comprising cells to a substrate, coupling a separation well structure to the substrate, wherein the separation well structure may comprise a plurality of walls defining a plurality of openings, and the substrate and the separation well structure may form a plurality of wells, thereby dividing the hydrogel and dividing the cells into a plurality of subpopulations, and simultaneously applying a plurality of drugs to the plurality of subpopulations, wherein the effects of the plurality of drugs on the cells may be analyzed.

In some variations, the methods for performing a chemical or biological assay may comprise applying a cell suspension comprising cells to a substrate, coupling a separation well structure to the substrate, wherein the separation well structure may comprise a plurality of walls defining a plurality of openings, and the substrate and the separation well structure may form a plurality of wells, thereby dividing the cells into a plurality of subpopulations, uncoupling the separation well structure from the substrate, applying a drug to the substrate, recoupling the separation well structure to the substrate, thereby re-dividing the cells into the plurality of subpopulations, applying a plurality of primary antibodies to the plurality of subpopulations, and applying a plurality of secondary antibodies to the plurality of subpopulations.

In some variations, the methods for performing a chemical or biological assay may comprise applying a cell suspension comprising cells to a substrate, coupling a separation well structure to the substrate, wherein the separation well structure may comprise a plurality of walls defining a plurality of openings, and the substrate and the separation well structure may form a plurality of wells, thereby dividing the cells into a plurality of subpopulations, uncoupling the separation well structure from the substrate, applying a drug to the substrate, recoupling the separation well structure to the substrate, thereby re-dividing the cells into the plurality of subpopulations, applying a plurality of primary antibodies to the plurality of subpopulations, uncoupling the separation well structure from the substrate, and applying secondary antibodies to the substrate.

In some variations, the methods for performing a chemical or biological assay may comprise applying a cell suspension comprising cells to a substrate, coupling a separation well structure to the substrate, wherein the separation well structure may comprise a plurality of walls defining a plurality of openings, and the substrate and the separation well structure may form a plurality of wells, thereby dividing the cells into a plurality of subpopulations, applying a plurality of drugs to the plurality of subpopulations, applying a plurality of primary antibodies to the plurality of subpopulations, uncoupling the separation well structure from the substrate, and applying secondary antibodies to the substrate.

In some variations, the methods for performing a chemical or biological assay may comprise applying a cell suspension comprising cells to a substrate, coupling a separation well structure to the substrate, wherein the separation well structure may comprise a plurality of walls defining a plurality of openings, and the substrate and the separation well structure may form a plurality of wells, thereby dividing the cells into a plurality of subpopulations, uncoupling the separation well structure from the substrate, applying a drug to the substrate, recoupling the separation well structure to the substrate, thereby re-dividing the cells into the plurality of subpopulations, simultaneously applying a plurality of primary antibodies to the plurality of subpopulations using a reagent loading device comprising a plurality of protrusions, and simultaneously applying a plurality of secondary antibodies to the plurality of subpopulations using a reagent loading device comprising a plurality of protrusions.

In some variations, the methods for performing a chemical or biological assay may comprise applying a composition comprising a drug to a substrate, coupling a separation well structure to the substrate, wherein the separation well structure may comprise a plurality of walls defining a plurality of openings, and the substrate and the separation well structure may form a plurality of wells, thereby dividing the composition into a plurality of subpopulations, and applying one of a library of cells to each of the plurality of wells, wherein the effects of the drug on the cell types may be analyzed.

In some variations, the methods for performing a chemical or biological assay may comprise applying a composition comprising a drug to a substrate, coupling a separation well structure to the substrate, wherein the separation well structure may comprise a plurality of walls defining a plurality of openings, and the substrate and the separation well structure may form a plurality of wells, thereby dividing the composition into a plurality of subpopulations, and simultaneously applying one of a library of cells to each of the plurality of wells using a reagent loading device comprising a plurality of protrusions, and wherein the effects of the drug on the cell types may be analyzed.

In some of these variations, the method for performing a chemical or biological assay may further comprise removing the first separation well structure from the substrate. In some of these variations, the method for performing a chemical or biological assay may further comprise treating the target agent with a universal reagent. In some of these variations, the method for performing a chemical or biological assay may further comprise recoupling the first separation well structure to the substrate. In some of these variations, the method for performing a chemical or biological assay may further comprise coupling a second separation well structure to the substrate, wherein the second separation well structure may comprise a plurality of walls defining a plurality of openings, and wherein the substrate and the second separation well structure may form a second plurality of wells, thereby dividing the target agent into a second plurality of subpopulations, wherein the second plurality of subpopulations may be different from the first plurality of subpopulations; and applying a second plurality of test agents to the second plurality of subpopulations. In some of these variations, the method for performing a chemical or biological assay may further comprise coupling a second separation well structure to the substrate, wherein the second separation well structure may comprise a plurality of walls defining a plurality of openings, wherein the second separation well structure may be configured to fit within one of the plurality of openings defined by the first separation well structure. In some of these variations, the method for performing a chemical or biological assay may further comprise removing the second separation well structure from the substrate. In some of these variations, the method for performing a chemical or biological assay may further comprise recoupling the second separation well structure to the substrate. In some of these variations, the method for performing a chemical or biological assay may comprise reversibly coupling the substrate to the separation well structure to form a plurality of wells.

In some of these variations, the first plurality of subpopulations may comprise at least a first subpopulation and a second subpopulation, and a first test agent may be applied to the first subpopulation and a second test agent may be applied to the second subpopulation. In some of these variations, the first plurality of test agents may be applied via a reagent loading device comprising a plurality of protrusions, wherein each protrusion may comprise a stem and a closed tip suitable for holding a reagent. In some of these variations, each of the plurality of protrusions may be configured to fit within one of the first plurality of wells. In some of these variations, the method for performing a chemical or biological assay may further comprise loading the reagent loading device with the first plurality of test agents. In some of these variations, the reagent loading device may be pre-loaded with the first plurality of test agents.

Independent from the multi-well separation devices described above, the present invention in another aspect provides reagent loading devices. In some variations, the multi-well separation devices described here and the reagent loading devices described here may be used or configured to be used together. In other variations, the multi-well separation devices described here may be used or configured to be used independently of the reagent loading devices. In yet other variations, the reagent loading devices may be used or configured to be used independently of the multi-well separation devices.

Generally, the reagent loading devices may comprise a plurality of protrusions. In some variations, each protrusion may comprise a stem and a closed tip suitable for holding a reagent. In some of these variations, each closed tip may be loaded with a reagent. In some of these variations, at least two of the closed tips may be loaded with different reagents. In some of these variations, each of the closed tips may be loaded with a different reagent. In some of these variations, the plurality of protrusions may be configured to vibrate. In some variations, the reagent loading device may comprise a plate to which the plurality of protrusions may be attached.

In some of these variations, the plurality of protrusions may comprise plastic. In some of these variations, the plurality of protrusions may comprise silicon. In some of these variations, the plurality of protrusions may comprise metal. In some of these variations, the plurality of protrusions may comprise polymer. In some of these variations, each of the plurality of protrusions may be at least about 1 mm long. In some of these variations, each of the plurality of protrusions may be at least about 5 mm long. In some of these variations, each of the plurality of protrusions may be at east about 1 cm long. In some of these variations, the length of the protrusions may be about 1 mm to about 2 mm, about 2 mm to about 4 mm, about 4 mm to about 6 mm, about 6 mm to about 8 mm, about 8 mm to about 1 cm, about 1 cm to about 2 cm, about 2 cm to about 4 cm, about 4 cm to about 6 cm, or longer than 6 cm. In some of these variations, the largest cross-sectional dimension of the tip may be about 100 microns. In some of these variations, the largest cross-sectional dimension of the protrusions may be about 1 µm to about 10 µm, about 10 µm to about 100 µm, about 100 µm to about 1 mm, about 1 mm to about 5 mm, about 5 mm to about 1 cm, about 1 cm to about 2 cm, or larger than about 2 cm.

In some of these variations, the closed tip may have a square cross-section. In some of these variations, the closed tip may have a circular cross-section. In some of these variations, the closed tip may have a pointed shape. In some of these variations, the closed tip may comprise a depression. In some of these variations, the depression may be linear. In some of these variations, the closed tip may comprise two intersecting linear depressions. In some of these variations, the depression may be hemispherical. In some of these variations, the depression may be cylindrical. In some of these variations, the tip may comprise a hydrogel or a sol-gel. In some of these variations, the tip may comprise a polymer. In some of these variations, the tip may comprise a plastic. In some of these variations, the tip may be substantially smooth. In some of these variations, the tip may comprise surface irregularities. In some of these variations, the tip may be dissolvable. In some of these variations, the plurality of protrusions may be configured to vibrate. In some of these variations, each of the plurality of protrusions may be coupled to a motor. In some of these variations, the plurality of protrusions may be coupled to a motor. In some of these variations, each of the plurality of pins may be configured to emit ultrasonic frequency waves.

In some of these variations, the reagent loading device may further comprise a plate to which the plurality of protrusions may be attached. In some of these variations, the plate further may comprise an indicator configured to indicate the orientation of the reagent loading device. In some of these variations, the indicator may be further configured to provide a handle for manipulating the array, for example, a handle in an arrow shape.

In some of these variations, the closed tips of the plurality of protrusions may be protected by a containment element. In some of these variations, the containment element may comprise individual wells configured to isolate each protrusion. In some of these variations, each of the closed tips of the plurality of protrusions may be enclosed in one of a plurality of caps. In some of these variations, the reagent loading device may comprise legs that extend beyond the closed tip to protect the closed tip from resting on a surface. In some of these variations, each of the tips may be loaded with a reagent. In some of these variations, the reagent may be in a solid form. In some of these variations, the reagent may be in a pure liquid form. In some of these variations, the reagent may be in a gel form. In some of these variations, the reagent may be in a liquid solution. In some of these variations, each of the closed tips may be capable of being loaded with at least about 1 pL of liquid solution. In some of these variations, each of the closed tips may be capable of being loaded with at least about 1 nL of liquid solution. In some of these variations, each of the closed tips may be capable of being loaded with at least about 1 µL of liquid solution. In some of these variations, each of the closed tips may be capable of being loaded with about 1 pL to about 10 pL, about 10 pL to about 100 pL, about 100 pL to about 1 nL, about 1 nL to about 10 nL, about 10 nL to about 100 nL, about 100 nL to about 1 µL, about 1 µL to about 10 µL, or more than about 10 µL of liquid solution. In some of these variations, at least two of the closed tips may be pre-loaded with different reagents. In some of these variations, each of the closed tips may be pre-loaded with a different reagent. In some of these variations, the reagent may be selected from the group consisting of a protein, nucleic acid, or chemical compound. In some of these variations, the reagent may be selected from the group consisting of a cell, micro-organism, or plant.

Also described herein are kits for loading a reagent onto a reagent loading device. Generally, the kits for loading a reagent onto a reagent loading device may comprise a plurality of protrusions, wherein each of the plurality of protrusions may have a closed tip suitable for holding a reagent, a containment element, a chamber, and at least one cap. In some variations, the chamber may comprise a plurality of compartments.

Also described herein are methods of loading a liquid solution comprising a reagent to any of the reagent loading devices described above. Generally, the methods of loading a liquid solution may comprise dipping the reagent loading device in a chamber comprising the liquid solution, and lifting the reagent loading device up way from the chamber. In some variations, the chamber may comprise a plurality of compartments. In some of these variations, at least two of the plurality of compartments may contain different reagents. In some of these variations, each of the plurality of compartments may contain a different reagent. In some of these variations, the reagent may be selected from the group consisting of a protein, nucleic acid, or chemical compound. In some of these variations, the reagent may be selected from the group consisting of a cell, micro-organism, or plant. In some of these variations, the method of loading a liquid solution may further comprise loading the chamber with the liquid solution. In some of these variations, the method of loading a liquid solution may further comprise applying a defined volume of the liquid solution to the closed tip of the each of the plurality of protrusions. In some of these variations, at least two of the plurality of protrusions may be loaded with liquid solution comprising a different reagent. In some of these variations, each of the plurality of protrusions may be loaded with liquid solution comprising a different reagent.

Also described herein are methods of loading one or more reagents to a plurality of isolated areas on a substrate. Generally, the methods of loading one or more reagents may comprise contacting each of the plurality of isolated areas with one of a plurality of closed tips, and removing the plurality of closed tips from the plurality of isolated areas. In some variations, the plurality of closed tips may be arranged in an array. In some variations, each of the plurality of closed tips may be loaded with one of the one or more reagents. In some of these variations, the plurality of isolated areas may comprise a plurality of spots. In some of these variations, the plurality of isolated areas may comprise a plurality of wells. In some of these variations, each of the plurality of isolated areas may contain a target agent. In some of these variations, at least two of the plurality of closed tips may be loaded with a different reagent. In some of these variations, each of the plurality of closed tips may be loaded with a different reagent. In some of these variations, each of the isolated areas may contain a liquid, and the method of loading one or more reagents may further comprise mixing the liquid in each of the plurality of isolated areas with the plurality of protrusions. In some of these variations, the mixing may comprise agitation. In some of these variations, the mixing may comprise sonication. In some of these variations, the method of loading one or more reagents may further comprise discarding the reagent loading device after removing the plurality of protrusions from the plurality of isolated areas. In some of these variations, the reagent loading device may be manipulated by a robotic device. In some of these variations, the substrate may be manipulated by a robotic device.

Also described herein are kits for loading reagents comprising a reagent loading device comprising a plurality of protrusions and a plate to which the plurality of protrusions are attached, wherein each protrusion comprises a stem and a closed tip suitable for holding a reagent; and an antibody library. In some variations, the antibody library may be pre-loaded onto the reagent loading device. In some variations, the kit further comprises an adaptor, wherein the adaptor corresponds to the reagent loading device and is configured to fit around a multi-well plate. In some of these variations, the adaptor may comprise a key corresponding to a notch of the reagent loading device. In some of these variations, the adaptor may resist vibration of the reagent loading device when the reagent loading device is partially loaded into the multi-well plate, but may allow vibration of the reagent loading device when the reagent loading device is fully loaded into the multi-well plate.

BRIEF DESCRIPTION OF THE DRAWINGS

FIGS. 12A-12H are perspective views of closed tips of protrusions of a reagent delivery device.

FIGS. 25A-25B are close-up top views of a portion of the reagent loading device and adaptor of FIG. 22, where the reagent loading device is properly (FIG. 25A) and improperly (FIG. 25B) oriented.

FIGS. 26A-26B show example orientation keys of an adaptor.

DETAILED DESCRIPTION

The multi-well separation devices described herein allow a composition comprising a target agent to be separated into multiple wells, to be subdivided, to be recombined into a single well, and/or to be re-separated into the same or a different configuration of wells. This is achieved by the devices having-unlike existing multi-well plates with fixed walls-separation wall structures that may be reversibly removed from a holding cavity containing the composition comprising the target agent. As such, the devices may allow for reversible and repeated separation and combination of volumes without needing to transfer the composition from one well to another via pipette or the like.

The reagent loading devices described herein allow one or more test agents to be simultaneously delivered to a plurality of volumes without having to individually deliver the one or more test agents to each of the plurality of volumes. This is achieved by the reagent loading devices having a plurality of protrusions, each comprising a stem and a closed tip suitable for holding a reagent. As such, the closed tips may each be loaded with a reagent, in a configuration corresponding to the desired delivery configuration to the plurality of volumes. The reagent loading devices may be configured to promote mixing of the reagents with the plurality of volumes, such as by being configured to vibrate, and may comprise a containment element configured to protect the reagents loaded on the closed tips.

The reagent loading devices may be configured to simultaneously deliver a test agent to each individual well of the multi-well separation devices. Together, these devices allow high throughput parallel processes without repetitive pipetting or liquid handling robotics. However, it should also be appreciated that the devices may be used separately. Also described herein are kits and systems for chemical or biological assays, as well as methods for using the multi-well separation devices and reagent loading devices described herein.

Multi-Well Separation Device

Figure 1A:
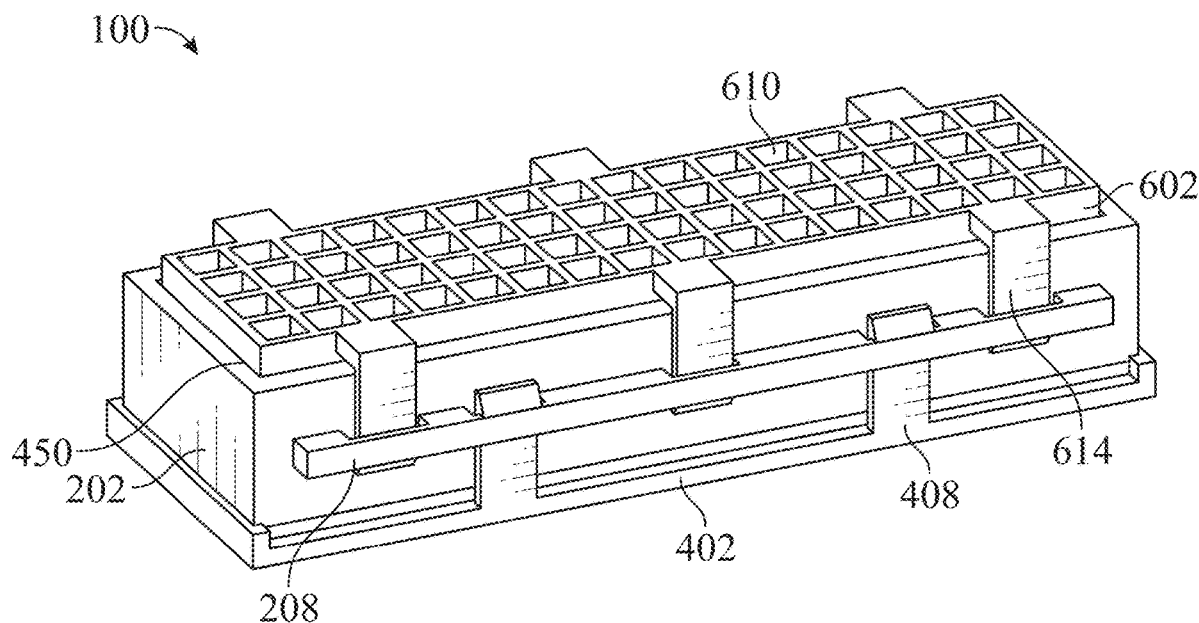
FIG. 1A is a perspective view of one embodiment of an assembled multi-well separation device.
Figure 1B:
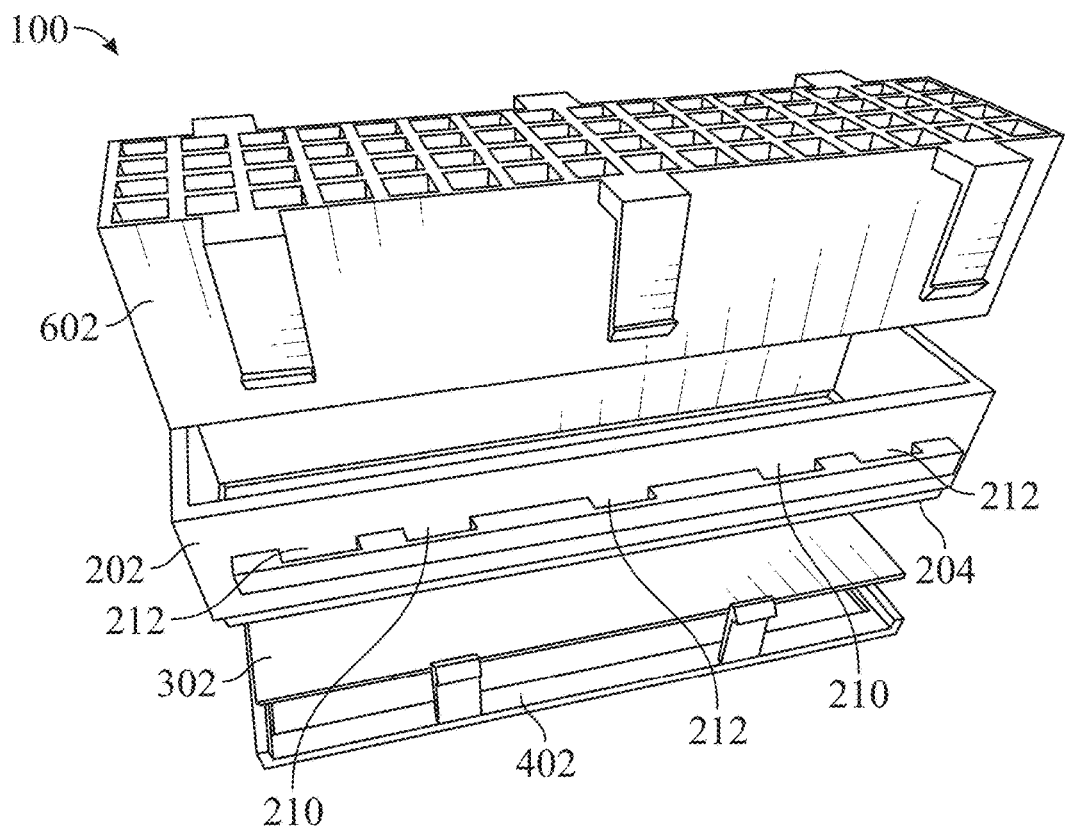
FIG. 1B is an exploded perspective view of a multi-well separation device.

FIG. 1A illustrates a perspective view of one embodiment of the assembled multi-well separation device 100. FIG. 1B illustrates an exploded perspective view of the multi-well separation device 100. In general, the multi-well separation device 100 may comprise a holding cavity 450 and a removable separation well structure 602 that may fit within the holding cavity 450. A composition (e.g., a cell suspension) in the holding cavity 450 may be reversibly separated into different wells by placement of the separation well structure 602 within the holding cavity 450, as described in more detail below. In general, the holding cavity 450 may be formed by a boundary wall 202 and a substrate 302, which may in some variations be coupled together to form the holding cavity 450 by a substrate holder 402, or in other variations may be fixedly attached or integral to each other. Each of these elements will be described in more detail below.

Boundary Wall

The boundary wall 202 may form the lateral portions of the holding cavity 450. In the variation shown in FIGS. 2A and 2B, the boundary wall 202 may comprise four orthogonal portions-a first portion 202a, a second portion 202b, a third portion 202c, and a fourth portion 202d. These four portions may define a rectangular region. In some variations, the four orthogonal portions may be one integrated component, while in other variations, the four orthogonal portions may comprise more than one component (e.g., two, three, four, or more), which may be attached in any suitable manner (e.g. using adhesives (glues, adhesive polymers, and the like), welding, mechanical fasteners, chemical bonding, a combination of these methods, or the like).

It should be appreciated, however, that the boundary wall 202 need not define a rectangular region, and furthermore, it need not comprise four portions. In some variations, for example, the boundary wall 202 may define any polygon (e.g. a triangle, quadrilateral (e.g. parallelogram, trapezoid), pentagon, hexagon, etc.). It should be appreciated that the boundary wall 202 need not be substantially planar and may be curved to define a region having a curved shape (e.g. a circle, ellipse, oval, annulus, circular segment, etc.). In some variations, the boundary wall 202 may comprise fewer than four portions (e.g., one, two, or three portions) or more than four portions (e.g., five, six, seven, eight, or more portions). The boundary wall 202 may also define more than one region. For example, in some variations the boundary wall 202 may comprise a fifth portion, which may be attached to opposite portions of the boundary wall (e.g., on a first end to the first portion 202a and on a second end to the third portion 202c). In such variations, the boundary wall 202 may define two rectangular regions.

Substrate

The substrate 302 may form the bottom of the holding cavity 450. The substrate 302 may thus serve as base for a composition (e.g., a cell suspension) placed within the holding cavity 450. In cases in which the composition placed within the holding cavity 450 comprises target agents in a fluid, such as cells, the substrate 302 may serve as a surface upon which the target agents may settle. The substrate 302 may be suitable for holding the target agents in a fixed position once settled onto the proximal surface 304 of the substrate 302, as described in more detail below. In some cases, the substrate 302 may be configured to allow the target agents to sit in a substantially uniform layer on substrate 302.

Figure 2A:
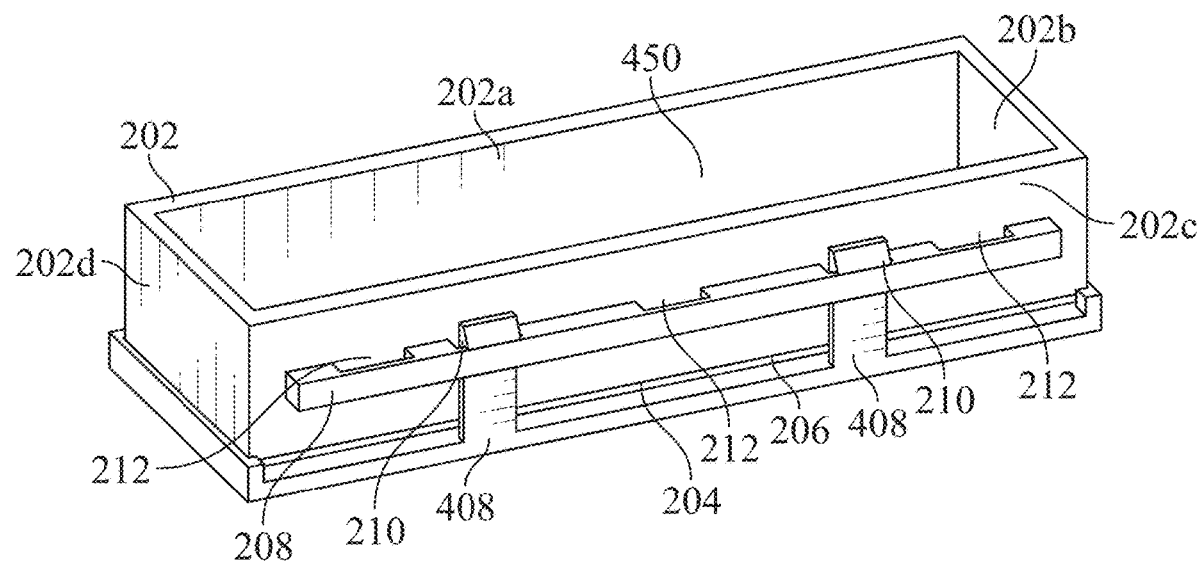
FIGS. 2A-2B are perspective views of a boundary wall, substrate, and substrate holder in coupled and uncoupled configurations, respectively.
Figure 3:
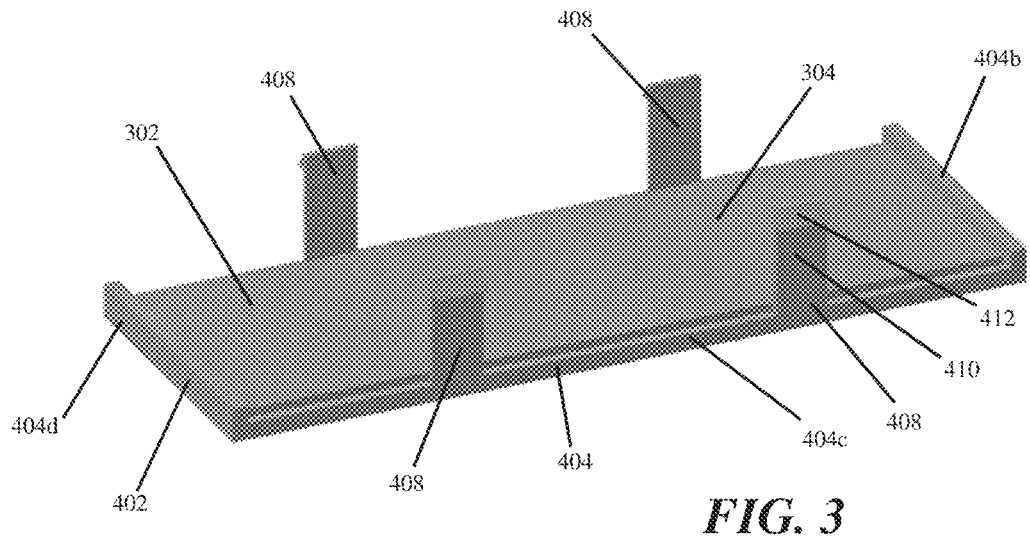
FIG. 3 is a perspective view of a substrate and substrate holder.

As shown in FIG. 3, the substrate 302 may comprise a substantially planar surface. The substrate may comprise any suitable material, such as but not limited to glass, plastic, silicon, ceramic, metal, combinations of these materials, or the like. In some variations, the substrate may comprise a suitable piece of commonly available laboratory equipment, such as but not limited to a glass slide or a cover slip. The substrate 302 may be sized to interface appropriately with the boundary wall 202. That is, the substrate 302 may have a cross-sectional shape about the same size as or larger than the cross-sectional shape of the boundary wall 202. In the variation shown in FIG. 3, the substrate 302 may comprise a substantially planar rectangle having the same cross-sectional shape as the boundary wall 202, such that the outer edges of the substrate 302 are flush with the outer surfaces of the boundary wall 202 (as shown in FIG. 2A).

In some variations, the substrate may comprise a coating on its proximal surface. For example, the substrate may comprise a coating such as but not limited to coatings comprising one or more chemical compounds, proteins, gels (e.g., a hydrogel), polymers, co-polymers, fixed cells, microorganisms, a conductive surface, or the like. As one example, the coating may comprise a gel comprising a growth medium (e.g., an agar gel). In some variations in which the coating comprises a gel, a liquid may be loaded into the holding cavity and subsequently cured to polymerize into a gel. In some variations in which the substrate comprises a coating, the coating may be covalently bonded through chemical cross-linkers. For instance, in variations in which the substrate comprises glass or silicon, the substrate may be covalently bonded with silane, which may in turn be bound to a coating comprising one or more chemical compounds, proteins, gels, or polymers. In some variations, a metal coating may be deposited by vaporization. In some variations, coating patterns may be created by microfabrication techniques, such as micro-printing and photo-lithography. In some variations, the coating may improve the suitability of the substrate for holding a target agent in a fixed position. In other variations, the coating may assist with detection, dielectrophoresis, migration studies, chemotaxis (with channels between wells). In some variations, the substrate may comprise microfluidics or electrodes.

Boundary Seal

The multi-well separation device 100 may further comprise a boundary seal 204. The boundary seal 204 may form a leak-proof seal between the boundary wall 202 and the substrate 302 when the boundary wall 202 and the substrate 302 are coupled (described in more detail below). The boundary seal 204 may comprise any suitable material for forming a seal, such as but not limited to rubber, plastic, or a polymer. The boundary seal 204 may comprise a thin strip of this material, having a shape corresponding to the distal side 206 of the boundary wall 202.

In some variations, the boundary seal 204 may be located between the boundary wall 202 and the substrate 302 when the boundary wall 202 and substrate 302 are coupled. In some of these variations, the boundary seal 204 may be fixed to the distal side 206 of the boundary wall 202. In these variations, the boundary seal 204 may be fixed to the distal side 206 in any suitable manner, such as but not limited to adhesives (glues, adhesive polymers, and the like), chemical bonding, or the like. In these variations, the fixation of the boundary seal 204 to the distal side 206 of the boundary wall 202 may create a leak-proof seal between the boundary seal 204 and the boundary wall 202, while the compressive force (described below) between the boundary wall 202 and the substrate 302 may press together the boundary seal 204 and the substrate 302, creating a leak-proof seal. In other variations, the boundary seal 202 may be fixed to the proximal surface 304 of the substrate 302, also in any suitable manner. In these variations, the fixation of the boundary seal 204 to the proximal surface 304 of the substrate 302 may create a leak-proof seal between the boundary seal 204 and the substrate 302, while the compressive force (described below) between the boundary wall 202 and the substrate 302 may press together the boundary seal 204 and the boundary wall 202, which may create a leak-proof seal. In yet other variations, the boundary seal 204 may not be fixed to either the boundary wall 202 or the substrate 302, but may instead be sandwiched between the boundary wall 202 and the substrate 302 by the compressive force when the boundary wall 202 and the substrate 302 are coupled (described in more detail below). In yet other variations in which the boundary wall 202 is fixedly attached to the substrate 302 (described in more detail below), the boundary seal 204 may be fixed to both the proximal surface 304 of the substrate 302 and the distal side 206 of the boundary wall 202.

Figure 21A:
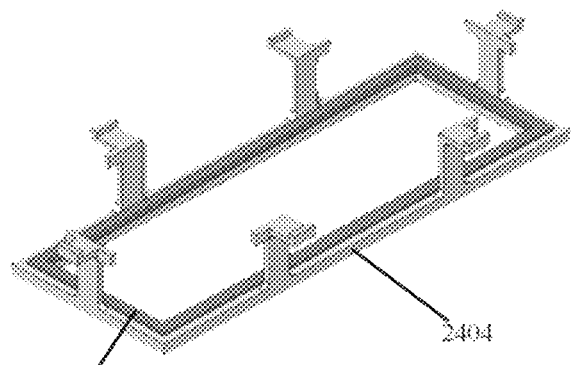
FIG. 21A is a perspective view of a substrate holder and boundary seal.
Figure 21B:
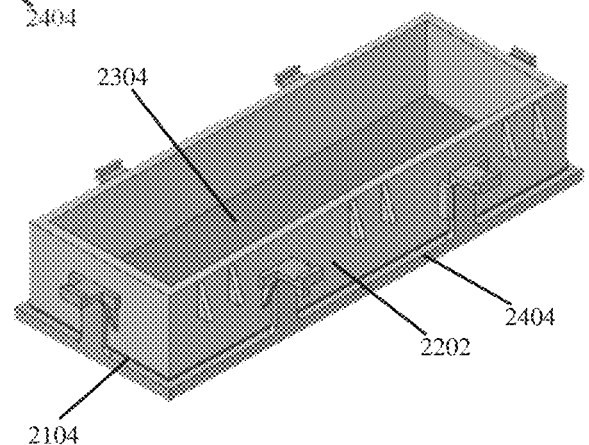
FIG. 21B is a perspective view of the substrate holder and boundary seal of FIG. 21A coupled with a boundary wall and substrate.
Figure 21C:
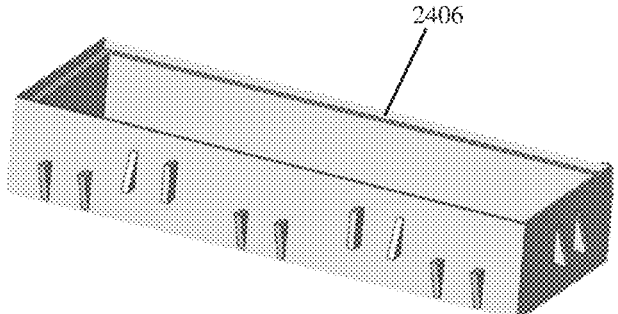
FIG. 21C is a bottom perspective view of the boundary wall of FIG. 21B alone.
Figure 21D:
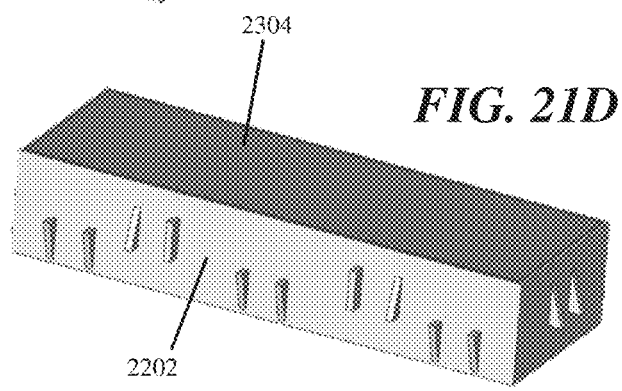
FIG. 21D is a bottom perspective view of the boundary wall and substrate of FIG. 21B.

In other variations, the boundary seal may be located between the substrate holder and the substrate. An example of such a variation is shown in FIG. 21A, where the boundary seal 2104 may be located on the proximal side of substrate holder 2404. In these variations, the boundary seal 2104 may be fixed to the proximal side of the substrate holder 2404 (e.g., by being pre-secured or casted), but need not be. In these variations in which the boundary seal 2104 is located on the proximal side of substrate holder 2404, the boundary wall 2202 and substrate 2304 may be placed on top of the boundary seal 2014, as shown in FIG. 21B. More specifically, the boundary wall 2202 (as shown from a bottom perspective view in FIG. 21C) may comprise a recessed region 2406 along the distal edge of each portion of the boundary wall 2202. The recessed region 2406 may be configured to hold substrate 2304, such that when substrate 2304 is placed within the recessed region 2406, the distal surface of the substrate 2304 and the distal surfaces of the boundary wall 2202 are level (as shown from a bottom perspective view in FIG. 21D). When the boundary wall 2202 and substrate 2304 are placed on the boundary seal 2104 and substrate holder 2404 as shown in FIG. 21B, the boundary seal 2104 may seal any space between the substrate 2304 and the boundary wall 2202 via the compressive force between the boundary wall and the substrate holder when they are coupled (as described in more detail below). In these variations, the location of the boundary seal between the substrate holder and the substrate (i.e., distal to the substrate), instead of between the substrate and the boundary wall, may contribute to a larger working area on the proximal surface of the substrate (i.e., the surface located in the suspension chamber).

It should be appreciated, however, that the multi-well separation devices described herein need not comprise a boundary seal. For example, a boundary seal may be unnecessary if the boundary wall and substrate are configured to form a holding cavity that can suitably hold a composition (e.g., a cell suspension) within it without leaking, without a boundary seal. For example, in variations in which the boundary wall is fixedly attached or integral to the substrate, the multi-well separation device may not comprise a boundary seal. As another example, in variations in which the boundary wall and substrate are not fixedly attached or integral but are configured to form a leak-proof seal, the multi-well separation device may not comprise a boundary seal. This may be the case, for instance, if the boundary wall comprises a material such as a rubber, plastic, or polymer that may be capable of forming a seal with the material of the substrate. In these cases, compressive force pressing together the boundary wall and the substrate may create a leak-proof seal directly between the boundary wall and the substrate. In yet other variations, a boundary seal may be unnecessary if the holding cavity is intended to hold a gel, solid, or the like, which may not require a tight seal to prevent leaking.

Substrate Holder

Figure 4A:
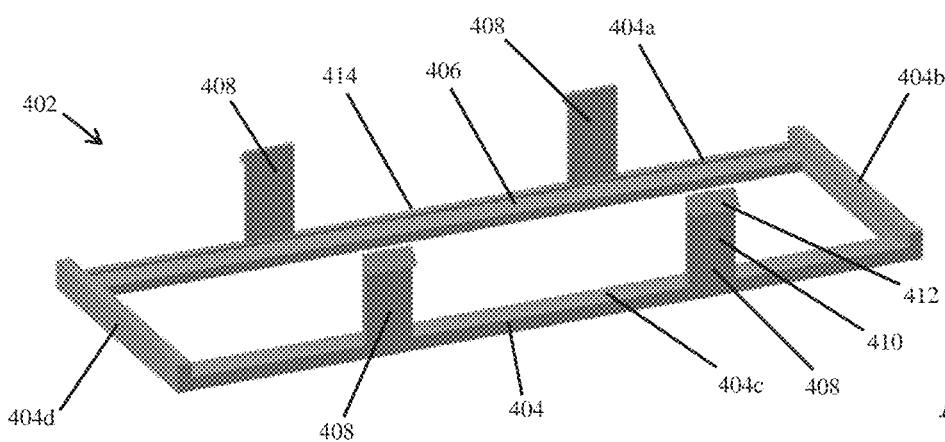
FIGS. 4A-4B are perspective and side views, respectively, of a substrate holder.

The substrate 302 may be coupled to the boundary wall 202 via a substrate holder 402, illustrated with the substrate 302 in FIG. 3 and alone in FIG. 4A. The substrate holder may also be configured to couple the separation well structure 602 to the boundary wall 202, as described in more detail below. The substrate holder 402 may have any design suitable for coupling the boundary wall 202 and the substrate 302. In some variations, the substrate holder 402 may reversibly couple the boundary wall 202 and the substrate 302; in other variations, the substrate holder 302 may irreversibly couple the boundary wall 202 and the substrate 302.

In order to couple the substrate 302 and the boundary wall 202, the substrate holder may comprise a first portion that is configured to exert a proximal force on the substrate 302, and a second portion that is configured to exert a distal force on the boundary wall 202, thus creating a compressive force pressing the boundary wall 202 and substrate 302 toward each other. In the embodiment shown in FIGS. 4A-4B, the substrate holder 402 may comprise a frame 404 that is configured to exert a proximal force on the substrate. The configuration of the frame 404 may be such that it corresponds to the configuration of the boundary wall 202; that is, the cross-sectional shape of the frame 404 may be substantially the same as the cross-sectional shape of the boundary wall 202, such that the substrate holder 402 may be coupled to the boundary wall 202. The frame 404 may comprise four orthogonal portions-a first portion 404a, a second portion 404b, a third portion 404c, and a fourth portion 404d. These four portions may define a rectangular region having the same cross-section as the rectangular region defined by the four portions of the boundary wall 202 described above. It should be appreciated that in order to correspond to the configuration of the boundary wall 202, the substrate holder 402 may have more or fewer portions (e.g. one, two, three, five, six, seven, eight, or more), which need not be orthogonal to each other, and which need not be straight and may be curved, as described above with respect to boundary wall 202.

The frame 404 may comprise a feature configured to interface with the substrate 302, which may help the substrate holder 402 to hold the substrate 302. As shown in FIG. 4A, in some variations this feature may comprise a recessed region 406 along each portion of the frame 404. The recessed region 406 may define a lip 414 around the outer edges of the frame. This lip 414 may help to hold the substrate 302 within the frame 404 by preventing lateral movement of the substrate 302 relative to the frame 404.

Figure 4B:
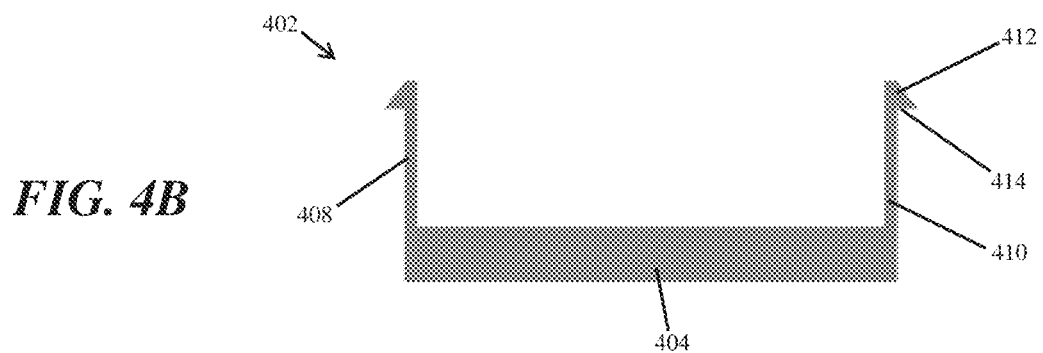

The second portion of the substrate holder 402, configured to exert a distal force on the boundary wall 202, may in some variations comprise boundary wall clips 408. The boundary wall clips 408 may be configured to couple the substrate holder 402 and the boundary wall 202 by interfacing with a portion of the boundary wall 202. In the variation shown in FIGS. 3 and 4A-4B, the boundary wall clips 408 may comprise an elongate portion 410 and a tab 412. The elongate portion 410 may extend proximally from the frame 404 and may have a substantially planar shape, while the tabs 412 may be located at the proximal end of the elongate portion 410 and may have an outwardly facing triangular shape, as shown in FIG. 4B.

Figure 2B:
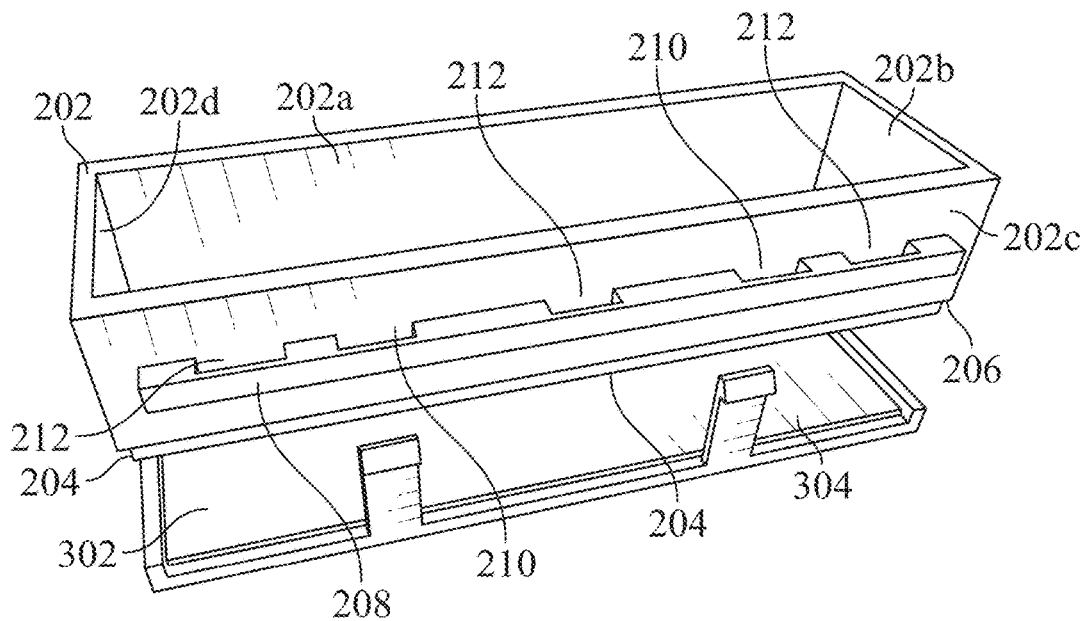

The boundary wall clips 408 may be configured to interface with a portion of the boundary wall 202. As shown in FIGS. 2A-2B, the boundary wall 202 may comprise two locking strips 208. The locking strips 208 may comprise both substrate holder locks 210 and separation well locks 212. The locking strips 208 may extend laterally from the outside surfaces of the first portion of the boundary wall 202a and from the third portion of the boundary wall 202c. In some variations, the locking strips may be integral to the boundary wall 202, or in other variations, they may be attached to the boundary wall 202 in any suitable manner. In the embodiment shown, the substrate holder locks 210 and separation well locks 212 may comprise openings formed between the boundary wall 202 and the locking strips 208 that are configured to interface with the substrate holder 402 and the separation well structure 602, respectively. More specifically, the elongate portions 410 of the boundary wall clips 408 may fit within the openings of the substrate holder locks 210 between the boundary wall 202 and the locking strips 208, while the tabs 412 of the boundary wall clips 408 may hook over the proximal surface of the locking strips 208, as shown in FIG. 2A. The interface between the distal surface 414 of the tabs 412 (see FIG. 4B) and the proximal surface of the locking strips 208 may resist distal motion of the substrate holder 402 relative to the boundary wall 202, which may thus couple together the boundary wall 202 and substrate holder 402. This may in turn sandwich the substrate 302 between the boundary wall 202 and the substrate holder 402, in addition to sandwiching the boundary seal 204 between the boundary wall 202 and the substrate 302, in those variations having a boundary seal 204.

While the tab 412 is shown as having a triangular shape, it should be appreciated that the tabs 412 may have other suitable shapes. Furthermore, while the variation shown in FIGS. 3 and 4A-4B comprises four boundary wall clips 408 (two each on opposite sides of boundary wall 202), it should be appreciated that the substrate holder 402 may have any suitable number of boundary wall clips 408 (e.g., one, two, three, four, five, six, seven, eight, or more), and the boundary wall 202 may have any suitable number of corresponding substrate holder locks 210. It should also be appreciated that the number of boundary wall clips 408 on the substrate holder 402 need not match the number of substrate holder locks 210 on the boundary wall 202, provided that the configuration is such that the substrate holder 402 may be coupled to the boundary wall 202. It should also be appreciated that the boundary wall clips 408 (and corresponding substrate holder locks 210 on the locking strip 208) may have different arrangements on the frame 404 of the substrate holder 402.

Figure 13:
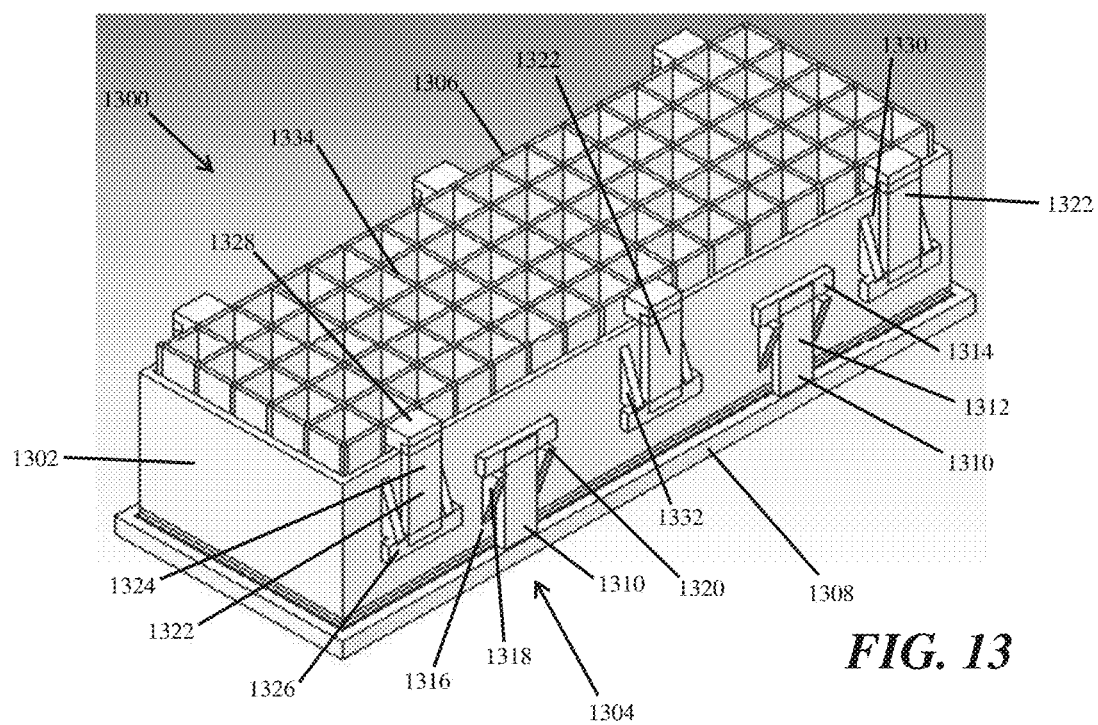
FIG. 13 is a perspective view of a multi-well separation device.

It should be appreciated that the substrate holder may have other designs. The design should be capable of generating a sufficient compressive force between the boundary wall and the substrate to create a leak-proof seal for the holding cavity. Another embodiment of a multi-well separation device 1300, having boundary wall 1302, substrate holder 1304, and separation well structure 1306, is shown in FIG. 13. Substrate holder 1304 may comprise a frame 1308 that is configured to exert a proximal force on the substrate. The configuration of frame 1308 may be such that it corresponds to the configuration of the boundary wall 1302; that is, the cross-sectional shape of the frame 1308 may be substantially the same as the cross-section shape of the boundary wall 1302 (which may have similar characteristics to boundary wall 202 of multi-well separation device 100, as described in detail above), such that the substrate holder 1304 may be coupled to the boundary wall 1302. The frame 1308 may have a similar design to frame 404 of multi-well separation device 100, as described in detail above, including its component portions and/or feature configured to interface with the substrate.

Like substrate holder 402 described above, substrate holder 1304 may comprise a portion configured to exert a distal force on the boundary wall 1302, which may in some variations comprise boundary wall clips 1310. The boundary wall clips 1310 may be configured to couple the substrate holder 1304 and the boundary wall 1302 by interfacing with a portion of the boundary wall 1302. In the variation shown in FIG. 13, the boundary wall clips 1310 may have a T-shape, comprising a vertical portion 1312 and a horizontal portion 1314. The vertical portion 1312 may extend proximally from the frame 1308 and may have a substantially planar shape. The horizontal portion 1314 may be located at the proximal end of the vertical portion 1314 and may have a substantially planar shape extending outwardly beyond the laterally edges of the vertical portion 1312.

The boundary wall clips 1310 may be configured to interface with a portion of the boundary wall 1302. The boundary wall 1302 may comprise substrate holder locks 1316 corresponding to each boundary wall clip 1310. As shown in FIG. 13, the substrate holder locks 1316 may each comprise two projections 1318. The two projections 1318 may have a triangular shape extending outwardly from the boundary wall 1302, with the triangular shape oriented such that the projection is at a minimum at the distal end of the projection and at a maximum at the proximal end of the projection. The two projections 1318 may be spaced apart by a distance that is greater than the width of the vertical portion 1312 of the boundary wall clips 1310, but less than the width of the horizontal portion 1314 of the boundary wall clips 1310. As such, the two projections 1318 may each form a proximal horizontal surface 1320 configured to interface with a distal horizontal surface of the horizontal portions 1314 of the boundary wall clips 1310. The interface between the proximal horizontal surfaces 1320 of the projections 1318 and the distal horizontal surfaces of the horizontal portions 1314 of the boundary wall clips 1310 may resist distal motion of the substrate holder 1304 relative to the boundary wall 1302, in addition to sandwiching a boundary seal between the boundary wall 1302 and a substrate, in those variations having a boundary seal, as described in more detail above with respect to multi-well separation device 100. The vertical portions 1312 of the boundary wall clips 1310 may be configured to be able to be flexed outwardly in order to allow the substrate holder 1304 to be attached to the boundary wall 1302, as described in more detail below.

While variation shown in FIG. 13 comprises four boundary wall clips 1310 (two each on opposite sides of boundary wall 1302), it should be appreciated that the substrate holder 1304 may have any suitable number of boundary wall clips 1301 (e.g. one, two, three, four, five, six, seven, eight, or more), and the boundary wall 1302 may have any suitable number of corresponding substrate holder locks 1316. It should also be appreciated that the number of boundary wall clips 1310 on the substrate holder 1304 need not match the number of substrate holder locks 1316 on the boundary wall 1302, provided that the configuration is such that the substrate holder 1304 may be coupled to the boundary wall 1302. It should also be appreciated that the boundary wall clips 1310 (and corresponding substrate holder locks 1316 on boundary wall 1302) may have different arrangements on the frame 1308 of the substrate holder 1304.

Figure 16A:
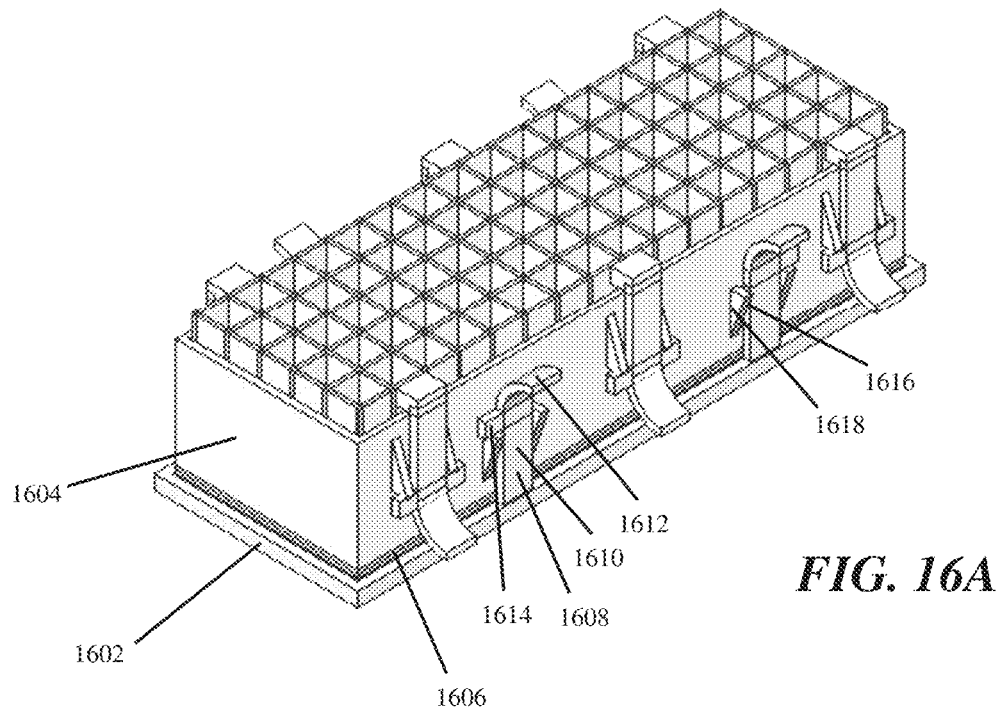
FIGS. 16A-16B are perspective views of different embodiments of multi-well separation devices in which the substrate holders and separation wall structures irreversibly couple to the boundary walls.

In the variations shown in FIGS. 3 and 4A-4B and FIG. 13, the substrate holder may reversibly couple the boundary wall and the substrate. However, it should be appreciated that in other variations, the substrate holder may irreversibly couple the boundary wall and the substrate. That is, once the substrate holder couples the boundary wall and the substrate, they may resist decoupling (i.e., may not be able to be decoupled without compromising the structural integrity of the components). In one such variation, all or a portion of the boundary wall clips may need to be broken off in order to decouple the substrate holder and boundary, which may cause decoupling to be irreversible. FIG. 16A shows such a variation, in which substrate holder 1602 irreversibly couples the boundary wall 1604 to the substrate 1606. The boundary wall clips 1608 may be configured to interface with the boundary wall 1604, in a manner similar to that described above with respect to FIG. 13. Boundary wall 1604 may have similar features to boundary wall 1302 of FIG. 13. That is, the boundary wall 1604 may comprise substrate holder locks 1616 corresponding to each boundary wall clip 1608. As shown in FIG. 16A, the substrate holder locks 1616 may each comprise two projections 1618. The two projections 1618 may have a triangular shape extending outwardly from the boundary wall 1604, with the triangular shape oriented such that the projection is at a minimum at the distal end of the projection and at a maximum at the proximal end of the projection.

The boundary wall clips 1608 may comprise an elongate portion 1610 and a curved portion 1612, with a horizontal portion 1614 between the elongate portion 1610 and the curved portion 1612, and having a greater width then the elongate portion 1610 or curved portion 1612. The two projections 1618 of the substrate holder locks 1616 may be spaced apart by a distance that is greater than the width of the elongate portion 1610 of the boundary wall clips 1608, but less than the width of the horizontal portion 1614 of the boundary wall clips 1608. As such, the two projections 1618 may each form a proximal horizontal surface configured to interface with a distal horizontal surface of the horizontal portions 1614 of the boundary wall clips 1608. The interface between the proximal horizontal surfaces of the projections 1618 and the distal horizontal surfaces of the horizontal portions 1614 of the boundary wall clips 1608 may resist distal motion of the substrate holder 1602 relative to the boundary wall 1604, in addition to sandwiching a boundary seal between the boundary wall 1604 and a substrate, or between a substrate and the substrate holder 1602, in those variations having a boundary seal. Once the boundary wall clips 1608 are interfaced with the boundary wall 1604, the curved portion 1612 must be snapped off in order for the boundary wall 1604 to be removed from the substrate 1606. As such, after the curved portion 1612 is snapped off, the boundary wall clips 1608 are no longer able to couple the boundary wall 1604 to the substrate 1606. The boundary wall 1604 and substrate holder 1602 may thus be decoupled only irreversibly.

Figure 16B:
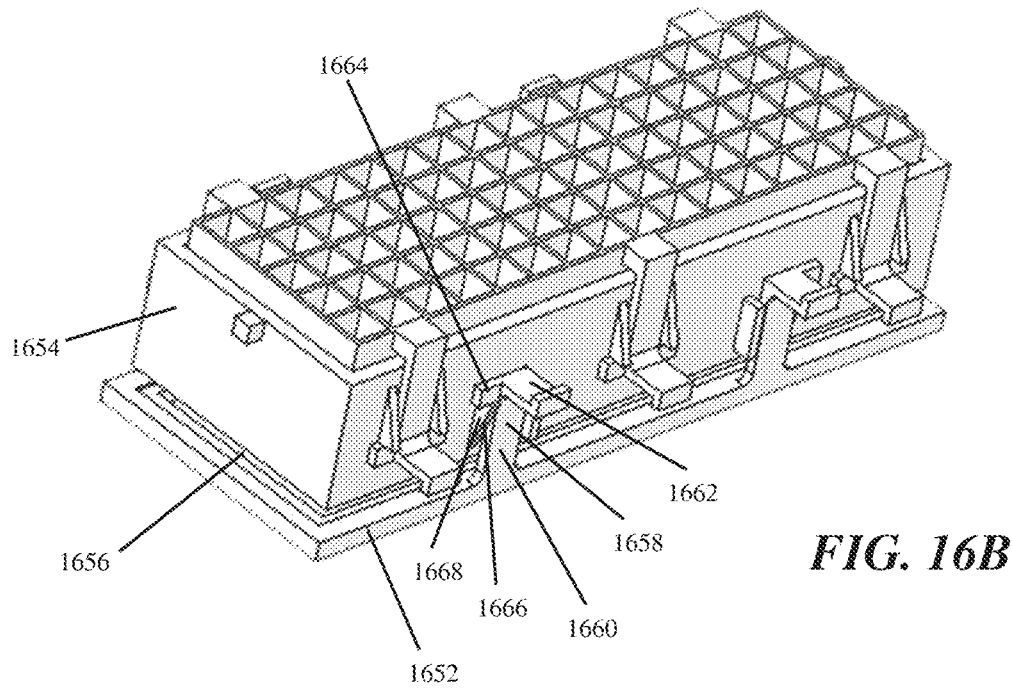

FIG. 16B shows another such variation in which the substrate holder 1652 irreversibly couples the boundary wall 1654 to the substrate 1656. The boundary wall clips 1658 may be configured to interface with the boundary wall 1654 in a manner similar to that described above with respect to FIG. 13. Boundary wall 1654 may have similar features to boundary wall 1604 of FIG. 16A. That is, the boundary wall 1654 may comprise substrate holder locks 1666 corresponding to each boundary wall clip 1658. As shown in FIG. 16B, the substrate holder locks 1666 may each comprise two projections 1668. The two projections 1668 may have a triangular shape extending outwardly from the boundary wall 1654, with the triangular shape oriented such that the projection is at a minimum at the distal end of the projection and at a maximum at the proximal end of the projection, or the projections 1668 may have other shapes, such as a rectangular shape.

The boundary wall clips 1658 may comprise an elongate portion 1660 and a perpendicular portion 1662, with a horizontal portion 1664 between the elongate portion 1660 and the perpendicular portion 1662, having a greater width then the elongate portion 1660 or perpendicular portion 1662. The perpendicular portion 1662 may be perpendicular to the elongate portion 1660, and the perpendicular portion 1662 may extend perpendicularly outward from the boundary wall 1654 when the boundary wall 1654 is coupled to the substrate holder 1652. The two projections 1668 of the substrate holder locks 1666 may be spaced apart by a distance that is greater than the width of the elongate portion 1660 of the boundary wall clips 1658, but less than the width of the horizontal portion 1664 of the boundary wall clips 1658. As such, the two projections 1668 may each form a proximal horizontal surface configured to interface with a distal horizontal surface of the horizontal portions 1664 of the boundary wall clips 1658. The interface between the proximal horizontal surfaces of the projections 1668 and the distal horizontal surfaces of the horizontal portions 1664 of the boundary wall clips 1658 may resist distal motion of the substrate holder 1652 relative to the boundary wall 1654, in addition to sandwiching a boundary seal between the boundary wall 1654 and a substrate, or between a substrate and the substrate holder 1652, in those variations having a boundary seal. Once the boundary wall clips 1658 are interfaced with the boundary wall 1654, the perpendicular portion 1662 must be snapped off in order for the boundary wall 1654 to be removed from the substrate 1656. As such, after the perpendicular portion 1662 is snapped off, the boundary wall clips 1658 are no longer able to couple the boundary wall 1654 to the substrate 1656. The boundary wall 1654 and substrate holder 1652 may thus be decoupled only irreversibly. In the variations shown in FIGS. 16A-16B, the separation well structure may also irreversibly coupled to the boundary wall using separation well clips and locks having a similar structure to the boundary wall clips and locks in FIGS. 16A-16B, wherein a portion of the separation well clips must be removed in order to uncouple the separation well structure after it has been coupled to the boundary wall.

Figure 17A:
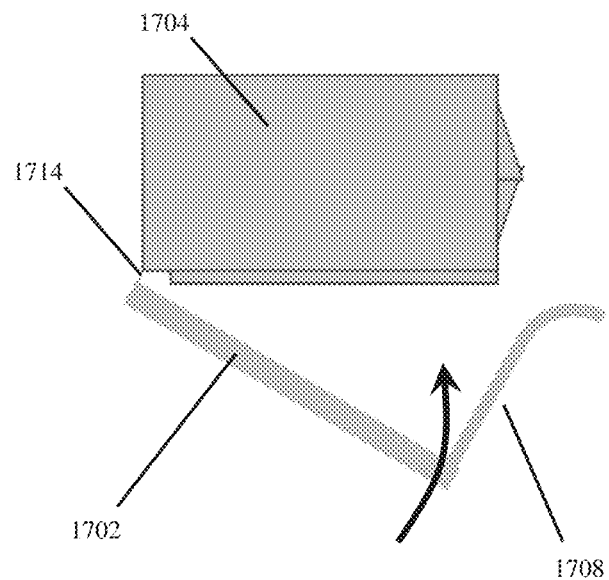
FIGS. 17A-17B are side views of a multi-well separation device wherein the substrate holder is attached to the boundary wall via a hinge, in a first configuration and a second configuration, respectively.
Figure 17B:
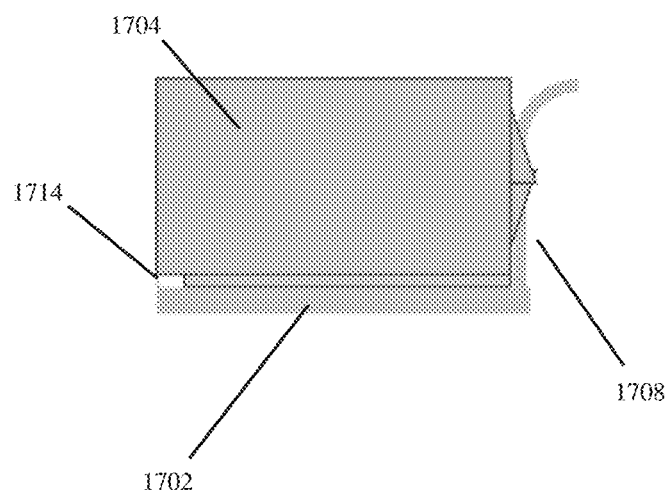

In another variation, the substrate holder may be attached to the boundary wall via a hinge. The hinge may connect the proximal surface of one side of the substrate holder to the distal surface of a corresponding side of the boundary wall. In order to form a holding cavity, the substrate holder and boundary wall may be rotated relative to each other about the hinge to bring the sides opposite from the hinge toward each other. The sides opposite from the hinge may then be coupled, for example using clips and locks similar to those described above. Before the substrate holder is coupled to the boundary wall, the substrate may be placed between the substrate holder and the boundary wall to sandwich it between the substrate holder and the boundary wall. FIGS. 17A-17B show an example of such a variation having boundary wall clips 1708 similar to the boundary wall clips 1608 of the substrate holder 1602 of FIG. 16A. As shown, the substrate holder 1702 may be attached to one side of the boundary wall 1704 via a hinge 1714. The substrate holder 1702 may be rotated about the hinge 1714 from a first position (FIG. 17A) to a second position (FIG. 17B) to sandwich the substrate between the substrate holder 1702 and the boundary wall 1704.

Figure 5:
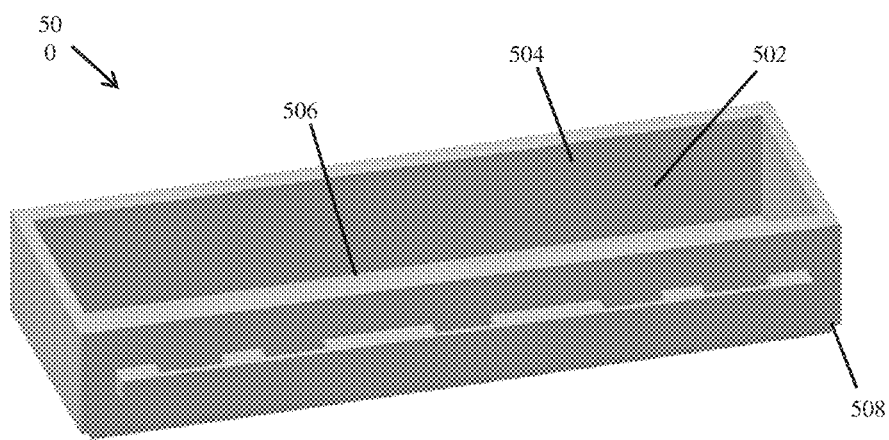
FIG. 5 is a perspective view of a holding cavity of a multi-well separation device comprising a boundary wall that is fixedly attached to the substrate.

Although the embodiment of the multi-well separation device 100 shown in FIGS. 1-4 has a boundary wall 202 that is separate from the substrate 302, in other embodiments of the multi-well separation device, the boundary wall may not be separate from the substrate. In some of these variations, the boundary wall may be fixedly attached to the substrate; in others of these variations, the boundary wall may be integral to the substrate. For example, FIG. 5 illustrates the holding cavity 502 of a multi-well separation device 500 comprising a boundary wall 504 that is fixedly attached to substrate 506. That is, in the embodiment of FIG. 5, the boundary wall 504 is bound to the substrate 506, instead of being coupled via a substrate holder or the like. The boundary wall 504 may be directly or indirectly bound to the substrate 506. In variations in which the boundary wall 504 is indirectly bound to the substrate, the distal side 508 of the boundary wall may be bound to a boundary seal (not shown), which in turn may be bound to the substrate 506. In variations in which the boundary wall 504 is directly bound to the substrate 506, the multi-well separation device 500 need not comprise a boundary seal. In variations in which the boundary wall 504 is directly bound to the substrate 506, the boundary wall 504 may be bound in any suitable manner, such as but not limited to an adhesive ring (e.g., silicone glue) bonding the distal side of the boundary wall 504 to the proximal side of the substrate 506, or a cast polymer material (e.g., a rigid rubber) on the boundary wall 504 that can be bound to the substrate 302. In other variations, the boundary wall may be integral to the substrate. That is, the boundary wall and substrate may be integrally formed from the same material, such as but not limited to polyacrylic, polyurethane, or polycarbonate materials, or the like.

Holding Cavity

Returning to the embodiment of the multi-well separation device 100 of FIGS. 1-4, the substrate 302 and the boundary wall 202 may form a holding cavity 450 when coupled. The holding cavity 450 may provide a region configured to hold a composition, such as a cell suspension, a gel, a pre-gel solution that may be later cured into a polymerized gel, a powder, or the like. It should be appreciated that a similar holding cavity may be formed by the boundary wall and substrate in embodiments in which the boundary wall is fixedly attached or integral to the substrate, as described above, such as the holding cavity 502 formed by the boundary wall 504 and substrate 302 described above and shown in FIG. 5.

While FIG. 2A shows the coupled boundary wall 202 and substrate 302 as forming a single integrated holding cavity 450, in other variations, the coupled boundary wall and substrate may form a holding cavity having more than one region. For example, in the variation mentioned above in which the boundary wall comprises a fifth portion, which may be attached to opposite portions of the boundary wall (e.g., on a first end to the first portion 202a and on a second end to the third portion 202c), the holding cavity may comprise two rectangular regions. These two regions may be separated by the boundary wall, such that composition located in one region will not be able to travel to the other region.

The holding cavity 450, and in turn the components forming it, may have any suitable dimensions. In some variations, the multi-well separation device 100 may be configured to use a standard glass slide as the substrate 302, and thus, the length and width of the substrate 302, boundary wall 202, and substrate holder 402 may be about 75 mm by 25 mm, respectively. In other variations, the multi-well separation device 100 may be configured to approximate a standard 96-well plate, and thus, the length and width of the substrate 302, boundary wall 202, and substrate holder 402 may be less than about 13 cm in its largest dimension, or about 130 mm by 85 mm. The depth of the holding cavity 450 (and thus the approximate height of the boundary wall 202) may in some variations be about 1 mm, about 3 mm, about 5 mm, about 7 mm, about 9 mm, about 11 mm, about 13 mm, about 15 mm, about 17 mm, about 19 mm, about 25 mm, about 30 mm, about 35 mm, about 40 mm, or more than about 40 mm.

Separation Well Structure

Figure 6A:
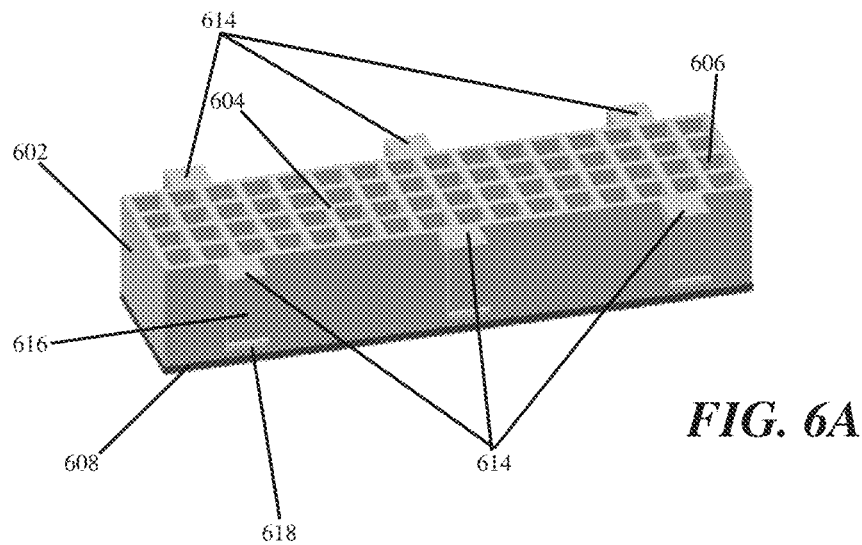
FIGS. 6A-6B are top and bottom perspective views of a separation well structure and separation seal.

As described briefly above, the multi-well separation device 100 may comprise a separation well structure 602 that may be placed within the holding cavity 450. FIG. 6A illustrates such a separation well structure 602 configured to be located within the holding cavity 450. When the separation well structure 602 is placed within the holding cavity 450, it may divide the composition (e.g., a cell suspension) in the holding cavity 450 into separated regions. This manner of dividing the composition into separated regions may be simpler and/or more efficient than traditional manners of dividing a composition into separated regions, such as individually pipetting into separate wells, which may require repeated transfer of compositions, as opposed to one-time transfer of the composition into the holding cavity. Once the contents are divided into separated regions, this may allow the separated regions to be subject to different processes (e.g., by introducing a different reagent into each region), as described in more detail below. Furthermore, the separation well structure may also be removed from the holding cavity, which may allow the contents of the separated regions to be modified in bulk. When it is desirable to perform the same process for each of the separated regions (e.g., a washing step), this may be simpler and more efficient than performing the process individually for each of the separated regions.

As shown in FIG. 6A, the separation well structure 602 may comprise a plurality of separation walls 604. In some variations, the separation walls 604 may comprise two orthogonal sets of parallel walls and may form a grid- or lattice-like structure, such that they form an array or matrix of openings 606 separated by the separation walls 604.

When the separation well structure 602 is coupled within the holding cavity 450, it may separate the holding cavity 450 into a plurality of separation wells 610. The separation walls 604 may form the lateral walls of the separation wells 610, while the substrate 302 may form the base of the separation wells 610. The contents of the holding cavity 450 may be separated and divided into the separation wells 610. The separation well structure 602 may comprise any suitable material or materials, such as but not limited to rubber, plastic, silicon, ceramic, metal, polymer, glass, or the like.

While in the variation of FIG. 6A the separation walls 604 have approximately the same height as the boundary wall 202 (e.g., in some variations about 1 mm, about 3 mm, about 5 mm, about 7 mm, about 9 mm, about 11 mm, about 13 mm, about 15 mm, about 17 mm, about 19 mm, about 25 mm, about 30 mm, about 35 mm, about 40 mm, or more), it should be appreciated that the separation walls 604 may have a lower height than boundary wall 202, so long as the height of the separation walls 604 (and thus the depth of the separation wells) is greater than the depth of the composition within the holding cavity 450 when the separation walls 604 are coupled within the cavity, in order to prevent the composition from flowing between separation wells 610 over the separation walls 604. It should also be appreciated that the separation walls 604 may have a greater height than the boundary wall 202. Similarly, while in the variation of FIGS. 6A-6B the separation well structure 602 substantially fills the holding cavity 450 (i.e., the cross-sectional dimensions of the separation well structure 602 are substantially the same as the cross-sectional dimensions of the holding cavity 450), the separation well structure need not fill the holding cavity 450. For example, the separation well structure 602 may have a smaller cross-sectional area than the holding cavity 450, and may thus only subdivide a portion of the suspension chamber 450 into separation wells 610.

The openings 606 may have any suitable cross-sectional area. In some variations, the largest dimension of the cross section of the openings may be about 1 µm to about 20 µm, about 20 µm to about 40 µm, about 40 µm to about 60 µm, about 60 µm to about 80 µm, about 80 µm to about 100 µm, about 100 µm to about 200 µm, about 200 µm to about 400 µm, about 400 µm to about 600 µm, about 600 µm to about 800 µm, about 800 µm to about 1 mm, about 1 mm to about 2 mm, about 2 mm to about 4 mm, about 4 mm to about 6 mm, about 6 mm to about 8 mm, about 8 mm to about 1 cm, greater than about 1 cm, about 1 µm to about 1 cm, about 100 µm to about 1 mm, or about 1 mm to about 1 cm. However, it should be recognized that in some variations, it may be desirable for the ratio between the height and cross-sectional area of the openings 606 to be of a particular value in order to counter the capillary effect. The resulting separation wells 610 may have any suitable volume, such as but not limited to less than about 100 µL, about 100 µL to about 200 µL, about 200 µL to about 400 µL, about 400 µL to about 600 µL, about 600 µL to about 800 µL, about 800 µL to about 1 mL, about 1 mL to about 10 mL, about 10 mL to about 20 mL, about 20 mL to about 40 mL, about 40 mL to about 60 mL, about 60 mL to about 80 mL, about 80 mL to about 100 mL, more than about 100 mL, about 100 µL to about 100 mL, or about 1 mL to about 10 mL.

Figure 6B:
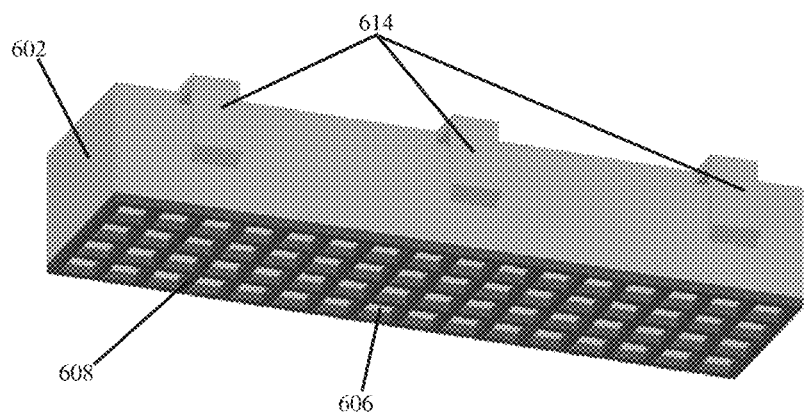

While the openings 606 are shown in FIGS. 6A-6B as having a square cross-sectional shape, the openings 606 may have any suitable shape, such as but not limited to a cross-section having the shape of a triangle, rectangle, any other quadrilateral (parallelogram, trapezoid, etc.), pentagon, hexagon, etc., any rounded shape (circle, ellipse, oval, etc.), or irregular shape. Furthermore, while the openings 606 are shown as having equal cross-sectional sizes, it should be appreciated that the openings 606 need not have the same sizes or shapes. Moreover, the cross-sections of the openings need not be the same throughout the openings 606. For example, in some variations, the cross-sectional area of each opening 606 at its proximal end may be greater than the cross-sectional area at its distal end; in other variations, the cross-sectional area of each opening at its distal end may be greater than the cross-sectional area at its proximal end. It should be appreciated that in these cases, the thickness of the separation walls 604 may correspondingly vary to create the variable cross-sectional area (e.g., for the former example, the thickness of the separation wells 604 may be greater at the distal end than the proximal end, and for the latter example, the thickness may be greater at the proximal end than at the distal end).

In the embodiment shown in FIGS. 6A-6B, the separation well structure 602 may define 64 openings 606, and thus when coupled within the holding cavity 450, the separation well structure 602 may separate the holding cavity 450 into 64 separation wells 610. It should be appreciated, however, that the separation well structure 602 may define any number of openings 606, and thus when coupled with the holding cavity 450, the separation well structure 602 may separate the holding cavity 450 into any number of separation wells 610. For example, the separation well structure 602 may define at least about 6, at least about 12, at least about 24, at least about 48, at least about 96, at least about 384, at least about 480, at least about 1536, at least about 3456, or more openings 606, and thus when coupled with the holding cavity 450 may separate the holding cavity 450 into at least about 6, at least about 12, at least about 24, at least about 48, at least about 96, at least about 384, at least about 480, at least about 1536, at least about 3456, or more separation wells 610. It should be understood that the number of openings 606 and separation wells 610 need not be limited by the numbers listed here. While in some variations the separation well structure 602 may define numbers of openings 606 found in standard microtiter laboratory plates, in other variations the separation well structure 602 may define non-standard numbers of openings 606, which may or may not be rectangular numbers.

It some variations, it may be desirable to maximize the number of separation wells 610 within a given cross-sectional area (e.g., the cross-sectional area of the holding cavity 450). In order to do so, it may be desirable to minimize the thickness of the separation walls 604. In some variations, the thickness of the separation walls may be about 50 µm to about 2000 µm. In some of these variations, the thickness of the separation walls may be about 200 µm to about 1800 µm. In some of these variations, the thickness of the separation walls may be about 400 µm to about 1600 µm. In some of these variations, the thickness of the separation walls may be about 600 µm to about 1400 µm. In some of these variations, the thickness of the separation walls may be about 800 µm to about 1400 µm. In some of these variations, the thickness of the separation walls may be about 1000 µm to about 1200 µm.

The multi-well separation device 100 may further comprise a second separation well structure. The second separation well structure may be configured to fit within one of the openings 606 of the first separation well structure 602. The second separation well structure may thus further subdivide a separation well 610 into a plurality of smaller separation wells, wherein each of these smaller separation wells has a volume that is less than the volume of the separation well 610 created by the first separation well structure 602. The second separation well structure may have similar design and function as the first separation well structure 602, as described in detail above, and including a separation seal as described in detail below. The second separation well structure may be coupled to the remainder of the multi-well separation device 100 in any suitable manner, such as but not limited to via clips connecting to the first separation well structure 602 or to the boundary wall 202, friction fit, or the like. It should be appreciated that the multi-well separation device 100 may further comprise additional separation well structures, such as a third, fourth, fifth, and so on.

It should also be appreciated that in some variations, the suspension cavities described herein may be used without a separation well structure. For example, the holding cavity may be used to hold a gel or solid composition, and a reagent loading device as described herein may be used to deposit one or more reagents or test agents onto or into the gel or solid composition. The gel or solid composition may sufficiently minimize migration or diffusion of the reagents or test agents, such that a separation well structure may not be needed. On the other hand, in some instances when the holding cavity is used to hold a gel or solid composition, a separation well structure may still be used. The separation well structure may be inserted into a liquid composition which may be subsequently cured, such that the contents of each separation well are polymerized into a gel, or the separation well structure may be inserted when the composition is in a gel form. In some of the instances where the separation well structure is inserted when the composition is in a gel form, the distal end of the separation well structure may comprise a sharpened tip to help facilitate division of the gel into each separation well. In some instances, the separation well structure may be configured to be inserted partially into the gel (i.e., such that a proximal portion of the gel is divided within individual separation wells, but a distal portion of the gel remains contiguous). In other instances, the separation well structure may be configured to be inserted such that the distal surface rests on the proximal surface of the gel or solid composition.

Separation Seal

Figure 6C:
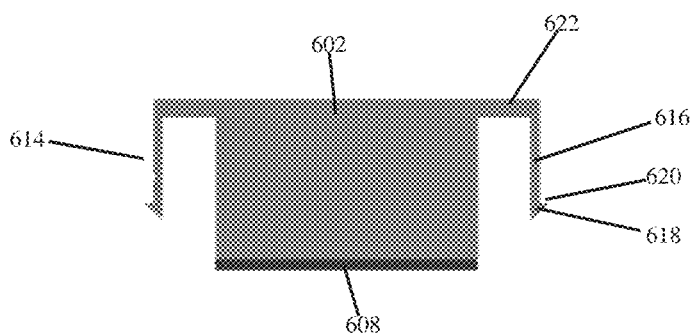
FIG. 6C is a side view of a separation well structure and separation seal of FIGS. 6A-6B.

The multi-well separation device 100 may further comprise a separation seal 608. When the separation well structure 602 and the substrate 302 are coupled, the separation seal 608 may create a leak-proof seal at the distal end of each separation well 610. This may allow each separation well 610 to be an isolated region, such that it may undergo processes or treatments distinct from its neighboring separation wells 610, as described in more detail below. As shown in FIGS. 6A-6C, the separation seal 608 may be located between the distal surfaces of the separation walls 604 of the separation well structure 602 and the proximal surface 304 of the substrate 302 when the separation well structure 602 and the substrate 302 are coupled. The separation seal 608 may cover the bottom edge of every separation well 610 and may provide sealing for every separation well 610 when pressed onto the substrate 302 when the separation well structure 602 and the substrate 302 are coupled. The separation seal 608 may comprise any suitable material for forming a seal, such as but not limited to rubber, plastic, or a polymer.

In the variation shown in FIGS. 6A-6C, the separation seal 608 may be coupled to the distal surfaces of the separation walls 604 of the separation well structure 602. The separation seal 608 may be attached to the separation well structure 602 in any suitable manner, such as but not limited to adhesives (glues, adhesive polymers, and the like), chemical bonding, or the like. However, it should be appreciated that in other variations, the separation seal 608 may be attached to the proximal surface 304 of the substrate 302. In yet other variations, the separation seal 608 may be attached to the boundary wall 202. In some such variations, the separation seal 608 may be integral to the boundary seal 204, or it may be attached to the boundary seal 204.

It should further be appreciated that the multi-well separation device need not comprise a separation seal. A separation seal may be unnecessary if the separation well structure and substrate are configured to form separation wells that can suitably hold a composition (e.g., a cell suspension) within them without leaking, without a separation seal. For example, this may be the case if the separation seal comprises a material such a rubber, plastic, or polymer that may be capable of forming a seal with the material of the substrate. In these cases, compressive force pressing together the separation well structure and the substrate may create a leak-proof seal directly between the separation well structure and the substrate, without requiring an intermediate separation seal. As another example, the multi-well separation device may not comprise a separation seal in some (but not all) variations in which it comprises a concentrating well structure, as described in more detail below. As yet another example, the multi-well separation device may not comprise a separation seal in some variations where the multi-well separation device is configured to hold a gel or solid composition. In some of these variations, however, the distal edges of the separation well structure may be thinned, sharpened, beveled, or the like in order to help the separation well structure to cut fully or partially through the gel or solid composition.

Separation Well Structure Attachment

As mentioned above, the separation well structure 602 may be configured to be coupled within the holding cavity 450. The separation well structure 602 and holding cavity 450 may be configured such that when coupled, there is sufficient compressive pressure between the separation well structure 602 and the substrate 302 that leak-proof separation wells 610 are formed. In some variations, the separation well structure 602 may be configured to be coupled within the holding cavity 450 via the boundary wall 202. In the embodiment shown in FIGS. 6A-6C, the separation well structure 602 may comprise separation well clips 614 configured to couple to the boundary wall 202. The separation well clips 614 may comprise a lateral portion 622, an elongate portion 616, and a tab 618. The lateral portion 622 may be attached on one end to the proximal surface of the separation well structure 602 and extend laterally away from the separation well structure 602. The elongate portion 616 may extend distally from the lateral portion 622 and may have a substantially planar shape, while the tabs 618 may be located at the distal end of the elongate portion 616 and may have an outwardly facing triangular shape, as shown in FIG. 6C.

The separation well clips 614 may be configured to interface with a portion of the boundary wall 202. As described above in reference to FIGS. 2A-2B, the boundary wall 202 may comprise two locking strips 208, which may comprise separation well locks 212. The separation well locks 212 may comprise openings formed between the boundary wall 202 and the locking strips 208, which are configured to interface with the separation well clips 614 of the separation well structure 602. The elongate portions 616 of the separation well clips 614 may fit within the openings of the separation well locks 212 between the boundary wall 202 and the locking strips 208, while the tabs 618 of the separation well clips 614 may hook over the distal surface of the locking strips 208, as shown in FIG. 1A. The interface between the proximal surface 620 of the tabs 618 (see FIG. 6C) and the distal surface of the locking strips 208 may resist proximal motion of the separation well structure 602 relative to the boundary wall 202 (and in turn of the coupled substrate holder 402 and substrate 302). The distal pressure on the proximal surface 620 of the tabs 618 from the distal surface of the locking strips 208 may generate a compressive pressure between the separation well structure 602 and the substrate 302, coupling together the boundary wall 202 and the separation well structure 602 and pressing the two together to form leak-proof separation wells 610 (in combination with the separation seal 608 and/or the concentrating well structure 702, described in more detail below).

While the variation shown in FIGS. 6A-6C comprises six separation well clips 614, it should be appreciated that the separation well structure 602 may have any suitable number of separation well clips 614 (e.g., one, two, three, four, five, six, seven, eight, or more), and the boundary wall 202 may have any suitable number of corresponding separation well locks 212. It should also be appreciated that the number of separation well clips 614 on the separation well structure 602 need not match the number of separation well locks 212 on the boundary wall 202, provided that the configuration is such that the separation well structure 602 may be coupled to the boundary wall 202. It should also be appreciated that the separation well clips 614 (and corresponding separation well locks 212 on the boundary wall 202) may have different arrangements on the separation well structure 602.

It should also be appreciated that the separation well structure may be coupled to the boundary wall via separation well clips having other designs. Another embodiment of a separation well structure 1306 is shown in FIG. 13. The separation well structure 1306 may comprise separation well clips 1322 configured to couple to the boundary wall 1302. The separation well clips 1322 may have a T-shape, comprising a vertical portion 1324 and a horizontal portion 1326. The vertical portion 1324 may have a substantially planar shape. The horizontal portion 1326 may be located at the proximal end of the vertical portion 1324 and may have a substantially planar shape extending outwardly beyond the laterally edges of the vertical portion 1324. The proximal end of the vertical portion 1324 may be attached to the separation well structure 1306 via a lateral extender 1328, which may be attached on a first (outside) end to the vertical portion 1324 and at a second (inside) end to the outside of the lateral wall of the separation well structure 1306. In other variations, the second end may be attached to the proximal surface of the separation well structure 1306.

The separation well clips 1322 may be configured to interface with a portion of the boundary wall 1302. The boundary wall 1302 may comprise separation well locks 1330. As shown in FIG. 13, the separation well locks 1330 may each comprise two projections 1332. The two projections 1332 may have a triangular shape extending outwardly from the boundary wall 1302, with the triangular shape oriented such that the projection is at a minimum at the distal end of the projection and at a maximum at the proximal end of the projection. The two projections 1332 may be spaced apart by a distance that is greater than the width of the vertical portion 1324 of the separation well clip 1322, but less than the width of the horizontal portion 1324 of the separation well clip 1322. As such, the two projections 1332 may each form a distal horizontal surface configured to interface with a proximal horizontal surface of the horizontal portions 1326 of the separation wall clips 1322. The interface between the distal horizontal surfaces of the projections 1332 and the proximal horizontal surfaces of the horizontal portions 1326 of the separation well clips 1322 may resist proximal motion of the separation well structure 1306 relative to the boundary wall 1302 (and in turn of the coupled substrate holder 1304 and substrate). The distal pressure on the proximal surface of the horizontal portion 1326 of the separation well clips 1322 from the separation well locks 1330 may generate a compressive pressure between the separation well structure 1306 and the substrate, coupling together the boundary wall 1302 and the separation well structure 1306 and pressing the two together to form leak-proof separation wells (in combination with a separation seal and/or a concentrating well structure, described in more detail below).

While the variation shown in FIG. 13 comprises six separation well clips 1322, it should be appreciated that the separation well structure 1306 may have any suitable number of separation well clips 1322 (e.g., one, two, three, four, five, six, seven, eight, or more), and the boundary wall 1302 may have any suitable number of corresponding separation well locks 1330. It should also be appreciated that the number of separation well locks 1330 need not match the number of separation well locks 1330 on the boundary wall 1302, provided that the configuration is such that the separation well structure 1306 may be coupled to the boundary wall 1302. It should also be appreciated that the separation well clips 1322 (and corresponding separation well locks 1316 on the boundary wall 1302) may have different arrangements on the separation well structure 1306.

Figure 14A:
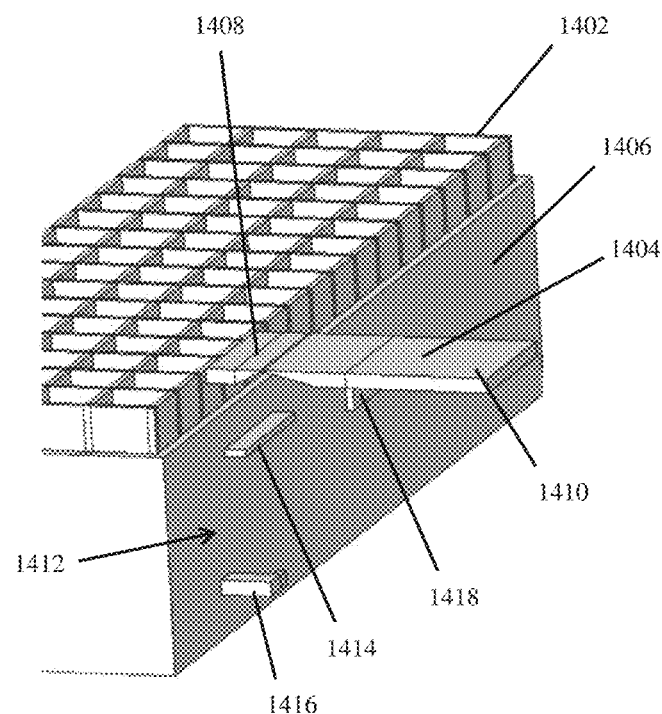
FIGS. 14A-14B are perspective views of a portion of a multi-well separation device.
Figure 14B:
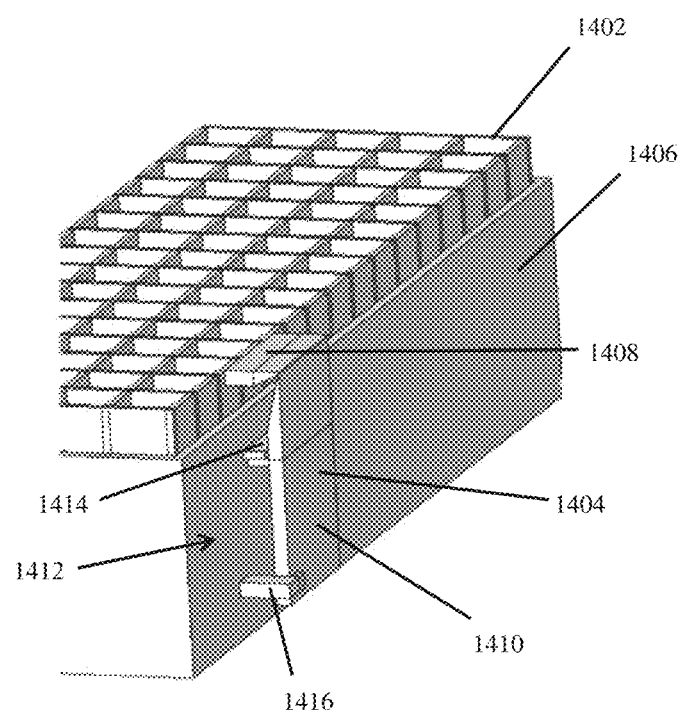

Yet another embodiment of separation well clip designs is shown in FIGS. 14A-14B. Shown there is separation well structure 1402, which may comprise separation well clips 1404 configured to couple to the boundary wall 1406. The separation well clip 1404 may comprise a horizontal portion 1408 and a vertical portion 1410, which may both have a substantially planar shape. The horizontal portion 1408 may be attached on a first (inside) end to the outside of the lateral wall of the separation well structure 1402, and at a second (outside) end to the inside end of the vertical portion 1410. In other variations, the first (inside) end may be attached to the proximal surface of the separation well structure 1402. The attachment joint between the horizontal portion 1408 and the vertical portion 1410 may be pivotable or rotatable, such that the separation well clip 1404 may be able to move from a first position, in which the horizontal portion 1408 and vertical portion 1410 may be parallel (as shown in FIG. 14A), to a second position, in which the horizontal portion 1408 and vertical portion 1410 may be orthogonal (as shown in FIG. 14B). When the separation well clip 1404 is in the first position, both the horizontal portion 1408 and the vertical portion 1410 may be substantially perpendicular to the boundary wall 1406. When the separation well clip 1404 is in the second position, the horizontal portion 1408 may be substantially perpendicular to the boundary wall 1406, and the vertical portion 1410 may be substantially parallel to the boundary wall 1406.

The separation well clip 1404 may be configured to interface with a portion of the boundary wall 1406. The boundary wall 1406 may comprise separation well locks 1412. The separation well locks 1412 may in some variations be configured to hold the separation well clips 1404 in the second position when interfaced. As shown in FIGS. 14A-14B, the separation well lock 1412 may each comprise a first projection 1414 and a second projection 1416. The first projection 1414 may comprise a horizontal bar extending from the outside surface of the boundary wall 1406. The first projection 1414 may be configured and located to correspond to a bar 1418 extending from the vertical portion 1410 of the separation well clip 1404. When the separation well clip 1404 is in the second position, the bar 1418 is located below the first projection 1414, such that the distal surface of the bar 1418 is pressed against the proximal surface of the first projection 1414. This may resist proximal motion of the separation well structure 1402 relative to the boundary wall 1406. The distal pressure on the proximal surface of the bar 1418 may generate a compressive pressure between the separation well structure 1402 and the substrate, coupling together the boundary wall 1304 and the separation well structure 1402 and pressing the two together to form leak-proof separation wells (in combination with a separation seal and/or concentrating well structure, described in more detail below). The second projection 1416 may be configured to hold the separation well clip 1404 in the second position. The second projection 1416 may have an L-shape, and may be located distally to the first projection 1414, such that when the separation well clip 1404 is in the second position, the vertical portion 1410 is held in place by the L-shape of the second projection 1416, as shown in FIG. 14B. The second projection 1416 may be flexible, such that when the separation well clip 1404 is moved from the first position to the second position, the second projection 1416 may flex to allow the separation well clip 1404 to enter the second position. Once the separation well clip 1404 is in the second position, the second projection 1416 may return to the position shown in FIGS. 14A-14B.

While FIGS. 14A-14B depicts only one separation well clip 1404, it should be appreciated that the separation well structure 1402 as a whole may have any suitable number of separation well clips 1404 (e.g., one, two, three, four, five, six, seven, eight, or more), and the boundary wall 1406 may have any suitable number of corresponding separation well locks 1412. For example, the separation well structure 1402 may have two or three separation well clips 1404 per length side of the separation well structure. It should also be appreciated that the number of separation well locks 1412 need not match the number of separation well clips 1404 on the boundary wall 1406, provided that the configuration is such that the separation well structure 1402 may be coupled to the boundary wall 1406. It should also be appreciated that the separation well clips 1404 (and corresponding separation well locks 1412 on the boundary wall 1406) may have different arrangements on the separation well structure 1402.

Figure 15A:
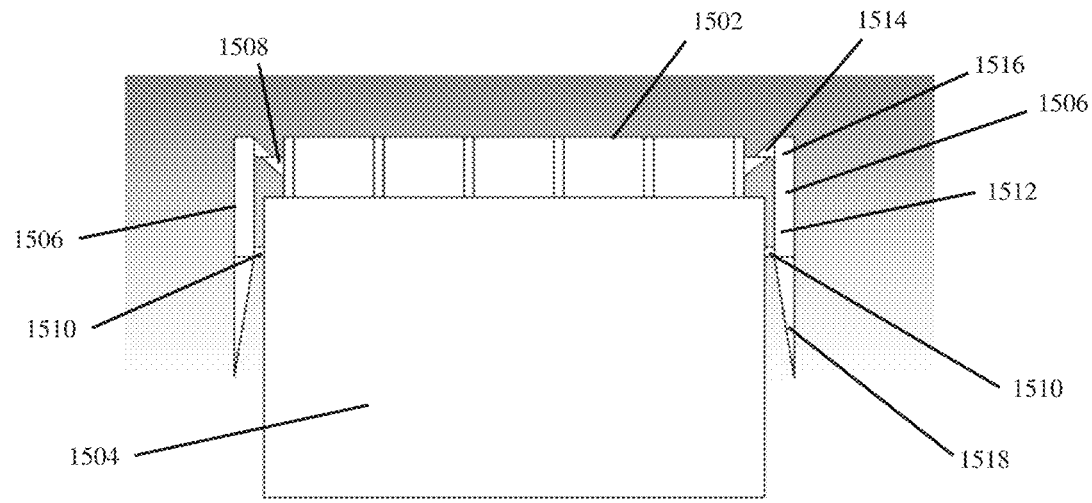
FIGS. 15A-15B are side views of a multi-well separation device, with the separation well clips in a first configuration and second configuration, respectively.
Figure 15B:
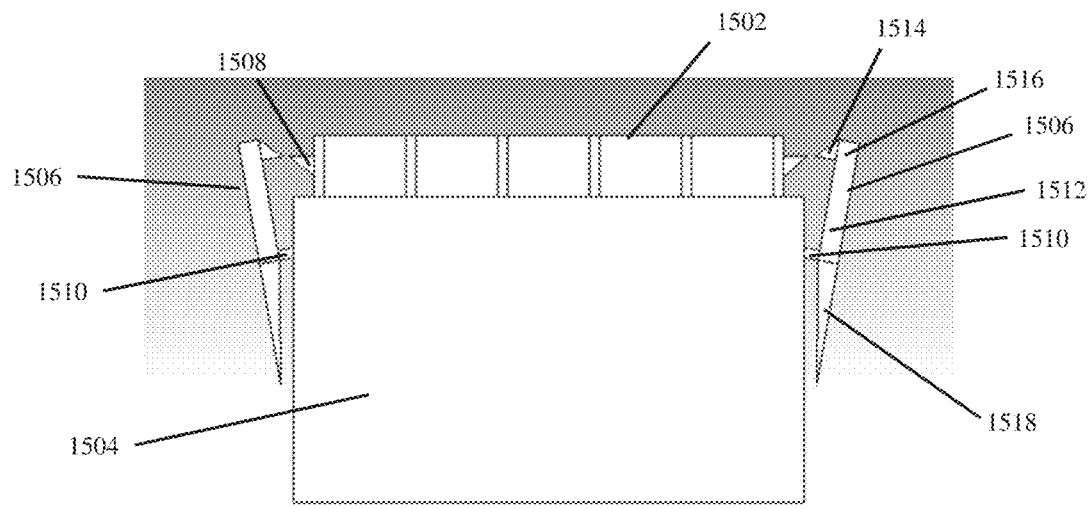

Yet another embodiment of separation well clip designs is shown in FIGS. 15A-15B. Shown there is separation well structure 1502 and boundary wall 1504. In the variation shown there, the separation well structure 1502 and boundary wall 1504 may be configured to be coupled by a separation well clip 1506 attached to boundary wall 1504, and which may interface with a separation well lock 1508 attached to separation well structure 1502. The separation well clips 1506 may be moveable between a first position (FIG. 15A) and a second position (FIG. 15B), where the separation well structure 1502 is coupled to the boundary wall 1504 in the second position, and uncoupled from the boundary wall 1504 in the first position. In some variations, the separation well clip 1506 may be moveable between the first position and second position by being pivotable or rotatable at attachment point 1510. In some variations, the separation well clip 1506 may be pivotable or rotatable about the attachment point 1510 due to the elasticity of the material (e.g., plastic). In other variations, the separation well clip 1506 may be pivotable or rotatable about the attachment point 1510 via a hinge.

The separation well clip 1506 may comprise a main body 1512 and a hook 1514 located at the proximal end 1516 of the main body 1512. The main body 1512 may have a substantially planar shape. The attachment point 1510 may be located between the proximal end 1516 and distal end 1518 of the main body 1512, such that when the separation well clip 1506 moves from the first position to the second position, the proximal end 1516 may move away from the boundary wall 1504 and separation well structure 1502, while the distal end 1518 may move toward the boundary wall 1504. The distal end 1518 of the main body 1512 may be tapered on its inner surface, such that the distal end 1518 does not resist the separation well clip 1506 from being moved into the first position in which the distal end 1518 is closer to the boundary wall 1504 than in the second position. The hook 1514 of the separation well clip 1506 may thus move toward the boundary wall 1504 and separation well structure 1502 when the separation well clip 1506 is moved from the first position to the second position. When the hook 1514 is in the second position, its distal surface may interface with the separation well lock 1508 located on the separation well structure 1502.

As shown in FIGS. 15A-15B, the separation well locks 1508 may be attached to the side of the separation well structure 1502. In other variations, the separation well locks 1508 may be attached to the proximal surface of the separation well structure 1502. The separation well locks 1508 may comprise a bar having a proximal surface configured to interface with the distal surface of the hook 1514 of the separation well clips 1506. When the separation well locks 1508 are interfaced with the separation well clips 1506, the bar may be located below the hook 1514, such that the distal surface of the hook 1514 may be pressed against the proximal surface of the bar of the separation well lock 1508. This may resist proximal motion of the separation well structure 1502 relative to the boundary wall 1504. The distal pressure on the separation well locks 1508 may generate a compressive pressure between the separation well structure 1502 and the substrate, coupling together the separation well structure 1502 and the boundary wall 1504 and pressing the two together to form leak-proof separation wells (in combination with a separation seal and/or concentrating well structure, described in more detail below). The separation well clips 1506 may be biased toward the first position (shown in FIG. 15A), which may maintain the coupling of the separation well structure 1502. In other variations, the device may comprise a mechanism to lock the separation well clips 1506 in the first position after the separation well structure 1502 is coupled.

It should be appreciated that the separation well structure 1502 may have any suitable number of separation well clips 1506 (e.g., one, two, three, four, five, six, seven, eight, or more), and the boundary wall 1504 may have any suitable number of corresponding separation well locks 1508. In some variations, the separation well structure 1502 may comprise between two and four clips per length side of the separation well structure 1502. It should also be appreciated that the number of separation well locks 1508 need not match the number of separation well clips 1506, provided that the configuration is such that the separation well structure 1502 may be coupled to the boundary wall 1504. It should also be appreciated that the separation well clips 1506 (and corresponding separation well locks 1508 on the separation well structure 1502) may have different arrangements on the boundary wall 1504.

Returning the embodiment of the multi-well separation device 100, the separation well structure 602 may removably couple to the holding cavity 450. That is, the design of the coupling mechanism between the separation well structure 602 and the holding cavity 450 may be such that the separation well structure 602 can be removed from the holding cavity 450 after the two elements have been coupled. The ability to uncouple and be removed from the holding cavity may allow the separation well structure to be inserted to initially separate the composition within the holding cavity into separation wells, and then may allow the separation well structure to be removed to recombine the composition.

In some variations, the separation well structure may be reversibly removably coupled to the holding cavity, such that after the separation well structure has been uncoupled from the holding cavity, it may be recoupled to re-separate the composition within the holding cavity into the separation wells. FIGS. 6A-6C show one variation of a separation well structure that can be reversibly removably coupled to a holding cavity. As shown there, the tabs 618 of the separation well clips 614 may be configured to be flexed inward under the application of inward pressure. In order to allow for inward flexing of the tabs 618 when coupled, there may be a space between the separation well clips 614 and the outer surface of the boundary wall 202; that is, the opening of the separation well locks 212 between the boundary wall 202 and the locking strips 208 may be wider laterally than the thickness of the elongate portion 616 of the separation well clips 614. When the tabs 618 are flexed inward, they may no longer interface with the distal surface of the locking strips 208, which may allow a proximally directed force (e.g., from pushing or pulling proximally on the separation well structure 602) to remove the separation well structure 602 from the holding cavity 450 by decoupling the separation well clips 614 from the separation well locks 212.

The separation well structure 1306 of multi-well separation device 1300 shown in FIG. 13, separation well structure 1402 shown in FIGS. 14A-14B, and separation well structure 1502 shown in FIGS. 15A-15B may similarly reversibly removably couple to the suspension cavities. With respect to separation well structure 1306 of multi-well separation device 1300 shown in FIG. 13, the separation well structure 1306 may removably couple to the holding cavity formed by boundary wall 1302, substrate holder 1304, and the substrate (and boundary wall seal in some variations). In this variation, the separation well clips 1322 may be configured to be flexed outward under the application of outward pressure. When the separation well clips 1322 are flexed outward, they may no longer interface with the distal horizontal surface of the projections 1332 of the separation well locks 1330, which may allow a proximally directed force (e.g., from pushing or pulling proximally on the separation well structure 1306) to remove the separation well structure 1306 from the holding cavity by decoupling the separation well clips 1322 from the separation well locks 1330. Similarly, in the variations shown in FIGS. 14A-14B and 15A-15B, the separation well clips 1404 and 1506, respectively, may be moved from the second position to the first position to decouple the separation well structures 1402 and 1502, respectively, from the boundary walls 1406 and 1504, respectively.

In other variations, the separation well structure may be irreversibly removably coupled to the holding cavity. In these variations, the separation structure may be removed from the holding cavity once coupled, but may not be able to then be recoupled into the holding cavity. This may be because, for example, in some variations uncoupling the separation well structure from the holding cavity irreversibly affects the structure of the separation well structure such that it cannot be recoupled (e.g., the separation well clips 614 may need to be broken in order to remove the separation well structure).

Concentrating Well Structure

The multi-well separation device 100 may optionally comprise a concentrating well structure 702. The concentrating well structure 702 may be configured to reduce the cross-sectional area of a distal portion of the separation wells 610. This may be advantageous, for example, because it may concentrate the target agent within each separation well 610 into a smaller cross-sectional area at the base of the separation well 610. In some variations, the concentrating well structure may comprise a thin layer of material, such as but not limited to a soft-elastic material (e.g., silicone, rubber, or the like), which may be configured to be located between the separation well structure and the substrate. Generally, the concentrating well structure may comprise a plurality of openings, which one the proximal end may correspond to the distal end of the openings of the separation well structure, and the openings may narrow in the proximal to distal direction. The distal ends of the openings in the concentrating well structure may allow the composition within the separation wells to interact with the substrate. In variations in which the substrate comprises a coating (described in detail above), this may allow the composition to interact with the coating. Thus, in these variations, the openings of the concentrating structure may in effect contain the substance comprising the coating, such as but not limited to proteins, polymers, hydrogels, or chemical coatings.

Figure 7A:
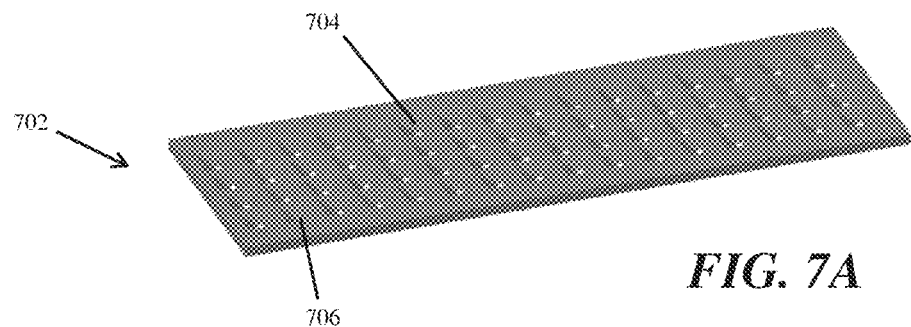
FIGS. 7A-7B are perspective and top views of a concentrating well structure.
Figure 7B:
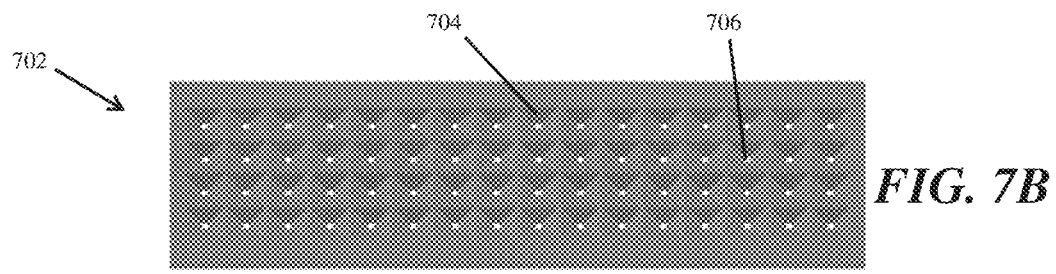

FIGS. 7A-7B illustrate perspective and top views of one embodiment of a concentrating well structure 702, respectively. As can be seen there, the concentrating well structure 702 may comprise a thin structure comprising plurality of openings 704. The cross-sectional shape of the openings 704 at the proximal side may be configured to correspond to the cross-sectional shape of the separation wells 610. The openings 704 may have an inverted truncated square pyramidal shape, such that the cross-sectional area of the openings 704 decreases from proximal to distal. At the distal end of the opening 704, a portion of the substrate 302 (and any coating) may be exposed.

Figure 8A:
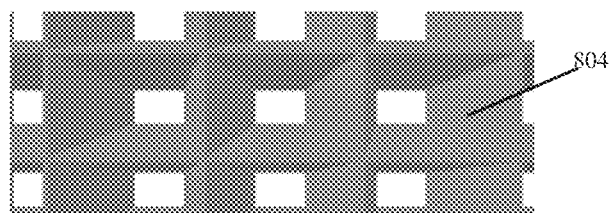
FIGS. 8A-8B are close-up views from the top and side, respectively, of another embodiment of a concentrating well structure.
Figure 8B:
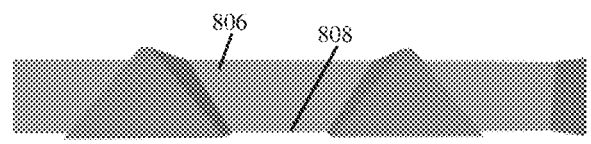

FIGS. 8A-8B illustrate close-up views from the top and side, respectively, of another embodiment of a concentrating well structure 802 having openings 804 also with an inverted truncated square pyramidal shape. As can be seen in FIG. 8B, the cross-sectional area of the openings 804 at their proximal end 806 is greater than the cross-sectional area of the openings 804 at their distal end 808. In other variations, the openings may have other shapes, such as but not limited to a truncated cone or a pyramidal frustum. In yet other variations, the openings may be closed on the distal end; that is, the composition within the separation wells may not come into contact with the substrate.

Figure 9:
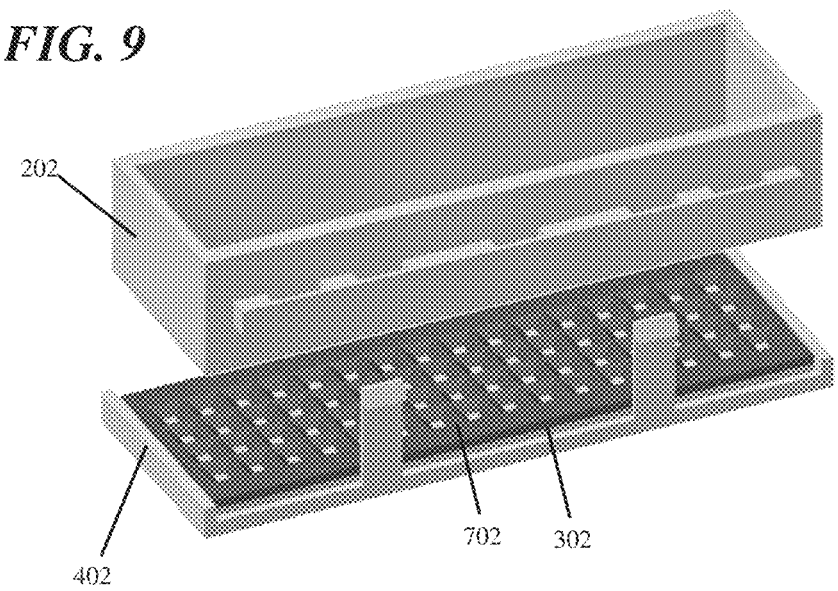
FIG. 9 is a perspective view of a boundary wall, concentrating well structure, substrate, and substrate holder.

As mentioned above, the concentrating well structure may be located between the separation well structure and the substrate. In some variations in which the multi-well separation device comprises a concentrating well structure, the multi-well separation device may not comprise a separation seal. For example, the multi-well separation device may comprise a concentrating well structure without a separation seal in variations in which the concentrating well structure comprises a material such as a rubber, plastic, or polymer that may be capable of forming a seal between the substrate and the separation well structure. In these variations, a concentrating well structure may be attached to the proximal surface of a substrate (as shown in FIG. 9); it may be attached to a boundary wall; or it may be attached to a boundary seal (e.g., by attaching the outer edges of the concentrating well structure to the inner edges of the boundary seal). The concentrating well structure may be attached to these elements in any suitable manner, such as but not limited to adhesives (glues, adhesive polymers, and the like), chemical bonding, or the like.

In other variations in which the multi-well separation device comprises a concentrating well structure, the multi-well separation device may also comprise a separation seal. For example, the multi-well separation device may comprise both a concentrating well structure and a separation seal in variations in which the concentrating well structure comprises a material not generally capable of forming a sufficient seal between the substrate, the concentrating structure, and the separation well structure, such as glass or a hard plastic. In these variations, the separation seal may be located between the substrate and the concentrating well structure and/or between the concentrating well structure and the separation well structure. When a separation seal is located between the substrate and the concentrating well structure, the separation seal may be attached to the proximal surface of the substrate, the distal surface of the concentrating well structure, or the boundary wall; when a separation seal is located between the concentrating well structure and the separation well structure, the separation seal may be attached to the proximal surface of the concentrating well structure, the distal surface of the separation well structure, or the boundary wall.

In some variations, the multi-well separation devices described herein may further comprise a cover. The cover may be configured to fit over the multi-well separation device to cover the holding cavity. In some variations, the cover may be configured to individually seal the top of each separation well when the separation well structure is coupled within the holding cavity.

Reagent Loading Devices

Described also herein are reagent loading devices. In some variations, the reagent loading devices may be configured to deliver a reagent or test agent to each of the separation wells 610 created by the coupled separation well structure 602 and holding cavity 450. In other variations, the reagent loading devices may be used independently of the multi-well separation devices described here. For example, the reagent loading devices may in some instances be used with multi-well plates having fixed walls.

Protrusions

Figure 10A:
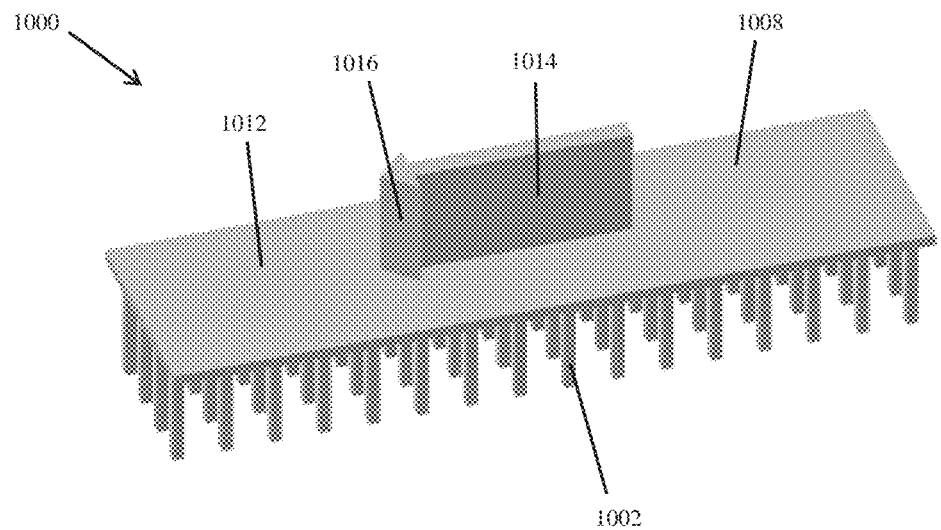
FIGS. 10A-10B are top and bottom perspective views, respectively, of a reagent delivery device.
Figure 10B:
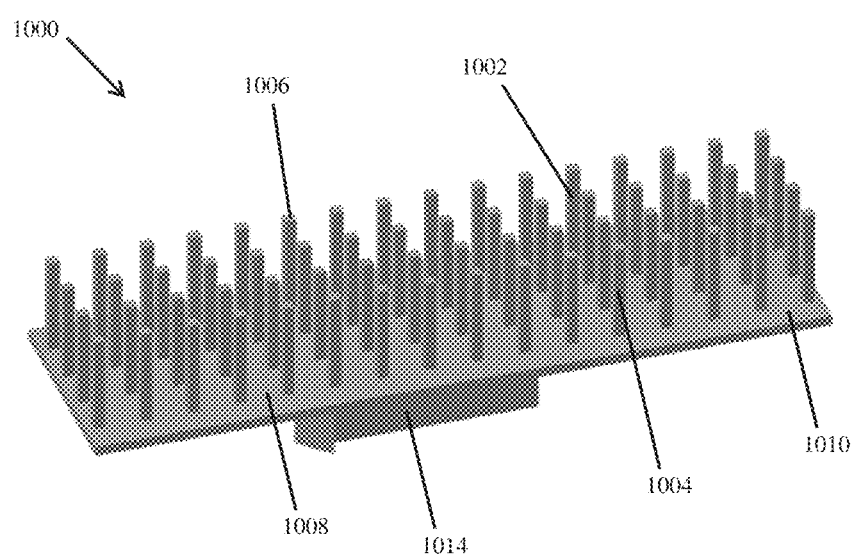
Figure 18:
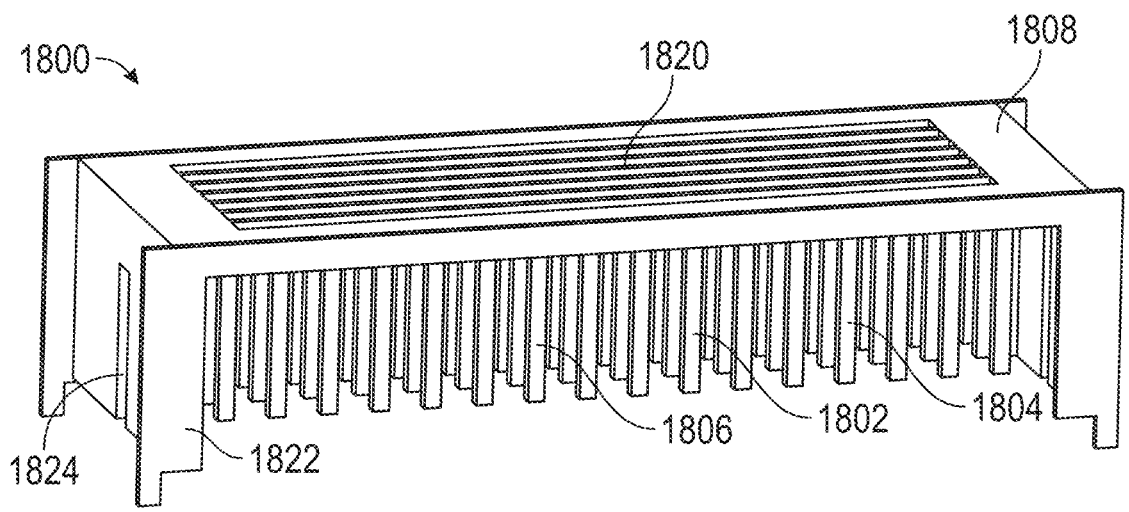
FIG. 18 is a perspective view of a reagent delivery device.

In the variations shown in FIGS. 10A-10B and FIG. 18, the reagent loading devices 1000 and 1800, respectively, may comprise a plurality of protrusions 1002 and 1802, respectively. Each protrusion 1002 or 1802 may comprise a stem 1004 or 1804 and a closed tip 1006 or 1806, respectively, described in more detail below. The protrusions may comprise any suitable material or materials, such as but not limited to plastic, silicon, metal, or a polymer. In some variations the stems and closed tips may comprise the same materials, while in other variations they may comprise different materials.

Figure 11:
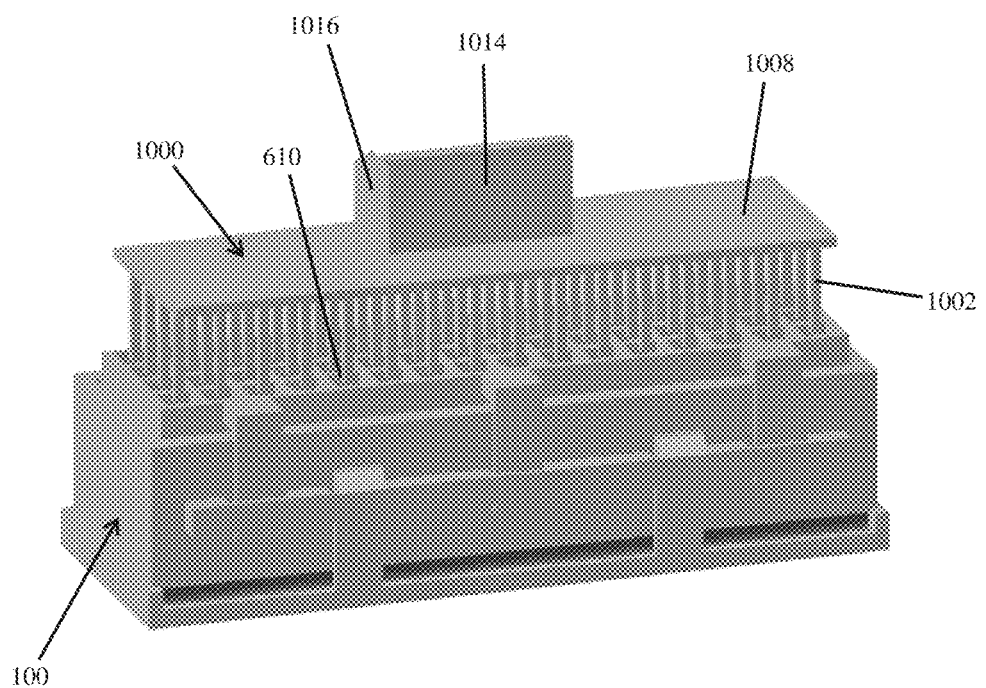
FIG. 11 is a perspective view of the reagent delivery device of FIGS. 10A-10B being inserted into the multi-well separation device of FIGS. 1A-1B.

In some variations, the reagent loading devices 1000 or 1800 may be configured to be used with a multi-well separation device (e.g., with multi-well separation device 100, as shown in FIG. 11), but it need not be configured to be used with a multi-well separation device. In variations in which the reagent loading devices are configured to be used with the multi-well separation device 100, the number of protrusions may be configured to correspond to the number of separation wells 610 in the multi-well separation device 100. However, it should be appreciated that the reagent loading devices may be used with a multi-well separation device having more or fewer separation wells 610 than the number of protrusions, or they may not be used with a multi-well separation device. For example, FIGS. 23A-23B, 24A-24B, 25A-25B, 28A-28C, 30A-30B, 31B-31D, and 32 show reagent loading devices configured to be located above only a portion of the separation wells, and thus having fewer protrusions than the number of separation wells.

In variations in which the reagent loading device is configured to be used with a multi-well separation device, the size and spacing of the protrusions may be configured to correspond to the separation wells of the multi-well separation device. More specifically, for example, if the reagent loading devices 1000 or 1800 are configured to be used with the multi-well separation device 100, the cross-sectional size of the protrusions 1002 or 1802 may be configured such that the protrusions can fit within the separation wells 610. In some variations, the largest cross-sectional dimension of the protrusions may be about 1 μm to about 10 μm, about 10 μm to about 100 μm, about 100 μm to about 1 mm, about 1 mm to about 5 mm, about 5 mm to about 1 cm, about 1 cm to about 2 cm, larger than about 2 cm, about 1 μm to 2 cm, or about 1 mm to about 1 cm.

In variations in which the reagent loading device is configured to be used with a multi-well separation device, such as multi-well separation device 100, the length of the protrusions may be such that when the reagent loading device is interfaced with the multi-well separation device, the closed tips of the reagent loading device may be fully submerged within the contents of each separation well. In some variations the length of the protrusions may be about 1 mm to about 2 mm, about 2 mm to about 4 mm, about 4 mm to about 6 mm, about 6 mm to about 8 mm, about 8 mm to about 1 cm, about 1 cm to about 2 cm, about 2 cm to about 4 cm, about 4 cm to about 6 cm, longer than about 6 cm, about 1 mm to about 6 cm, about 1 mm to about 1 cm, or about 1 cm to about 6 cm. It should be appreciated that each protrusion need not have the same configuration.

As mentioned above, the protrusions 1002 or 1802 may comprise closed tips 1006 and 1806, respectively, which may each be configured to hold a reagent. The closed tips may be "closed" in the sense that they may not comprise an opening at the distal end that is connected to a cavity in the stem of the protrusion through which the reagent travels when it is deposited by the closed tip. This is in contrast to a device such as a pipette or the like, which comprises a cavity in the stem within which a composition is held, and an opening out of the cavity through which the composition travels when it is deposited by the pipette. A pipette or the like generally holds a composition within a cavity at least in part due to a partial vacuum within the cavity. In contrast, the closed tips of the reagent loading device may be designed to hold the reagent outside the tip (not within a cavity in the stem) due to the interactions (e.g., adhesive forces) between the closed tip and the reagent and due to interactions (e.g., surface tension) within the reagent.

The closed tips (e.g., closed tips 1006 or closed tips 1806) may have any suitable geometry for holding the reagent in such a way, including but not limited to a pointed shape or cone having a blunt tip (see FIG. 12A), square shape (see FIGS. 12B-12C and 12E), circular shape (see FIGS. 12D and 12F-12H), or the like. In some variations, the closed tips may be flat (see FIGS. 10A-140B). In other variations, the closed tips may comprise a depression—for example, they may be concave (e.g., have a hemispherical depression) (see FIG. 12H) or may comprise a cylindrical (or other shaped)

recess (see FIG. 12G). In yet other variations, the closed tips may comprise one or more linear depressions. For example, the closed tips may comprise one linear depression (see FIGS. 12B and 12D), they may comprise two perpendicular linear depressions (see FIG. 12C), or they may comprise a plurality of linear depressions arranged in a grid-like arrangement. In other variations, the closed tips may comprise two parallel plates, between which the reagent may be held, or one or more capillaries within which the reagent may be held. Such tips, such as a concave tip, or a tip other comprising a depression, may allow the reagent to be held more securely by the closed tip, for example by providing more surface area for adhesive forces between the closed tip and the reagent.

The surface of each closed tip may be smooth, or the surface may be rough (i.e., having surface irregularities). The closed tips may have any suitable dimensions. In some variations, the largest cross-sectional dimension of the closed tips may be about 1 µm to about 10 µm, about 10 µm to about 100 µm, about 100 µm to about 1 mm, about 1 mm to about 10 mm, larger than about 10 mm, about 1 µm to about 10 mm, about 1 µm to about 1 mm, or about 1 mm to about 10 mm. It should be appreciated that each closed tip need not have the same configuration.

In some variations, the closed tips (e.g. closed tips 1006 or closed tips 1806) may comprise a porous material, such as a polymer gel or a hydrogel (see FIGS. 12E-12F), polymer-based sponge, or mesh, or in some variations may comprise a matrix, such as a dried fibrous structure, containing the reagent. For example, the closed tips may comprise cellulose (e.g., nitrocellulose, paper-like material), glass fibrous mesh, silk fibrous mesh, and the like. In some of these variations, all or a portion of the closed tip may be dissolvable when the closed tips of the reagent loading device (e.g. reagent loading device 1000 or reagent loading device 1800) are lowered into liquid or solution, such as by being lowered into the separation wells of a multi-well separation device (e.g., multi-well separation device 100). In variations in which all or a portion of the closed tip 1006 is dissolvable, the dissolvable material may comprise any suitable material, such as but not limited to a salt, micro-particles, nano-particles, polyglycolide, poly (lactic acid), or poly (lactic-co-glycolic) acid co-polymer, or combinations thereof. In other variations, all or a portion of the closed tip 1006 may be meltable when the closed tips 1006 of the reagent loading device 100 are lowered into liquid or solution, such as by being lowered into the separation wells of a multi-well separation device (e.g., multi-well separation device 100). In variations in which all or a portion of the closed tip 1006 is meltable, the dissolvable material may comprise any suitable material, such as but not limited to DMSO.

The closed tips (e.g., closed tips 1006 or closed tips 1806) may each be located at the distal end of a stem (e.g., stem 1004 of reagent loading device 1000 or stem 1804 of reagent loading device 1800). In some variations the closed tips may be integral to the stems, while in other variations, the closed tips may be attached to the stems in any suitable manner (e.g., using adhesives (glues, adhesive polymers, and the like), welding, mechanical fasteners, chemical bonding, a combination of these methods, or the like). The proximal ends of the stems may be connected to a plate, which may form an array of the protrusions. For example, as shown in FIGS. 10A-10B, the proximal ends of the stems 1004 may be connected to the distal surface 1010 a plate 1008 of reagent loading device 1000, which may form an array of the protrusions 1002. In some variations the stems 1004 may be integral to the plate 1008, while in other variations, the stems 1004 may be attached to the plate 1008 in any suitable manner (e.g., using adhesives (glues, adhesive polymers, and the like), welding, mechanical fasteners, chemical bonding, a combination of these methods, or the like). As another example, as shown in FIG. 18, the proximal ends of the stems 1804 may be connected to the distal surface 1810 of a plate 1808 of reagent loading device 1800, which may form an array of protrusions 1802. The plate 1808 may comprise grooves 1820 on its proximal surface, which may be configured to interface with a vibration unit, described in more detail below. The plate 1808 may also comprise legs 1822, which may be configured to protect the closed tips 1806, as described in more detail below.

The stems (e.g., stem 1004 of reagent loading device 1000 or stem 1804 of reagent loading device 1800) may have a length such that when the reagent loading device is interfaced with the multi-well separation structure 100, the closed tips (e.g., closed tips 1006 or closed tips 1806) may be fully submerged within the contents of each separation well 610. For example, in some variations the length of the stems may be about 1 mm to about 2 mm, about 2 mm to about 4 mm, about 4 mm to about 6 mm, about 6 mm to about 8 mm, about 8 mm to about 1 cm, about 1 cm to about 2 cm, about 2 cm to about 4 cm, about 4 cm to about 6 cm, longer than about 6 cm, about 1 mm to about 6 cm, about 1 mm to about 1 cm, or about 1 cm to about 6 cm.

The stems may have any suitable cross-sectional dimensions, which may be smaller or larger than the cross-sectional dimensions of the closed tips. In some variations, the largest cross-sectional dimension of the stems may be about 1 µm to about 10 µm, about 10 µm to about 100 µm, about 100 µm to about 1 mm, about 1 mm to about 10 mm, larger than about 10 mm, about 1 µm to about 10 mm, about 1 µm to about 1 mm, or about 1 mm to about 10 mm. It should be appreciated that in some variations the stems may have variable cross-sectional dimensions along their length (e.g., they may taper distally, taper proximally, or taper towards a midpoint). It should also be appreciated that each stem need not have the same configuration.

Orientation Features

The reagent loading devices may optionally comprise orientation features that may promote the reagent loading device being inserted in a particular orientation into wells. In some variations, the orientation features may be indicators of orientation, thus providing the user information that allows the user to correctly orient the reagent loading device relative to the wells. In other variations, the orientation features may be orientation keys that dictate that the reagent loading device be inserted into wells in a particular orientation. In these variations, the receiving wells may have a corresponding orientation key that allows the reagent loading device to be inserted into the wells in only a particular orientation. In some cases, these receiving wells may be the separation wells of a receiving multi-well separation device described herein. In some other cases, the receiving wells may be part of a receiving plate having fixed walls, such as a multi-well plate. The corresponding orientation key of the receiving device may be integral to the receiving device (e.g., to the multi-well separation device described herein, or to a multi-well plate), or it may be part of an adaptor configured to be added to the receiving device, as described in more detail below.

FIGS. 10A-10B and 11 show one variation of a reagent loading device having an orientation feature comprising an indicator of orientation. As shown there, the indicator may comprise a handle 1014 attached to the proximal surface 1012 of the plate 1008, which may comprise an arrow 1016 on one side. It should be appreciated that the indicator may have any suitable form. For example, in some variations, the indicator may comprise a truncation on one corner of the plate 1008. In other variations, the indicator may comprise a visual indicator, such as a pigment or color, textual indicator, texture, or the like, located in a particular location on the plate 1008.

As mentioned above, in other variations, the orientation feature may comprise an orientation key that may dictate that the reagent loading device be inserted into wells in a particular orientation. The orientation key may prevent the reagent loading device from being inserted into wells (such as the wells of a multi-well separation structure described herein, or of a multi-well plate having fixed walls) in an incorrect orientation, and may only allow the reagent loading device to be inserted into the wells when the reagent loading device is in the proper orientation relative to the receiving device (that is, when each protrusion of the reagent locating device will enter the desired well when the reagent loading device is lowered into the receiving device).

It should be appreciated that the orientation key of the reagent device and corresponding orientation key of the receiving device may have any number of configurations or other physical shapes. In some variations, the one or more orientation keys may have an asymmetrical shape, such that the orientation features of the reagent delivery device may only interface properly with the corresponding orientation key of the receiving device when the reagent loading device is in the correct orientation relative to the receiving device. The orientation keys and corresponding keys on the receiving device may have any suitable shape, such as half circles, angled slots, bent or curved slots, triangles, crescents, parallelograms, or the like.

Figure 19A:
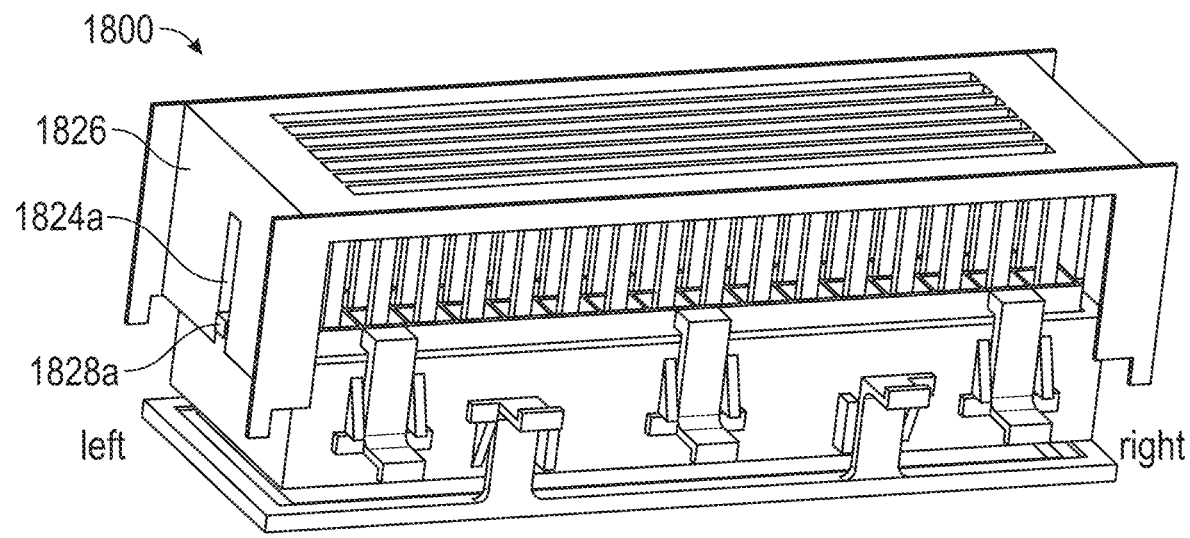
FIGS. 19A-19B are perspective views of the reagent delivery device of FIG. 18 partially inserted and fully inserted into a multi-well separation device, respectively.
Figure 19B:
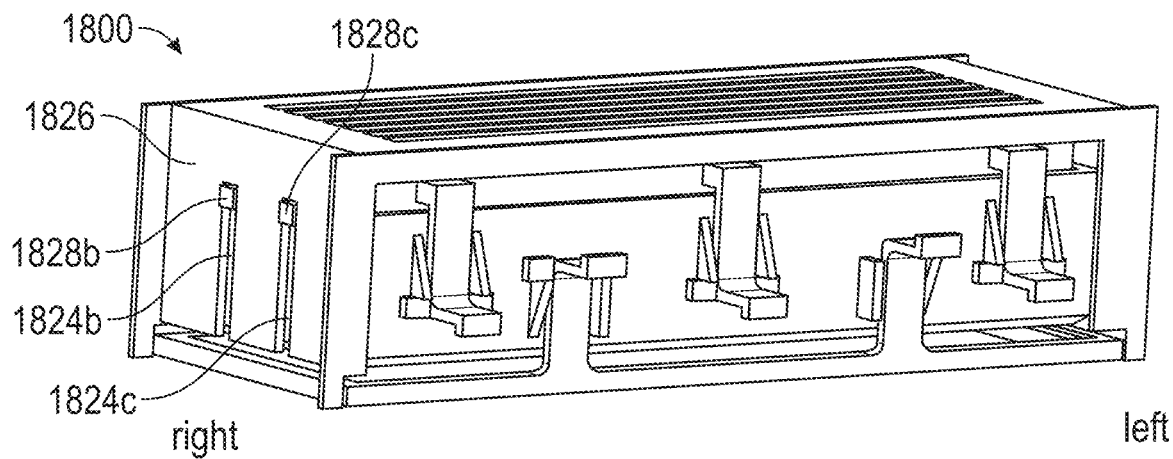

An example of a reagent loading device comprises an orientation key is shown in FIG. 18. As shown there, the orientation feature comprises one or more slots 1824. As shown in FIGS. 19A-19B, the reagent loading device 1800 may comprise two sides 1826. One side 1826, shown in FIG. 19A, may comprise a single slot 1824a, while the other side 1826, shown in FIG. 19B, may comprise two slots 1824b and 1824c. A corresponding multi-well separation structure may comprise a corresponding orientation feature. More specifically, the multi-well separation structure may comprise one end with a tab 1828a corresponding to slot 1824a, and one end with two tabs 1828b and 1828c corresponding to slots 1824b and 1824c. The slots 1824 and tabs 1828 may correspond such that the reagent loading device 1800 may be lowered into the multi-well separation device when the two components are correctly aligned, but cannot be lowered into the multi-well separation device when the relative orientations are reversed.

Figure 22:
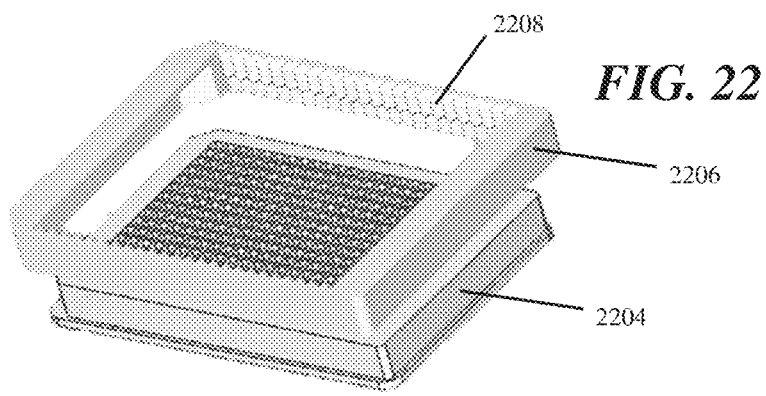
FIG. 22 is a perspective view of a multi-well separation device and adaptor.

In other variations in which the receiving device comprises a corresponding orientation key, the corresponding orientation key may be part of an adaptor, rather than integral to the receiving device. The adaptor may be configured to attach to a multi-well separation device or other receiving device. One example of such an adaptor is shown in FIG. 22. As shown there, an adaptor 2206 may comprise an outer frame configured to fit over multi-well separation device 2204. The adaptor 2206 may comprise keys 2208. The keys 2208 may extend along two opposite sides of the adaptor 2206, and may face inward, forming a gap 2210 between the keys 2208 and the outer edge of the multi-well separation device 2204.

Figure 23A:
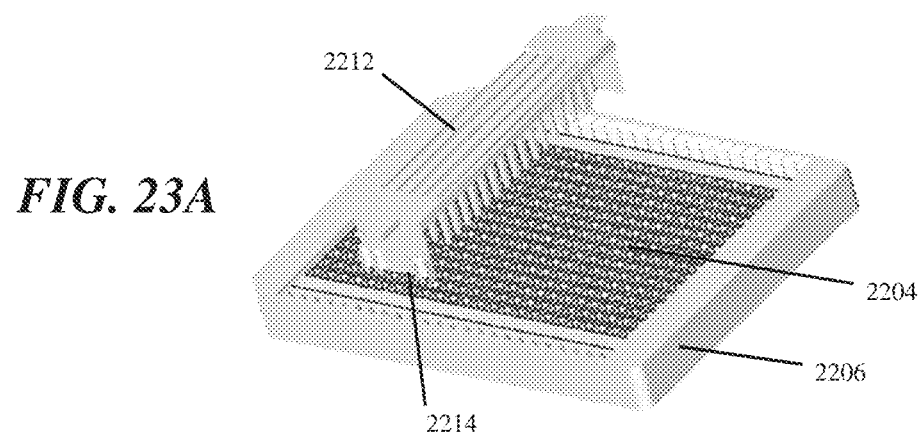
FIGS. 23A and 23B are perspective and top views, respectively, of a reagent loading device corresponding to the multi-well separation device and adaptor of FIG. 22.
Figure 23B:
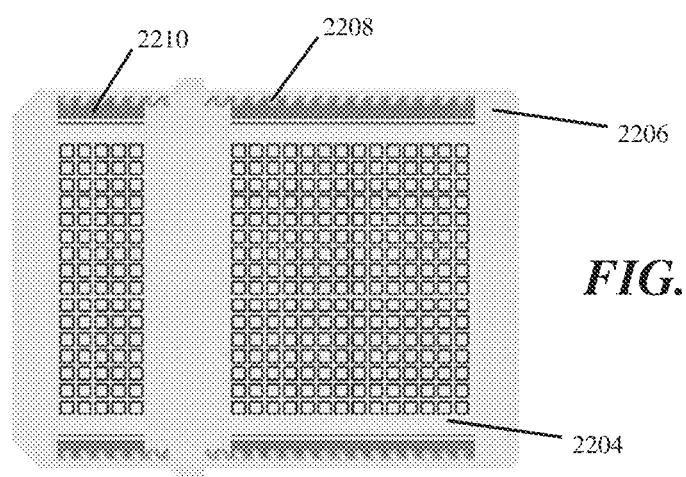

A reagent loading device (e.g., reagent loading device 2212) may comprise notches 2214 corresponding to the keys 2208, as shown for example in FIG. 23A-23B. FIGS. 25A-25B show close-up views of the keys 2208 of the adaptor 2206 and the notches 2214 of the reagent loading device 2212. When the reagent loading device 2212 is oriented correctly relative to the adaptor 2206, as shown in FIG. 25A, the shapes of the keys 2208 and notches 2214 correspond. However, when the reagent loading device 2212 is oriented incorrectly relative to the adaptor 2206, as shown in FIG. 25B, the shapes of the keys 2208 and notches 2214 may not correspond. In some variations, the reagent loading device 2212 may not be able to be lowered into the multi-well separation device when the keys 2208 and notches 2214 do not correspond. The keys 2208 and notches 2214 may also be configured to guide the protrusions of the reagent loading device 2212 into the separation wells of the multi-well separation device. That is, when the keys 2208 and notches 2214 are property aligned, each protrusion will be located above a separation well.

As the reagent loading device 2212 is lowered into the multi-well separation device 2204, the notches 2208 of the reagent loading device 2212 may enter the gap 2210 between the keys 2208 and the outer edge of the multi-well separation device 2204, with reagent loading device 2212 oriented such that the keys 2208 correspond to the notches 2214.

In some instances, it may be desirable for the orientation keys to restrict the orientation of insertion of the reagent loading device, while still allowing the reagent loading device to impart vibrations to the wells of the receiving device. This may, for example, allow the reagent loading device to be used to mix the contents of the receiving device. This may in some variations be achieved by having the keys configured to restrict the reagent loading device only during insertion (i.e., when the reagent loading device is partially loaded into the multi-well separation device), but when the reagent loading device is fully loaded into the multi-well separation device, the reagent loading device is no longer restricted by the keys and may move in order to impart vibrations.

Figure 24A:
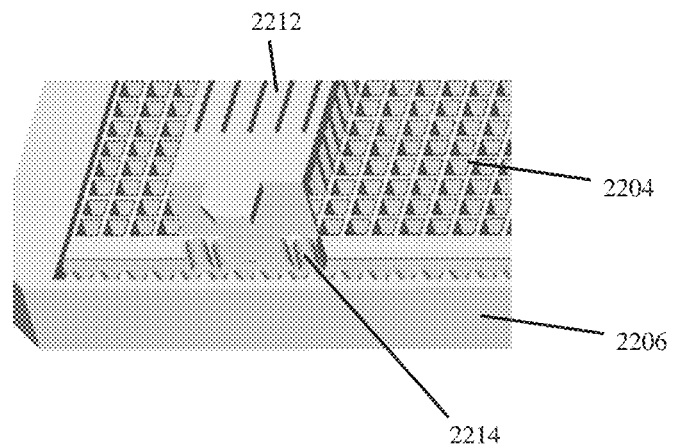
FIGS. 24A-24B are close-up perspective views of portions of a reagent loading device and multi-well separation device and adaptor or adaptor alone.
Figure 24B:
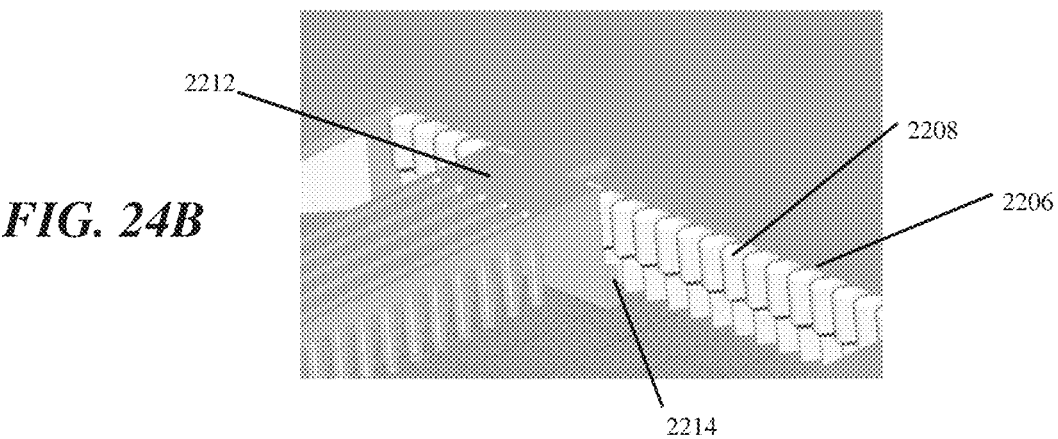

For example, as shown in FIG. 24B, the reagent loading device 2212 and adaptor 2206 may be adapted such that the keys 2208 and notches 2214 only interface as the reagent loading device 2212 is being inserted into the multi-well separation device 2204, but once the reagent loading device 2212 is fully inserted into the multi-well separation device 2204, the keys 2208 and notches 2214 no longer interface. This may allow the reagent loading device 2212 to move relative to the multi-well separation device 2204 in order to mix the contents of the separation wells.

This is achieved, as shown in FIG. 24B, by the keys 2208 and notches 2214 extending only partially along the inner surface of the adaptor 2206 and the outer end surface of the reagent loading device 2212, respectively. As shown there, the keys 2208 may extend only within the top half of the inner surface of the adaptor 2206, while the notches 2208 may extend only within the bottom half of the outer end surface of the reagent loading device 2212. As such, the keys 2208 and notches 2214 may interface tightly when the reagent loading device is less than half-way inserted into the multi-well separation device, therefore restricting the orientation of the reagent loading device and its movement relative to the multi-well separation device. However, when the reagent loading device is more than half-way inserted into the multi-well separation device, the keys 2208 and notches 2214 may not interface tightly, such that there is clearance between the keys 2208 and notches 2214, therefore allowing the reagent loading device to move within a range of motion relative to the multi-well separation device. In some variations, along the bottom half of the inner surface of the adaptor 2206 there may be a smaller version of the keys, as shown for example in FIG. 24B, which may prevent substantial lateral movement of the reagent loading device while still allowing the range of motion sufficient to allow vibration of the reagent loading device in order to promote mixing of the context of the separation wells, as described in more detail herein. It should be appreciated, however, that in some instances (e.g., when mixing is not required, or mixing is not carried out by lateral motion of the reagent loading device) one or more of the keys and notches may tightly interface when the reagent loading device is fully inserted into the multi-well separation device (e.g., one or both of the keys and notches may extend along the full length of the adaptor and reagent loading device).

It should be appreciated that the orientation features may comprise any suitable shape that dictates orientation. As one example, the orientation features may comprise angled slots 2602, as shown in FIG. 26A. FIG. 26B shows another example of orientation features comprising right-angle triangles 2604. In some variations in which the orientation features are located on opposite sides of the adaptor, the orientation features on each of the opposite sides may have a different shape (e.g., a half-circle on one side and a rectangle on the other side), orientation, or dimension, such that the corresponding notches on the reagent loading device correspond only to the keys on one of the sides. It should also be appreciated that while the adaptor is described herein as comprising keys and the reagent loading device is described as comprising corresponding notches, in other variations, the reagent loading device may comprise keys and the adaptor may comprise corresponding notches.

Figure 27:
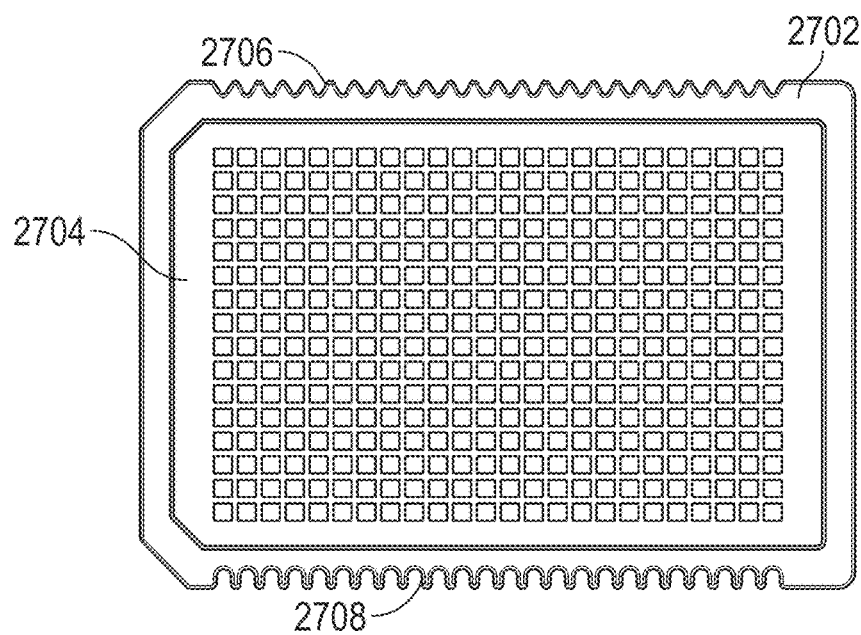
FIG. 27 shows a top view of another a multi-well separation device and adaptor.
Figure 28A:
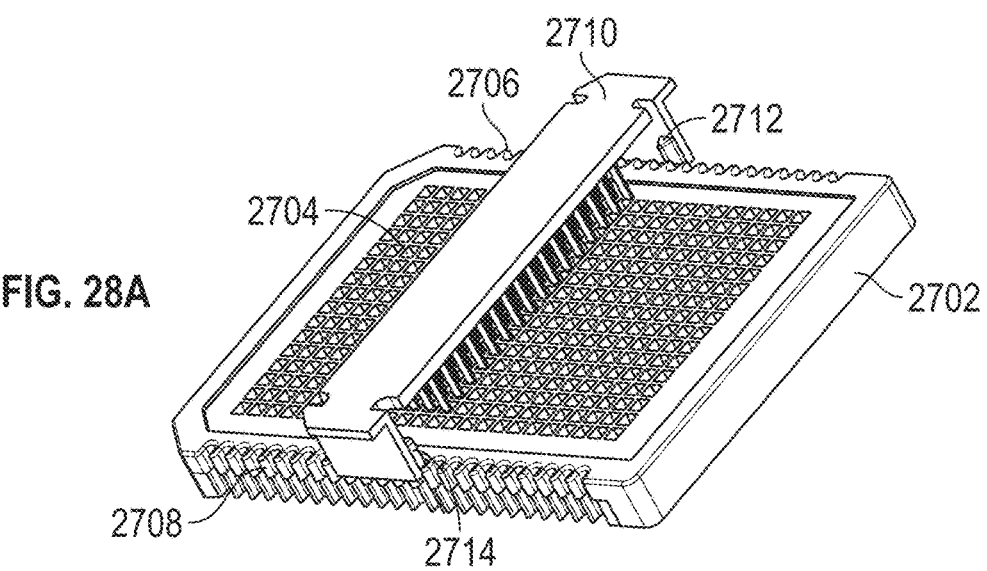
FIGS. 28A-28B are perspective views of a reagent loading device before being lowered and fully lowered, respectively, relative to the assembled multi-well separation device and adaptor of FIG. 27.
Figure 28B:
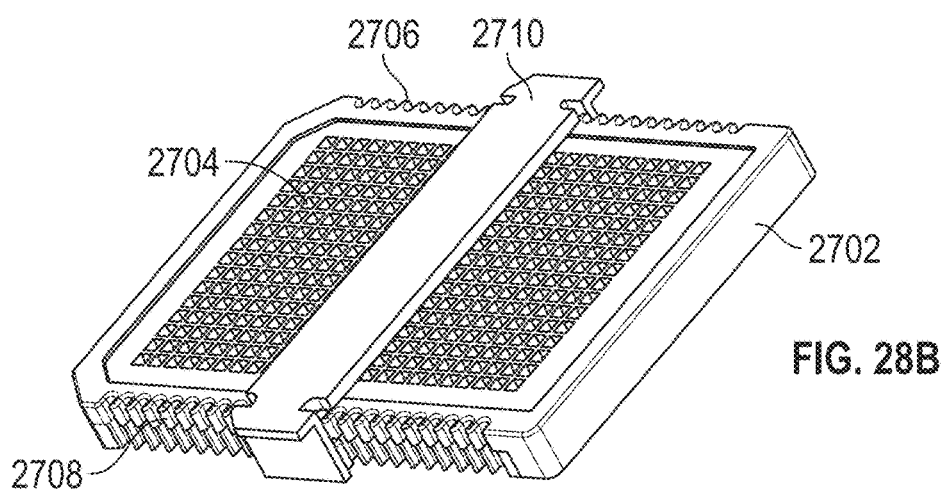

While the adaptor may comprise inwardly facing keys, thus forming a gap between the keys and the outer edge of the multi-well separation device, in other variations, the adaptor may comprise outwardly facing keys. An example of such an adaptor is shown in FIGS. 27 and 28A-28B. As shown there, adaptor 2702 may be configured to be placed over the multi-well separation device 2704 to form an outer frame. The adaptor 2702 may comprise one or more keys facing outwardly on one or more outer edges (as shown in there, on two opposing outer edges). The keys 2706 on the first edge may comprise a first shape (here, triangles), while the keys 2708 on the second edge (opposite the first edge) may comprise a second shape (here, protrusions formed by an inverted scalloped edge). It should be appreciated that the first and second shapes may be any suitable distinct shapes, such that a reagent loading device having corresponding notches will interface with the adaptor in a first orientation but not in a second orientation.

As shown in FIGS. 28A-28B, a corresponding reagent loading device 2710 may comprise notches 2712 and 2714 corresponding to the keys 2706 and 2708, respectively, which may be located on the inner surfaces of the ends of the reagent loading device 2710. As in the variation of FIGS. 22 through 25A-25B, the keys 2706 and 2708 may extend only within the top half of the outer surface of the adaptor 2702, while the notches 2712 and 2714 may extend only within the bottom half of the inner end surface of the reagent loading device 2710. As such, the keys and notches may interface tightly as the reagent loading device is being inserted into the multi-well separation device, but they may not interface tightly when the reagent loading device is fully inserted into the multi-well separation device, as described in more detail with respect to FIGS. 24A-24B.

Figure 29:
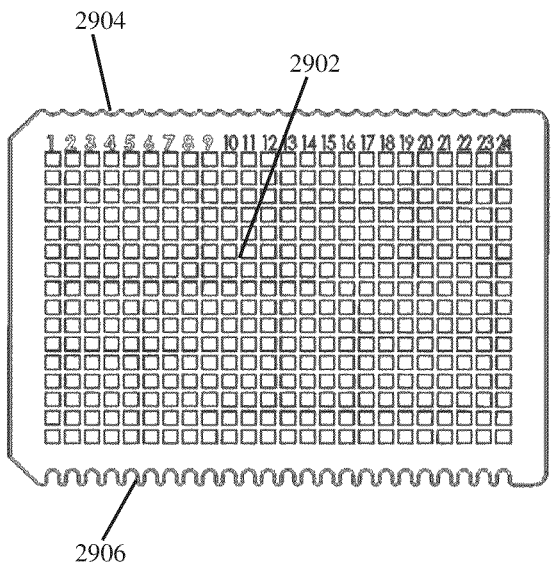
FIG. 29 is a top view of another a multi-well separation device having integral orientation keys.
Figure 30A:
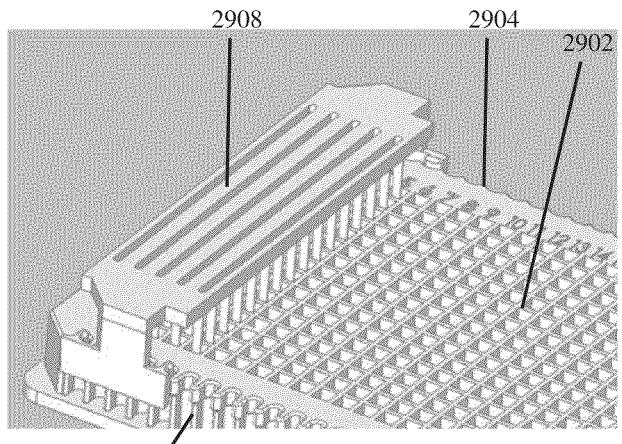
FIGS. 30A-30B are perspective views of a reagent loading device partially lowered and fully lowered, respectively, relative to the multi-well separation device of FIG. 29.
Figure 30B:
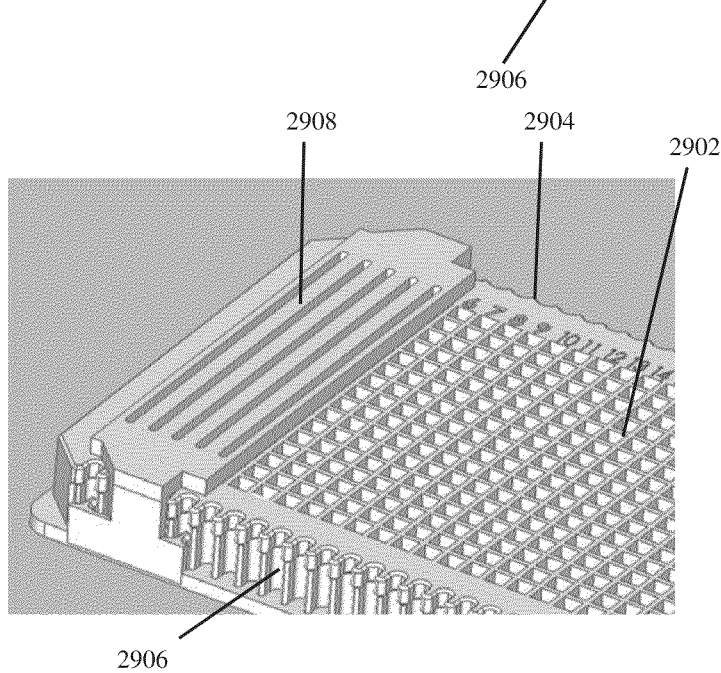
Figure 31A:
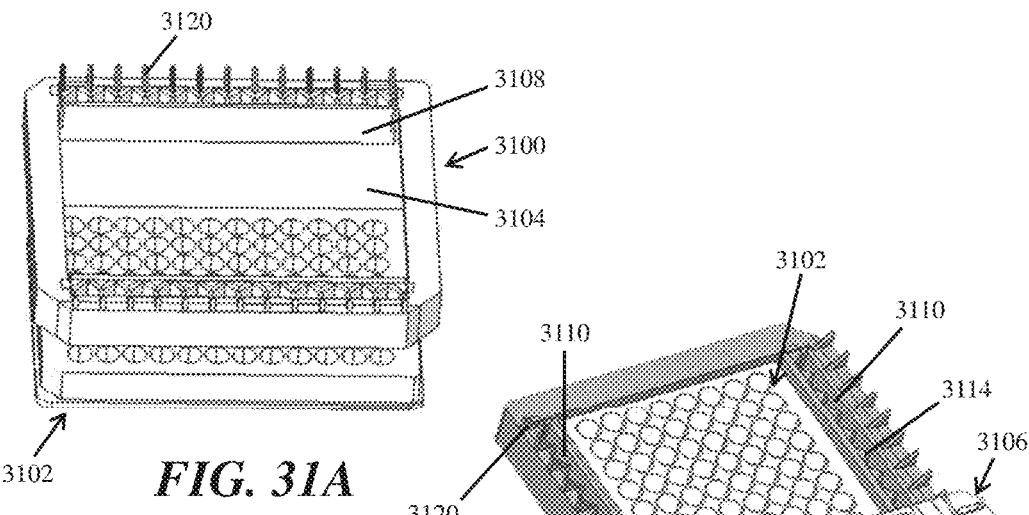
FIG. 31A shows a perspective view of a 96-well plate and adaptor.
Figure 31B:
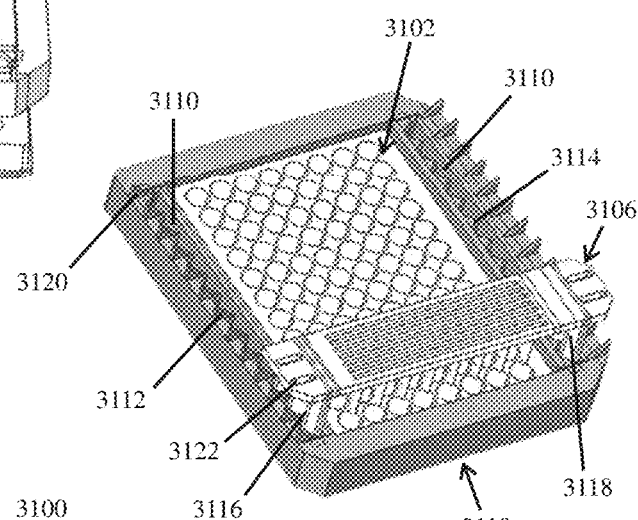
FIGS. 31B-31C show perspective views of a reagent loading device being inserted into the plate and adaptor of FIG. 31A.
Figure 31C:
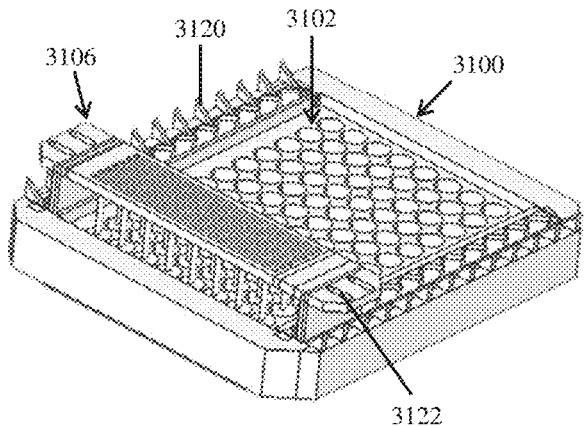
Figure 31D:
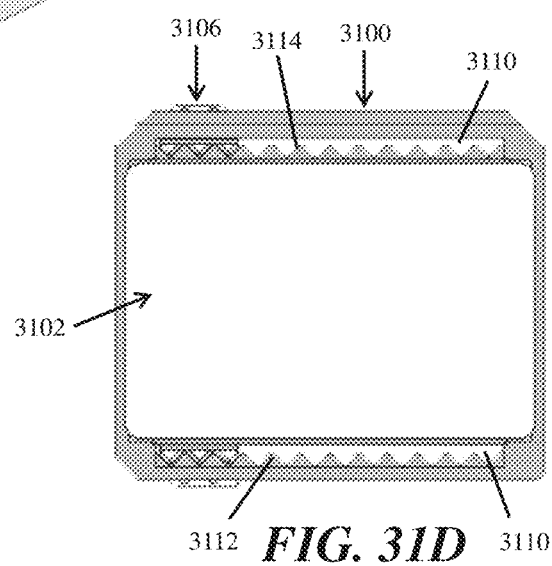
FIG. 31D shows a bottom view of the reagent loading device inserted into the plate and adaptor.

It should be appreciated that keys need not be part of an adaptor; in some variations, they may be integral to a receiving device such as a multi-well separation device, as shown in the variation of FIGS. 29 and 30A-30B. As shown there, the boundary wall of the multi-well separation 2902 device may comprise keys 2904 and 2906 on opposite sides of the outer surface of the boundary wall. These keys may have similar features and function similarly to those described with respect to FIGS. 27 and 28A-28C, and may interface with a reagent loading device 2908. Inward-facing keys, such as those shown in FIGS. 22A-22B through 26A-26B, may also be integral to a multi-well separation device. Furthermore, while the orientation keys described here are described with respect to the multi-well separation devices and reagent loading devices described herein, it should be appreciated that the orientation keys may also be used with standard multi-well plates not having the features described herein.

Another variation of an adaptor 3100 is shown in FIGS. 31A-31D. In the variation shown there, the adaptor 3100 may be configured to interface with a receiving device having fixed walls, such as a standard 96-well plate 3102, as shown. The adaptor 3100 may adapt a standard, fixed-well plate such that it may interface with a reagent loading device 3106. The adaptor 3100 may comprise inner walls 3108 having a central opening 3104 corresponding to the outer shape of the 96-well plate 3102, and slots 3110 configured to receive the reagent loading device 3106. The adaptor 3100 may comprise one or more orientation features to dictate the orientation of an inserted reagent loading device 3106. For example, the slots 3110 may comprise one or more a sawtoothed or zigzag surface configured to match a corresponding surface on the reagent loading device 3106 only when the reagent loading device 3106 is loaded in a particular orientation. As shown in FIGS. 31A-31D, the adaptor 3100 may comprise a sawtoothed surface 3112 on the outer wall of the slot 3110 on a first side, and a sawtoothed surface 3114 on the inner wall of the slot 3110 on a second side. The reagent loading device 3106 may have a sawtoothed surface 3116 on the outside of a first sidewall, which may correspond to sawtoothed surface 3112, while the reagent loading device 3106 may have a sawtoothed surface 3118 on the inside of a second sidewall, which may correspond to sawtoothed surface 3114. As such the reagent loading device 3106 may be able to be inserted into the slots 3110 of the adaptor 3100 when the reagent loading device 3106 is in a first orientation such that sawtoothed surface 3112 is aligned with sawtoothed surface 3116, and when sawtoothed surface 3114 is aligned with sawtoothed surface 3118. However, the reagent loading device 3106 may not be able to be inserted into the slots 3110 of the adaptor 3100 when the reagent loading device 3106 is in a second opposite orientation.

In some variations, the adaptor may further comprise other features to help guide the reagent loading device into the receiving wells. For example, in the variation shown in FIGS. 31A-31D, the adaptor 3100 may comprise pins 3120 that extend proximally from the proximal face of the adaptor 3100. The pins 3120 may be configured to fit into corresponding openings 3122 in the reagent loading device. While the pins 3120 are shown as having a triangular shape in FIGS. 31A-31D, the pins may have any suitable shape, such as rods, square, or the like.

Reagent/Test Agent

Each of the closed tips of the reagent loading device described herein may be loaded with a reagent or test agent. The reagent may be in any suitable form, such as but not limited to a liquid, a solution, a gel, or a solid. When the reagent is in a liquid or solution form, the reagent may adhere to each closed tip due to cohesive forces within the liquid (i.e., surface tension) and adhesive forces between the liquid and the closed tip. The volume of the liquid or solution that may adhere to each closed tip may in some variations be about 1 pL to about 10 pL, about 10 pL to about 100 pL, about 100 pL to about 1 nL, about 1 nL to about 10 nL, about 10 nL to about 100 nL, about 100 nL to about 1 µL, about 1 µL to about 10 µL, or more than about 10 µL, depending on the configuration and material of the closed tips and the material properties of the liquid or solution.

While in some variations the closed tips described herein may be loaded with the same reagent, it may often be desirable to load the closed tips with different reagents or test agents. For example, it may be desirable to do so in order that the wells of a receiving device (such as the separation wells of the multi-well separation devices described herein) may be subject to different reagents. The test agents may be, but are not limited to proteins, nucleic acids, cells, microorganisms (e.g., bacteria, fungi), plants (e.g., algae), viruses, small molecule drugs or any chemical compounds. In some variations, the closed tips may be loaded with a particular library of reagents desired to be tested. For example, the reagent loading device may be loaded with a bacterial library, a drug library (e.g., a kinase inhibitor library), an antibody library, or the like.

Mixing

The reagent loading devices described herein may optionally be configured to promote mixing of the reagent after being delivered (e.g., after being delivered into the contents of the separation wells of the multi-well separation devices described herein, or after being delivered to wells of a plate having fixed walls, such as a multi-well plate). In some variations, the reagent loading device may be configured to impart vibrations to promote mixing. The reagent loading device may comprise one or more actuators or motors that may cause the protrusions to vibrate. In some variations, each protrusion may be attached to an actuator or motor; in other variations, a single actuator or motor may cause all of the protrusions to vibrate. In yet other variations, there may be more than one actuator or motor but fewer than the number of protrusions.

Figure 20A:
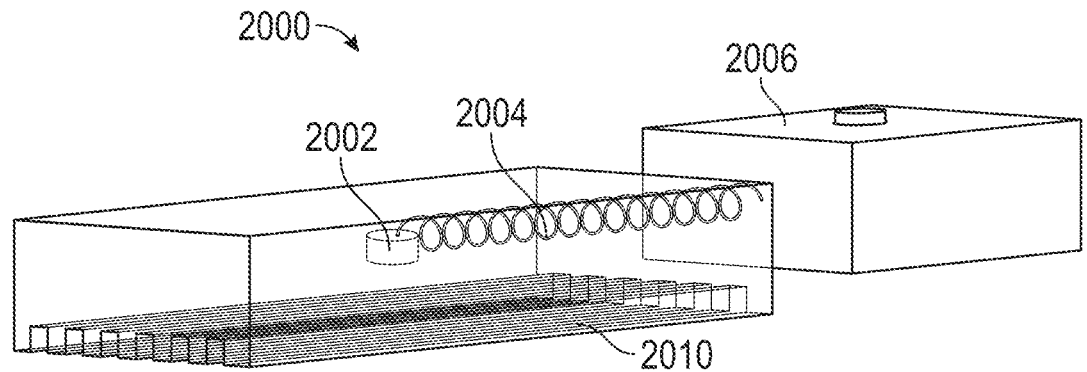
FIG. 20A is a perspective view of a motor unit.
Figure 20B:
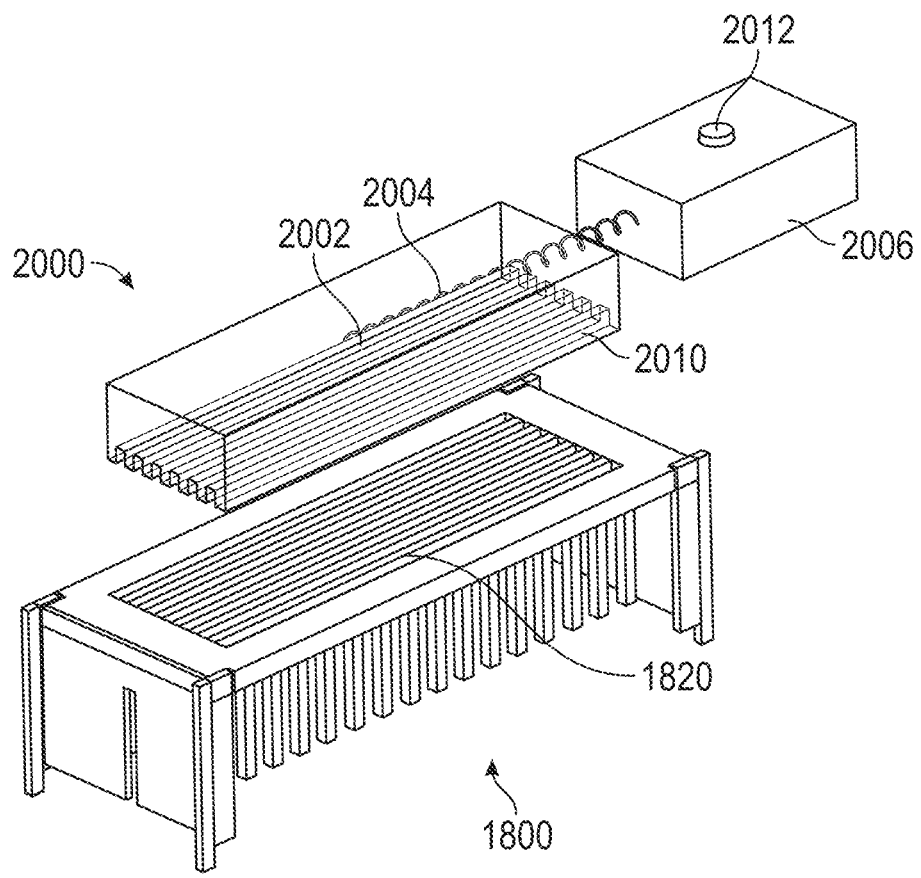
FIG. 20B is a perspective view of the motor unit of FIG. 20A with the reagent delivery device of FIG. 18.
Figure 20C:
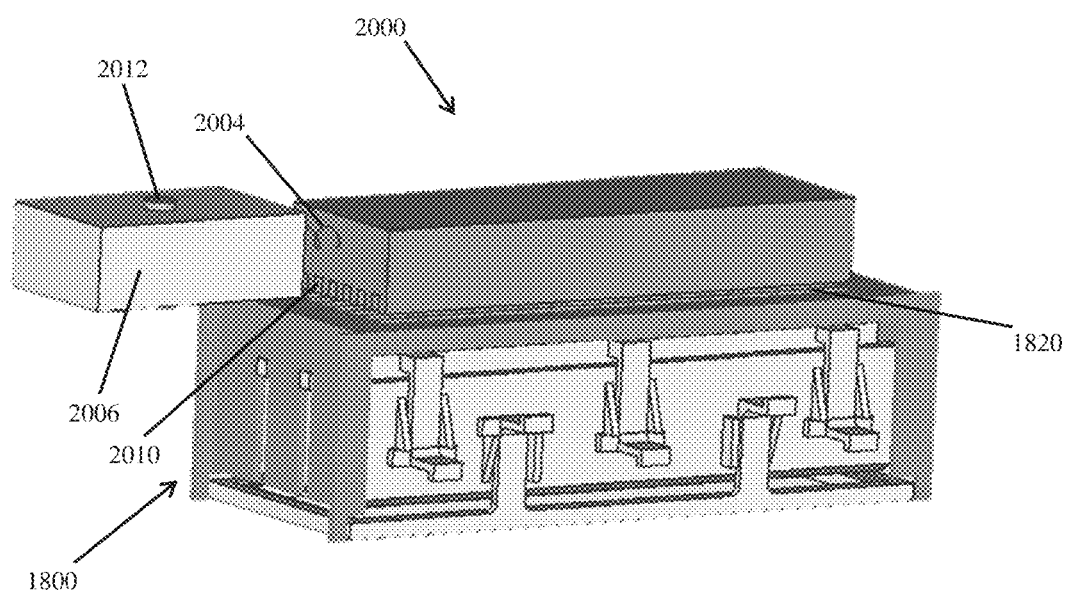
FIG. 20C is a perspective view of the motor unit of FIG. 20A with the reagent delivery device of FIG. 18 and a multi-well separation device, respectively.

FIGS. 20A-20C show one embodiment of a motor unit 2000. The motor unit 2000 may comprise a vibrational motor 2002, which may be connected via a wire 2004 to a controller 2006. The controller 2006 may be handheld and comprise an interface allowing the user to control the motor 2002, such as an on/off button 2012. In some variations, the interface may allow the user to control the frequency, magnitude, and/or duration of the vibration. The vibrational motor 2002 may be contained within a unit 2008 configured to interface with a reagent loading device in such a way as to transfer the vibrational motion of the motor 2002 to the protrusions of the reagent loading device. In the variation shown in FIGS. 20A-20C, the unit 2008 may comprise grooves 2010, which may interface with grooves 1820 on the proximal surface of plate 1808 of reagent loading device 1800, as shown in FIG. 20C. The unit 2008 may be secured to the reagent loading device (e.g., with grooves 2010 aligned with grooves 1820 of reagent loading device 1800) via any suitable reversible or irreversible method, such as but not limited to a spring loaded clamp or clipping. Although the variation shown in FIGS. 20A-20C comprises one vibrational motor 2002, it should be appreciated that in other variations the motor unit 2000 may comprise more than one motor, such as two, three, or more motors.

Figure 32:
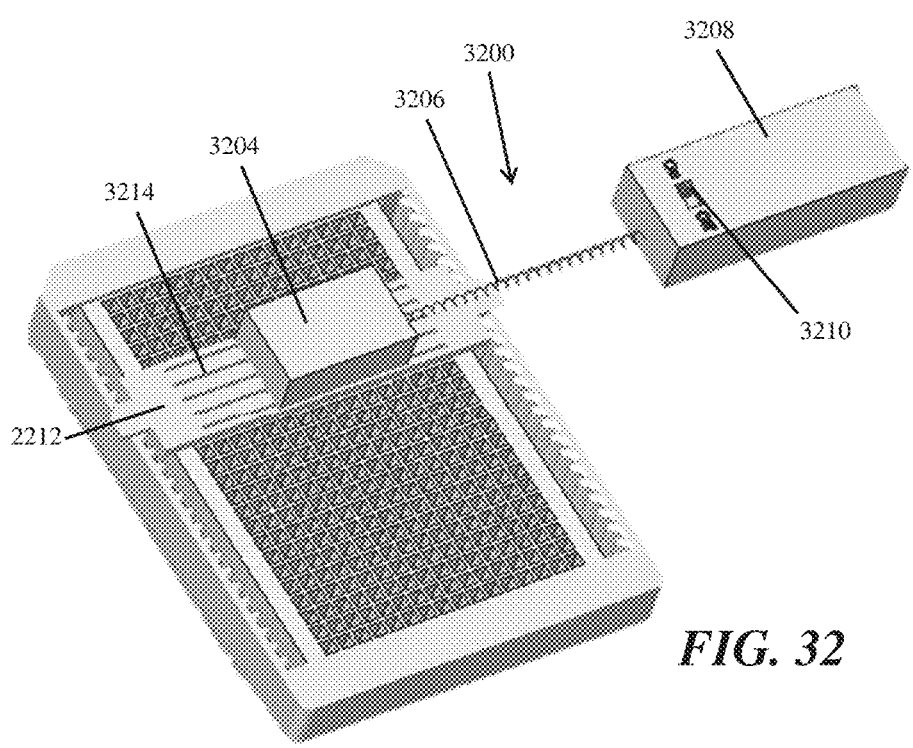
FIG. 32 shows a perspective view of another motor unit with the reagent delivery device and multi-well separation device and adapter of FIGS. 22 through 25A-25B.
Figure 33A:
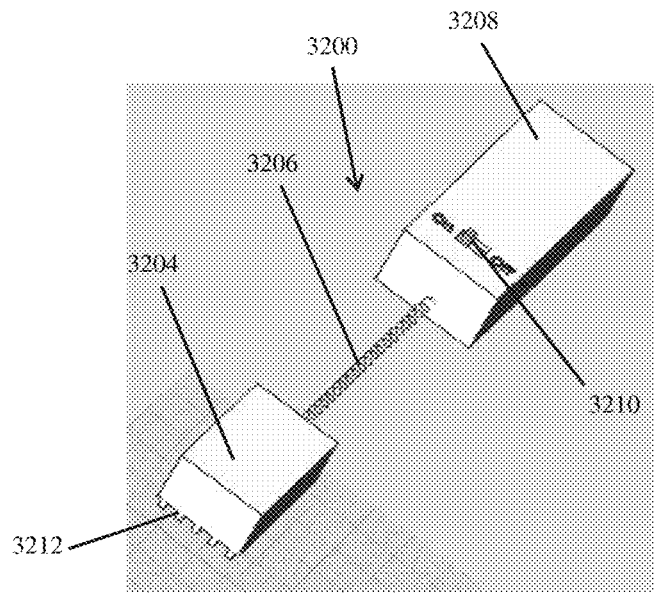
FIGS. 33A-33B show perspective view of the motor unit without the reagent delivery device and multi-well separation device and adapter.
Figure 33B:
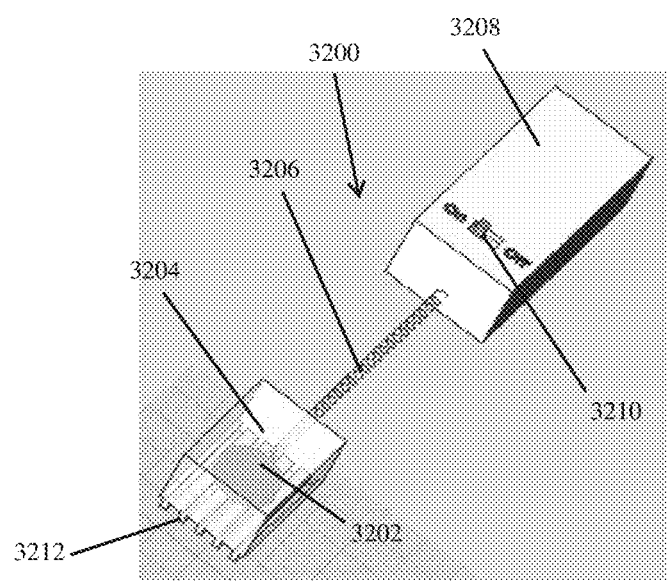

Another variation of a motor unit 3200 is shown in FIGS. 32 and 33A-33B. The motor unit 3200 may comprise a vibrational motor 3202 (see FIG. 33B) located within a vibration unit 3204, which may be connected via a flexible wire 3206 to a controller 3208 comprising a battery and an on/off switch 3210. The vibration unit 3204 may comprise grooves 3212 configured to interface with corresponding grooves 3214 on the proximal surface of the reagent loading device (e.g., any other the reagent loading devices described herein, such as reagent loading device 2212).

In another variation of a motor unit, one or more (e.g., two, three, or more) vibration motors may be mounted on the tip of a handheld device. The handheld device may be similar to a handheld pipette. The handheld device may be reversibly secured to a reagent loading device, for example by being secured to the proximal surface of the reagent loading device, such that when the handheld device is secured to the reagent loading device, vibration of the vibration motors may be transferred to the protrusions of the reagent loading device. In some variations, the handheld device may be secured to the reagent loading device via a clamp, which may be opened and closed via a button on the handheld device. In some variations, the button may be operated by the user's thumb. In some of these variations, the one or more motors may induce linear vibration. In other variations, the vibrations may be due to a magnetic field. More particularly, all or a portion of the protrusions of the reagent loading device, such as the tips may comprise a material attracted by a magnetic field (e.g., iron or nickel), and an alternating magnetic field may be turned on and off (e.g., at a frequency of about 10 Hz to about 200 kHz) in order to cause vibrations.

The magnitude and the frequency of the vibrations may be selected to maximize mixing of the reagent without negatively impacting the composition into which the reagent is delivered. That is, it may be desirable for the vibrations to maximize mixing into the contents of the wells (e.g., the separation wells of a multi-well separation device described herein, or the wells of a plate having fixed walls) without negatively impacting the target agent. As such, the magnitude and frequency of the vibrations may be tailored based on the design of the reagent loading device, including the physical design of the protrusions. In some variations, the vibrations may be linear vibration (e.g., back and forth vibration); in some other variations, the vibrations may be rotational vibrations. In some variations in which the vibrations are linear, the magnitude of the vibrations may be about 1 mm to about 3 mm. In some variations, the frequency may be about 10 Hz to about 200 kHz. In some of these variations, the frequency may be in the form of agitation below the acoustic range (i.e., below about 200 Hz); or it may be in in the form of sonication in the acoustic range (i.e., about 20 Hz to about 200 kHz) or ultrasonication in the ultrasonic range (i.e., above about 200 kHz). In some variations in which the vibrations are rotational vibrations, the vibrations may be at about 600 to about 12,000,000 rotations per minute. In variations in which the reagent loading device is configured to promote mixing of the reagent, the physical design of the protrusions may be configured to promote mixing. For example, the protrusions may comprise a stem having greater flexibility to promote vibration of the closed tip, such as by having a smaller cross-section or by comprising a flexible material.

Containment Element

In some variations, the reagent loading device may further comprise a containment element. The containment element may be configured to protect the reagents loaded on the closed tips of the reagent loading device, while also being configured such that that it can be removed from the reagent loading device while leaving the reagents on the closed tips of the protrusions. In some variations, the containment element may comprise a substantially planar surface. In these variations, when the containment element is placed in a position in which it protects the reagents on the closed tips, it may be in contact with the reagents. However, when the containment element is removed from the rest of the reagent loading device, the material of the containment element may have properties (e.g., a binding or surface affinity coefficient) such that when the surface is moved away from the reagents, the reagents release from the surface and remain attached to the closed tips of the protrusions.

For example, in one variation the closed tips of the reagent loading device may comprise a first plastic and the containment element may comprise a second plastic, wherein the binding or surface affinity coefficients are different and are such that the reagent releases from the second plastic and remains coupled to the first plastic. In other variations, the containment element may comprise a plurality of individual wells or caps, each configured to isolate an individual protrusion of the reagent loading device. The wells or caps may be connected (e.g., by each being connected to a planar surface), or they may be separate. The wells or caps may in some variations have a depth greater than the length of the protrusions on the reagent loading device, such that the closed tips of the protrusions may not come into contact with the end of the wells or caps; in other variations, the material of the wells or caps and closed tips may have material properties that allow the reagents to release from the surface of the wells or caps while remaining attached to the closed tips of the protrusions, as described above.

In another variation, the reagent loading device may have a design configured to protect the reagents loaded on the closed tips of the reagent loading device without a separate containment element. One such variation is shown in FIG. 18. As shown there, the reagent loading device 1800 may comprise legs 1822, which may be configured to protect the closed tips 1806. In variations in which the reagent loading device is rectangular, such as reagent loading device 1800, the legs 1822 may be located on each corner of the reagent loading device. The legs 1822 may be longer than the protrusions 1802 (i.e., they may extend distally beyond the closed tips 1806), such that if the reagent loading device is 1800 is placed on a surface with the closed tips 1806 of the protrusions facing the surface, the distal ends of the legs 1822 may contact the surface, while the closed tips 1806 may be suspended above the surface, as shown in FIG. 18. As such, the legs 1822 may protect the reagents loaded on the closed tips 1806 from touching the surface, which may protect the reagents from contamination.

Kits

It should be appreciated that the components of the multi-well separation devices and reagent loading devices described herein may, in addition to having the form of devices, have the form of kits for biological or chemical assays. Described herein are additionally systems for assays comprising both a multi-well separation device described herein (e.g., multi-well separation device 100 described above) and a reagent loading device described herein (e.g., reagent loading device 1000 or reagent loading device 1800 described above). The reagent loading device may comprise a plurality of protrusions corresponding to a plurality of separation wells of the multi-well separation device, such that each of the plurality of protrusions of the reagent loading device may be configured to simultaneously fit within the one of the separation wells of the multi-well separation device.

The system may further optionally comprise a chamber configured for loading the reagent loading device. The chamber may comprise isolated areas comprising the reagents or test agents in a configuration corresponding to the configuration of the closed tips of the reagent loading device. This may allow each tip of the reagent loading device to be simultaneously loaded with reagent or test agent, even when the reagents or test agents to be loaded on one or more of the closed tips are different. In some variations, the isolated areas may be a plurality of wells or compartments in a chamber, which may be loaded by the user with reagents or test agents (or may come pre-loaded with reagents or test agents) corresponding to the configuration of the closed tips. In other variations, the isolated areas may comprise a plurality of areas on a substrate (e.g., spots on a glass slide). In addition, the systems or kits described herein may in some instances comprise a subset of the devices described herein. For example, in one variation a kit may not comprise a multi-well separation device but may comprise a reagent loading device and a chamber configured for loading the reagent loading device.

Methods

Also described herein are methods of using the multi-well separation devices and reagent loading devices or kits, or systems, described here. Generally, a holding cavity (e.g., holding cavity 450 described above) may be formed by coupling a boundary wall (e.g., boundary wall 202 described above) to a substrate holder (e.g., substrate holder 402 described above), which may also sandwich a substrate (e.g., substrate 302 described above) and boundary seal (e.g., boundary seal 204 described above) between the boundary wall and the substrate holder. Once the holding cavity is formed, a composition (e.g., a cell suspension) may be delivered to the holding cavity (e.g., by using a pipette). A separation well structure (e.g., separation well structure 602 described above) may then be coupled within the holding cavity, which may divide the contents of the holding cavity into a plurality of separation wells (e.g., separation wells 610 described above). In some variations, a period of time may be allowed before coupling of the separation well structure, but it need not be. A period of time sufficient for the target agent to settle and/or attach to the substrate may be allowed after the coupling of the separation well structure, but need not be. A reagent loading device (e.g., the reagent loading device 1000 or 1800 described above) may then be used to deliver a test agent to each of separation wells either simultaneously or separately. Alternatively, test agents may be delivered to each of the separation wells using known methods, instead of a reagent loading device described here. The separation well structure may then optionally be removed from the holding cavity. Known techniques may be used to observe, measure, or analyze the assay.

Referring to the embodiment of the multi-well separation device 100, the multi-well separation device 100 may be assembled by placing the substrate 302 into the frame 404 of the substrate holder 402. The boundary wall clips 408 of the substrate holder 402 may be inserted into the substrate holder locks 210 of the locking strip 208 of the boundary wall 202. In order to do so, the tabs 412 of the boundary wall clips 408 may be flexed inward to allow the tabs 412 to travel through the openings of the substrate holder locks 210. The triangular shape of the tabs 412 may cause the tabs 412 to gradually flex inward from the pressure from the locking strip 208 as the boundary wall 202 is moved distally relative to the substrate holder 402. When the tabs 412 reach the proximal end of the openings, they may snap outward to hook onto the locking strips 208, with the distal surfaces 414 of the boundary wall clips 408 pressing against the proximal surface of the locking strips 208, and the elongate portion 410 of the boundary wall clips 408 sitting within the openings of the boundary wall locks 210 between the boundary wall 202 and the locking strips 208. This may sandwich the substrate 302 (and boundary seal 204) between the boundary wall 202 and the substrate holder 402. The compression force between the boundary seal 204 and the substrate 302 due to the coupling of the boundary wall clips 408 and the substrate holder locks 210 may press the boundary seal 204 against the substrate 302, creating a leak-proof seal around the holding cavity 450.

A similar method may be used to assemble the holding cavity in other embodiments of multi-well separation devices described herein, such as the multi-well separation device 1300 described with respect to FIG. 13. In that embodiment, the holding cavity may be assembled by placing a substrate into the frame 1308 of the substrate holder 1304. The boundary wall clips 1310 of the substrate holder 1304 may be coupled with the substrate holder locks 1316 of the boundary wall 1302. In order to do so, the boundary wall 1302 may be moved from a position proximally separated from the substrate holder 1304 distally toward the substrate holder 1304, with the boundary wall clips 130 aligned with the substrate holder locks 1316. As the boundary wall 1302 and substrate holder 1304 are moved toward each other, the inner surface of the horizontal portion 1314 of the boundary wall clips 1310 may come into contact with the outer surface of the projections 1318 of the substrate holder locks 1316. This contact may generate pressure that may cause the boundary wall clips 1310 to flex outward. As the boundary wall clips 1310 continue to be moved proximally relative to the projections 1318, the boundary wall clips 1310 may flex increasingly outward in order to travel along the outer surface of the projections 1318, until the horizontal portion 1314 of the boundary wall clips 130 reaches the proximal end of the projections 1318, at which point the boundary wall clips 1310 may snap inward, which may couple the boundary wall 1302 and the substrate holder 1304 due to the interface between the distal surface of the horizontal portion 1314 of the boundary wall clips 1310 and the proximal surface of the projections 1318 of the substrate holder locks 1316. This may sandwich the substrate (and boundary seal) between the boundary wall 1302 and the substrate holder 1304. The compression force between the boundary seal and the substrate due to the coupling of the boundary wall clips 1310 and the substrate holder locks 1316 may press the boundary seal against the substrate, creating a leak-proof seal around the holding cavity.

In other variations of the methods described here, the holding cavity need not be assembled. For example, in the embodiment of the multi-well separation device 500 shown in FIG. 5, the boundary wall 504 is fixedly attached to the substrate 506. Thus, the boundary wall 504 and substrate 506 need not be coupled to form the holding cavity 502.

In some variations in which the proximal surface 304 of the substrate 302 comprises a coating, the substrate 302 may be pre-coated with the coating. In other variations, the substrate 302 may be coated with the coating before or after assembling the holding cavity 450. In variations having a coating and in which the separation seal 602 or concentrating well structure 702 is attached to the substrate 302, the substrate 302 may be coated with the coating before or after the separation seal 602 or concentrating well structure 702 is attached to the substrate 302.

The target agent may then be delivered to the holding cavity 450. In some variations, the target agent may comprise a cell type. In other variations, the target agent may comprise, for example, a protein, a nucleic acid, a microorganism (e.g., bacteria, fungi), a plant (e.g., algae), a virus, a small molecule drug or any a chemical compound, a polymer, an antigen, an antibody, a cell fragment, a cell-homogenous, DNA, or a peptide. The target agent may be delivered within any suitable composition, such as but not limited to a liquid or a solution (e.g., when the target agent is a cell type, the cells may be delivered within a cell suspension), a gel (e.g., a hydrogel or sol-gel), a powder, a solid, or the like. When the composition is a liquid or solution, the composition may be delivered to the holding cavity using a pipette or other known technique. A sufficient volume of the composition may be delivered so as to cover the base of the holding cavity. After the target agent is delivered to the holding cavity 450, an appropriate amount of time may optionally be allowed for the target agent to settle and/or adhere to the substrate, but need not be. For example, when the target agent is a cell, in some variations an appropriate time need not be allowed before the separation well structure is inserted (described below).

The separation well structure 602 may then be inserted into the holding cavity 450. The separation well clips 614 of the separation well structure 602 may be inserted into the separation well locks 212 of the locking strip 208 of the boundary wall 202. In order to do so, the separation well structure 602 may be held above the holding cavity 450 such that the distal surfaces of the separation walls 604 are substantially parallel to the proximal surface 304 of the substrate 302. The separation well structure 602 may then be lowered into the holding cavity 450, maintaining a parallel orientation between the separation well structure 602 and the substrate 302. The separation well clips 614 may be inserted through the separation well locks 202. In order to do so, the tabs 618 of the separation well clips 614 may be flexed inward to allow the tabs 618 to travel through the openings of the separation well locks 202. The triangular shape of the tabs 618 may cause the tabs 618 to gradually flex inward from the pressure from the locking strip 208 as the separation well structure 602 is lowered into the holding cavity 450. When the tabs 618 reach the distal end of the opening, they may snap outward to hook onto the locking strips 208, with the proximal surface 620 of the tabs pressing against the distal surface of the locking strips 208, and the elongate portion 616 of the separation well clips 614 sitting within the openings of the separation well locks 212 between the boundary wall 202 and the locking strips 208.

This may secure the separation well structure 602 (and separation seal 608) within the holding cavity 450. This may form a plurality of separation wells 610, and compressive force between the separation seal 608 and the substrate 302 due to the coupling of the separation well clips 614 and separation well locks 212 may press the separation seal 608 against the substrate 302, creating leak-proof seals between the separation wells 610. The coupling of the separation well structure 602 within the holding cavity 450 may cause the composition within the holding cavity 450 to be distributed into the separation wells 610. In some variations, a second (or third, fourth, fifth, and so on) separation well structure, as described above, may further be coupled within one of the separation wells 610 formed by the separation well structure 602. In some variations, the target agents within each separation well 610 may then optionally be permitted to attach and/or grow for a desired period of time. For example, when the target agent is a cell, in some variations an appropriate time may be permitted for the cells to attach to the substrate 302 in each individual well 610.

A similar method may be used to secure the separation well structure within the holding cavity in other embodiments of multi-well separation devices described here, such as the multi-well separation device 1300 described with respect to FIG. 13. In that embodiment, the separation well structure 1306 may be coupled to the holding cavity by coupling the separation well locks 1330 with the separation well clips 1322. In order to do so, the separation well structure 1306 may be held above the holding cavity such that the distal surfaces of the separation walls 1334 are substantially parallel to the proximal surface of the substrate. The separation well structure 1306 may then be lowered into the holding cavity, maintaining a parallel orientation between the separation well structure 1306 and the substrate. As the separation well structure 1306 is lowered, the separation well clips 1322 may come into contact with the outer surface of the projections 1332 of the separation well locks 1330. This contact may generate pressure that may cause the separation well clips 1322 to flex outward. As the separation well clips 1322 continued to be moved distally relative to the projections 1332, the separation well clips 1322 may flex increasingly outward in order to travel along the outer surface of the projections 1332, until the horizontal portion 1326 of the separation well clips 1322 reaches the distal end of the projections 1332, at which point the separation well clips 1322 may snap inward, with the proximal surface of the horizontal portion 1326 of the separation well clips 1322 pressing against the distal surface of the projections 1332 of the separation well locks 1330. This may secure the separation well structure 1306 (and a separation seal) within the holding cavity, which may form a plurality of separation wells, as described above with respect to multi-well separation device 100.

A similar method may be used to secure the separation well structure within the holding cavity the embodiment of the separation well clips and separation well locks described with respect to FIGS. 14A-14B. In that embodiment, the separation well structure 1402 may be coupled to the holding cavity by coupling the separation well locks 1412 with the separation well clips 1404. In order to do so, the separation well structure 1402 may be held above the holding cavity such that the distal surfaces of the separation walls are substantially parallel to the proximal surface of the substrate, with the separation well clips 1404 in the first position, as described above. The separation well structure 1402 may then be lowered into the holding cavity, maintaining a parallel orientation between the separation well structure 1402 and the substrate. When the separation well structure 1402 is fully lowered into the holding cavity, the separation well clips 1404 may be moved to the second position, as described above, with the bar 1418 located below the first projection 1414 and the vertical portion 1410 held in place by the L-shape of the second projection 1416 of the separation well lock 1412, such that the distal surface of the bar 1418 is pressed against the proximal surface of the first projection 1414. As the separation well clips 1404 are moved to the second position, the second projection 1416 may flex to allow the separation well clips 1404 to enter the second position; once the separation well clips 1404 are in the second position, the second projection 1416 may return to the position shown in FIGS. 14A-14B. This may secure the separation well structure 1402 (and a separation seal) within the holding cavity, which may form a plurality of separation wells, as described above with respect to multi-well separation device 100.

A similar method may be used to secure the separation well structure within the holding cavity the embodiment of the separation well clips and separation well locks described with respect to FIGS. 15A-15B. In that embodiment, the separation well structure 1502 may be coupled to the holding cavity by coupling the separation well locks 1508 with the separation well clips 1506. In order to do so, the separation well structure 1502 may be held above the holding cavity such that the distal surfaces of the separation walls are substantially parallel to the proximal surface of the substrate, with the separation well clips 1506 in the first position, as described above. The separation well structure 1502 may then be lowered into the holding cavity, maintaining a parallel orientation between the separation well structure 1502 and the substrate. As the separation well structure 1502 is lowered into the holding cavity, the separation well clips 1506 may be pressed into the second position (shown in FIG. 15B) by the separation well locks 1508. This may be because in some variations, the hook 1514 and separation well locks 1508 may have correspondingly angled surfaces on their proximal and distal surfaces, respectively. In such variations, as the proximal surface of the hook 1514 comes into contact with the distal surface of the separation well lock 1508, the separation well clip 1506 may be increasingly pressed toward the second position, until the separation well clip 1506 snaps inward toward the first position. When the separation well structure 1502 is fully lowered into the holding cavity, the separation well clips 1506 return (e.g., due to bias) to the first position (shown in FIG. 15A), as described above, with the distal surface of the hook 1514 pressed against the proximal surface of the bar of the separation well lock 1508. When the separation well clip 1506 is in the second position, this may secure the separation well structure 1502 (and a separation seal) within the holding cavity, which may form a plurality of separation wells, as described above with respect to multi-well separation device 100.

A reagent or test agent may then be delivered to each of the separation wells in accordance with the desired screening operation or other laboratory test. In some variations, a reagent or test agent may be delivered to each of the separation wells individually using a manual (e.g., pipette) or robotic process. In other variations, a reagent loading device described herein (e.g., reagent loading device 1000 or reagent loading device 1800 described above) may be used to deliver the reagents or test agents substantially simultaneously into each individual well. The reagent delivery device may thus significantly increase the ease and throughput of manual operation. In some of these variations, the reagent loading device and/or multi-well separation device may be coupled with an automated robotic system to even further increase throughput. The resulting system may have a higher throughput and may be faster and simpler, in addition to other advantages, as compared to the current technology.

In some variations, the reagent loading device described herein may be pre-loaded with a reagent or test agent on each of the plurality of closed tips. In other variations, the user may load each of the plurality of closed tips with a reagent or test agent. When the reagent or test agent is in liquid or solution form, this may be done by dipping each of the closed tips into the liquid or solution, and then removing them from the liquid or solution. In some variations, the reagent loading device may be dipped into isolated areas comprising the reagents or test agents in a configuration corresponding to the configuration of the closed tips. This may allow each tip of the reagent loading device to be simultaneously loaded with reagent or test agent, even when the reagents or test agents to be loaded on one or more of the closed tips are different. In some variations, the isolated areas may be a plurality of wells or compartments in a chamber, which may be loaded by the user with reagents or test agents (or may come pre-loaded with reagents or test agents) corresponding to the configuration of the closed tips. In other variations, the isolated areas may comprise a plurality of areas on a substrate (e.g., spots on a glass slide). In other variations, one or more of the closed tips may be individually dipped into a liquid or solution to load the reagent or test agent. In some variations, a defined volume of liquid or solution may be applied to each closed tip. In some of these variations, the tip design may comprise a depression or other surface feature (e.g., a hemispherical depression, cylindrical recess, or one or more linear depressions, or a space between two parallel plates, or one or more capillaries, as described above with respect to FIGS. 12A-12H), which may be configured to hold a particular volume of a given reagent. For example, the depression or other surface design of the closed tips may have dimensions configured such that when the closed tip is dipped into the target solution, a defined volume is deposited or trapped at the closed tip, depending on the surface tension and surface affinity of the reagents (e.g., media, phosphate buffered saline, DMSO).

In instances when the reagent is in a solid (e.g., powder) form, the closed tips described herein may be loaded with the reagent in solution in the same manner as a reagent in a liquid or solution form, and the liquid in the solution may then be allowed to evaporate, leaving a solid reagent remaining on the closed tips. When the reagent is a cell or microorganism, in some variations the closed tips may be loaded with the cells or microorganisms by being loaded with droplets of suspensions containing the cells or microorganism in cryostorage solution in the same manner as a reagent in liquid or solution form, and the reagent loading device may then be frozen. It should be appreciated that not all closed tips need be loaded with a reagent (e.g., some closed tips may not be loaded with a reagent so as to provide a control condition).

In some instances, the closed tips described herein may be loaded with a gel, such as but not limited to a hydrogel or a sol-gel. In some cases, the closed tips may be directly loaded with a gel. In other cases, the closed tips may be loaded with a liquid, which may then be cured to form a gel (e.g., polymerization may be light-induced, chemically induced, thermally induced, or the like). In yet other cases, the closed tips may be loaded with a liquid, which may then at least partially evaporate to leave behind a gel. In some of these variations, the reagent or test agent may be in a gel form, while in other variations the reagent or test agent may be incorporated into a gel (i.e., the gel may immobilize the reagent or test agent). In these variations, non-limiting examples of the reagent or test agent may comprise proteins, nucleic acids, cells, microorganisms (e.g., bacteria, fungi), plants (e.g., algae), viruses, small molecule drugs or any chemical compounds, or a particular library of reagents desired to be tested (e.g., a bacterial library, a drug library (e.g., a kinase inhibitor library), an antibody library, a virus library, a gene library, a polymer library, a peptide library, a cell library, or the like).

The loaded reagent loading devices described herein (e.g. reagent loading device 1000 or reagent loading device 1800) may be lowered into the multi-well separation devices described herein (e.g., multi-well separation device 100) such that the protrusions (e.g., protrusions 1002 or protrusions 1802) of the reagent loading device enter the separation wells. In variations in which the system comprises an orientation feature, the orientation feature may be used to ensure that the reagent loading device is oriented properly, such that each protrusion of the reagent loading device enters the desired separation well. For example, in the variation shown in FIGS. 22A-22B through 26A-26B, the variation shown in FIGS. 27 and 28A-28C, and the variation shown in FIGS. 29 and 30A-30B, the notches of the reagent loading device may be aligned with the keys of the multi-well separation device or adaptor before lowering the reagent loading device into the multi-well separation device. In variations in which the reagent loading device is configured to correspond to orientation features on an adaptor, the adaptor may be placed over the multi-well separation device (or other receiving device) before the loaded reagent loading device is lowered into the wells.

The reagent loading device should be sufficiently lowered such that the reagents loaded on the closed tips are immersed in the contents of the separation wells. In some variations, such as the reagent loading device 1000, this sufficient amount of lowering may be reached by lowering the reagent loading device 1000 until the distal surface 1010 of the plate 1008 contacts the proximal surface of the multi-well separation device (e.g., multi-well separation device 100). In other variations, such as the reagent loading device 1800, this sufficient amount of lowering may be reached by lowering the reagent loading device 1800 until the distal surface of the legs 1822 reaches the substrate holder and/or the surface upon which the multi-well separation device is resting. Alternatively, it should be appreciated that the reagent loading device may be lowered such that the closed tips and/or reagents or test agents contact but do not penetrate the proximal surface of the contents of the separation well (e.g., in some variations in which the separation wells contain a gel or solid).

While the closed tips are immersed in the contents of the separation wells, the closed tips may be vibrated to promote mixing of the reagents with the contents of the separation wells. For example, in some variations in which the vibration is provided by motor unit 2000, the on/off button 2012 may be used to control the motor 2002. The motor 2002 may be turned on, which may cause the unit 2008 to vibrate, which may transfer vibrational motor to the reagent loading device 1800 via grooves 2010 on the motor unit 2000 interfaced with grooves 1820 of the reagent loading device 1800. As another example, in some variations in which the vibration is caused by a handheld device having a motor unit mounted on it, the handheld device may be secured to the reagent loading device (e.g., via a clamp). The user's thumb may be used to turn on the motor, which may cause linear or rotational vibration. As yet another example, in some variations in which the vibration is caused by a magnetic field, a magnetic field may be turned on and off (e.g., at a frequency of about 10 Hz to about 200 kHz) in order to cause vibrations.

It should also be appreciated that in other variations, a reagent loading device may be used to deliver one or more reagents or test agents to a holding cavity without use of a separation well structure. For example, the reagent loading device may be used to deliver one or more reagents or test agents to a holding cavity comprising a solid or gel coating. In this case, the coating may sufficiently limit migration or diffusion of the reagents or test agents, such that the reagent or test agent delivered by each protrusion of the reagent loading device remains sufficiently isolated from the others. The reagent loading device may be lowered onto the surface of the coating such that the closed tips and/or reagents or test agents contact the surface of the coating, but the closed tips do not penetrate the surface; or the reagent loading device may be lowered onto the surface such that the closed tips penetrate the surface. In some variations the reagent loading device may be removed after the reagents or test agents are transferred to the coating, or the reagent loading device may be left in place. In one specific non-limiting example, a reagent loading device may be used to deliver one or more antimicrobial agents to a gel (e.g., an agar gel) having a bacteria cultured on its surface or that will later have a bacteria cultured on its surface.

After the reagents are delivered to the separation wells, a sufficient period of time may be allowed to elapse such that any desired reactions may occur. The separation well structure may then be removed from the holding cavity (e.g., in multi-well separation device 100, separation well structure 602 may be removed from the holding cavity 450). This may allow a process to be carried out on the full contents of the holding cavity simultaneously, such as a washing step, treatment with a stain, reporter, or antibody, or the like. The solution may be removed (e.g., via aspiration) individually from each separation well before the separation well structure is removed, or it may be removed (e.g., via aspiration) from the holding cavity as a whole after the separation well structure is removed. In variations in which a second separation well structure (or third, fourth, fifth, or so on) is coupled within a separation well of the separation well structure, the second separation well structure may be removed with the separation well structure, or the second separation well structure may be removed while leaving the separation well structure coupled in the holding cavity, or the second separation well structure may be left coupled in the holding cavity while the separation well structure is removed (in variations in which the second separation well structure is coupled to the substrate in a way that allows it to remain coupled without the separation well structure (e.g., if the second separation well structure is coupled via a boundary wall)).

In some variations, after the separation well structure is removed, the same or a different separation well structure may be coupled within the holding cavity, in a similar manner as described above for the initial coupling of a separation well structure into the holding cavity. For example, a first process (e.g., delivery of one primary antibody from a library of primary antibodies to each of the separation wells) can be carried out with the composition in the holding cavity separated by a first separation well structure into a given number of separation wells. A second process (e.g., treatment with a drug of interest) can then be carried out with the first separation well structure removed and with the composition forming one continuous region in the holding cavity. A third process (e.g., delivery of one secondary antibody from a library of secondary antibodies corresponding to the library of primary antibodies to each of the separation wells) can then be carried out with the composition in the holding cavity re-separated by the first separation well structure recoupled into the holding cavity. As another example, for the third process, a different, second separation well structure can be coupled into the holding cavity to differently divide the composition within the holding cavity for the process.

After the assaying processes are carried out, the results may be analyzed using known techniques. In some varia-tions, a microscope mount adaptor specifically designed for the multi-well separation devices described herein may be used. The multi-well separation device and/or reagent loading device may be disposable, such that one or both are configured for a single use. Thus, after completion of the desired processes, one or both may be discarded. To the extent that the above steps are described with respect to multi-well separation device 100, it should be appreciated that the steps above may similarly be carried out using other multi-well separation devices having separate boundary walls and substrates (e.g., multi-well separation device 1300 shown in FIG. 13, or separation well clip and separation well lock designs shown in FIGS. 14A-14B and 15A-15B), or using a multi-well separation device having a fixedly attached or integrated boundary wall and substrate, such as the holding cavity 502 of the multi-well separation device 500 described above.

Furthermore, while the loading and use of the reagent loading devices described herein have been described above with respect to use in conjunction with a multi-well separation device as described herein, it should be appreciated that in some variations, the loading and use of the reagent loading devices described herein may be carried out separately from the use of any multi-well separation device. That is, the reagent loading devices may be used to deliver materials to receptacles other than those within a multi-well separation device described here. For example, the reagent loading devices may be used with plates having fixed walls (e.g., multi-well plates or a plate having a single well), with or without an adaptor, such as the adaptors described above. Conversely, the multi-well separation devices described herein may be used separately from the use of any reagent loading devices described herein. For example, devices or methods not using a reagent loading device described here may be used to deliver materials to individual wells of the multi-well separation devices described herein.

Specific details are given in the above description to provide a thorough understanding of the embodiments. However, it is understood that the embodiments may be practiced without these specific details. Those skilled in the art can readily recognize that numerous variations and substitutions may be made in the disclosed embodiments, their use and their configuration to achieve substantially the same results as achieved by the embodiments described herein. Accordingly, there is no intention to limit the claims to the disclosed exemplary forms. Many variations, modifications and alternative constructions fall within the scope and spirit of the disclosure as expressed in the claims.

Example #1

As one example, the methods described herein could be used to study a drug's pathway.

1. Cell Introduction: After coupling a boundary wall, substrate, and boundary seal to form a holding cavity, a cell suspension may be pipetted into the holding cavity.

2. Cell Separation: A separation well structure may then be coupled within the holding cavity to separate the cell suspension into isolated separation wells, separating cells in suspension into each well. The cell density or concentration may be pre-calculated, to achieve the desired number of cells and volume in each separation well. For example, if the number of the cells desired in each separation well is x, and the number of separation wells is y, and the desired volume in each separation well is z (in µL), then the cell density or concentration of the cell suspension should be x/z cells per microliter, and a total volume of y*z microliter should be pipetted into the holding cavity. The desired number of cells in each separation well x may be determined for the particular assay to be performed. For example, for a proliferation assay, x should be small enough to allow room for cells to proliferate after seeding and treatment. As another example, for a cell death assay, x should be large enough to sustain the assault from the treatment. The desired volume in each separation well z may be determined based on the practical conditions and the drug delivery concentration. For example, z may be chosen to be large enough to such that the solution will not significantly evaporate or dry. Additionally or alternatively, z may be chosen to be small enough such that after the separation well structure and reagent loading device are in position, the solution remains separated by the separation well structure (i.e., the solution does not flow over the walls of the separation well structure; the volume of the separation well accommodates the volume of composition in the well, as well as the volume of the protrusion of the reagent loading device inserted into the composition). The volume z may also be chosen to achieve a desired dilution: if the volume of the reagent or drug on a protrusion is m (in μL), and the desired dilution when the reagent or drug is delivered is a factor of n, then z may be equal to $m*(n-1)$.

3. Cell Attachment: The cells may then be allowed to attach to the substrate for a certain amount of time.

4. Combination: After the cells reach the desired condition, the separation well structure may then be removed, such that the holding cavity is continuous again (i.e., all cells in the cavity are in a common media).

5. Treatment: A testing condition may be imposed onto the cells. For example, a testing agent, such as a drug at a desired concentration, may be loaded into the holding cavity (i.e., the drug may be diluted into the media in the cavity). In other variations, the solution in the holding cavity may first be aspirated, and the solution may then be replaced by a drug solution (e.g., mixed in media) may be loaded into the pre-aspirated cavity. Alternatively, the testing condition may be imposed without removal of the separation well structure. For example, with the separation wells in place, the drug may be delivered with a reagent-loading device by loading each protrusion of the reagent loading device with the same drug. The reagent loading device may then be lowered into the holding cavity, such that one protrusion of the reagent loading device enters each of the separation wells, and the reagent-loaded tips of the protrusions are immersed into the solution in each separation well, but not touching the cells on the bottom. The protrusions may then be vibrated to promote mixing of the reagent with the cell suspension. The reagent loading device may then be removed from the multi-well separation device.

6. Preparation: After the testing condition matures, various markers of the cells can be screened. Cells may first be prepared for analysis: The media in the cavity may be aspirated. Excess media may be washed with phosphate buffered saline. Cells in the cavity may be fixed with formalin or paraformaldehyde solutions. The fixing solution may then be aspirated. The cells may then be washed with phosphate buffered saline, blocked by serum or albumin solutions, if necessary permeablized by Triton X-100, and then immersed in phosphate buffered saline.

7. Re-separation: The separation well structure may be recoupled within the holding cavity to re-separate the cells in the into the separation wells. (In the alternative variation in step 5 above, wherein the testing condition is imposed without removing the separation well structure, re-separation is not necessary.)

8. Analytic Agent Introduction: The analytic reagent library (e.g., primary antibody library) may then be delivered with a reagent-loaded device. In particular, a reagent loading device pre-loaded with a library of analytic agents, such as primary antibodies, may then be lowered into the holding cavity, such that one protrusion of the reagent loading device enters each of the separation wells, and the reagent-loaded tips of the protrusions are immersed into the solution in each separation well, but not touching the cells on the bottom. The protrusions may then be vibrated to promote mixing of the reagent with the cell suspension. The reagent loading device may then be removed from the multi-well separation device. Adequate time for incubation may be allowed so that the analytic agents such as primary antibodies may attach to their targets.

9. Re-combination: The separation well structure may be removed from the holding cavity, such that all cells are again in a common holding cavity. The solutions in each separation well may be individually aspirated before the separation well structure is removed; or the separation well structure may be removed before aspirating the solution from the holding cavity.

10. Detection Agent Introduction: After washing with phosphate buffered saline, the activity of the analytic agents, such as the primary antibody, may be analyzed. For example, if a non-conjugated primary antibody library is used, the phosphate buffered saline may be replaced with a secondary antibody. The identity of each analytic agent, such as the primary antibody, may be indicated by the position of each cell-aggregate formed by the separation wells. Instead of staining each different primary antibody with a different secondary antibody, one secondary antibody may be used to detect and distinguish unlimited number of primary antibodies. The analysis of steps 8 through 10 may be repeated, loading different primary and secondary antibodies each time.

Example #2

As another example, the methods described herein could be used for drug screening.

1. Cell Introduction: After coupling a boundary wall, substrate, and boundary seal to form a holding cavity, a cell suspension may be pipetted into the holding cavity. The cell density or concentration may be pre-calculated, to achieve the desired number of cells and volume in each separation well. For example, if the number of the cells desired in each separation well is x and the number of separation wells is y, and the desired volume in each separation well is z (in μL), then the cell density or concentration of the cell suspension should be x/z cells per microliter, and a total volume of y*z microliter should be pipetted into the holding cavity. The desired number of cells in each separation well x may be determined for the particular assay to be performed. For example, for a proliferation assay, x should be small enough to allow room for cells to proliferate after seeding and treatment. As another example, for a cell death assay, x should be large enough to sustain the assault from the treatment. The desired volume in each separation well z may be determined based on the practical conditions and the drug delivery concentration. For example, z may be chosen to be large enough to such that the solution will not significantly evaporate or dry, additionally or alternatively, z may be chosen to be small enough such that after the separation well structure and reagent loading device are in position, the solution remains separated by the separation well structure (i.e., the solution does not flow over the walls of the separation well structure; the volume of the separation well accommodates the volume of composition in the well, as well as the volume of the protrusion of the reagent loading device inserted into the composition). The volume z may also be chosen to achieve a desired dilution: if the volume of the reagent or drug on a protrusion is m (in µL), and the desired dilution when the reagent or drug is delivered is a factor of n, then z may be equal to m*(n−1).

2. Cell Separation: A separation well structure may then be coupled within the holding cavity to separate the cell suspension into isolated separation wells.

3. Cell Attachment: The cells may be allowed to settle to the base of the separation wells, and time may be allowed for the cells to adhere and grow.

4. Treatment: A reagent loading device pre-loaded with a library of drugs at a certain volume m (µL) on each protrusion may then be lowered into the holding cavity, such that one protrusion of the reagent loading device enters each of the separation wells. The volume z in each separation well, and/or the volume m, may be chosen to achieve a desired drug dilution: if the volume of the reagent or drug on a protrusion is m (in µL), and the desired dilution when the reagent or drug is delivered is a factor of n, then z may be equal to m*(n−1). The protrusions may then be vibrated to promote mixing of the drugs with the cell suspension. The reagent loading device may then be removed from the multi-well separation device.

5. Analysis: The effect of the drugs in each separation well may be analyzed through live cell analysis. Bright field images or videos of the cells in each well may be acquired. If the cells are intrinsically fluorescent (e.g., due to a GFP gene transfected into the cells' genome), fluorescent images of the cells may be acquired. Additionally or alternatively, the media in each separation well may be sampled for further testing.

The cells may also be further processed for analysis. For example, the cells may be washed, fixed and permeabilized, and an analytic reagent of interest, such as a primary antibody, may be introduced. After incubation and washing, a detection reagent, such as a secondary antibody, may be introduced. After incubation and washing, the cellular response to each drug may be analyzed based on the signals of the analytic reagents. If the separation well structure has been removed, the different drugs may be distinguished by the position of each cell-aggregate.

Various assays may be performed on the cells in the holding cavity after removal of the separation well structure. For example, in a staining assay, instead of processing and staining the cells in each separation well, all the cells in the boundary well may be processed and stained at once, without the need for a robotic liquid handler or a multi-channel pipette. In a fluorescent assay, the fluorescent signals from the cells may be acquired. The effects of each drug may be distinguished easily by the distinct spatial separation between each cell-aggregate due to the separation wells structure.

Example #3

As another example, the methods described herein could be used to for assessing the efficacy of a drug on multiple cell types from an individual (e.g., a patient).

1. Drug Loading: After coupling a boundary wall, substrate, and boundary seal to form a holding cavity, a composition comprising a drug may be pipetted into the holding cavity.

2. Separation: A separation well structure may then be coupled within the holding cavity to separate the composition into isolated separation wells.

3. Cell Introduction: A reagent loading device pre-loaded with a library of cells from an individual may then be lowered into the holding cavity, such that one protrusion of the reagent loading device enters each of the separation wells. The protrusions may then be vibrated to promote mixing of the cells with the composition comprising the drug. The reagent loading device may then be removed from the multi-well separation device.

4. Analysis: The effect of the drug on the cells in each separation well may be analyzed through live cell analysis. Bright field images or videos of the cells in each well may be acquired. If the cells are intrinsically fluorescent (e.g., due to a GFP gene transfected into the cells' genome), fluorescent images of the cells may be acquired. Additionally or alternatively, the media in each separation well may be sampled for further testing.

To observe the specific activities of the cells in response to the drug, the media in each well may be aspirated, and then the separation well structure may be removed from the holding cavity; or, the separation well structure may be removed from the holding cavity and then the media aspirated. Various assays may be performed on the cells in the holding cavity. For example, in a staining assay, instead of processing and staining the cells in each separation well, all the cells in the holding cavity may be processed and stained at once, without the need for a robotic liquid handler or a multi-channel pipette. In a fluorescent assay, the fluorescent signals from the cells may be acquired. The effects of the drug on multiple cell types from the individual may be distinguished easily by the distinct spatial separation between each cell-aggregate due to the separation wells structure.

Example #4

As another example, the methods described herein could be used to for parallel analysis of drug efficacy for a plurality of individuals (e.g., patients).

1. Drug Loading: After coupling a boundary wall, substrate, and boundary seal to form a holding cavity, a composition comprising a drug may be pipetted into the holding cavity.

2. Separation: A separation well structure may then be coupled within the holding cavity to separate the composition into isolated separation wells.

3. Cell Introduction: A reagent loading device pre-loaded with a library of cells from different individuals may then be lowered into the holding cavity, such that one protrusion of the reagent loading device enters each of the separation wells. The protrusions may then be vibrated to promote mixing of the cells with the composition comprising the drug. The reagent loading device may then be removed from the multi-well separation device.

4. Analysis: The effect of the drug on the cells in each separation well may be analyzed through live cell analysis. Bright field images or videos of the cells in each well may be acquired. If the cells are intrinsically fluorescent (e.g., due to a GFP gene transfected into the cells' genome), fluorescent images of the cells may be acquired. Additionally or alternatively, the media in each separation well may be sampled for further testing.

To observe the specific activities of the cells in response to the drug, the media in each well may be aspirated, and then the separation well structure may be removed from the holding cavity; or, the separation well structure may be removed from the holding cavity and then the media aspirated. Various assays may be performed on the cells in the holding cavity. For example, in a staining assay, instead of processing and staining the cells in each separation well, all the cells in the holding cavity may be processed and stained at once, without the need for a robotic liquid handler or a multi-channel pipette. In a fluorescent assay, the fluorescent signals from the cells may be acquired. The effects of the drug on the cells of different individuals may be distinguished easily by the distinct spatial separation between each cell-aggregate due to the separation wells structure.

Example #5

As another example, the methods described herein could be used to for parallel analysis of drug efficacy for a plurality of individuals (e.g., patients).

1. Drug Introduction: After coupling a boundary wall, substrate, and boundary seal to form a holding cavity, a composition comprising a drug may be pipetted into the holding cavity.

2. Separation: A separation well structure may then be coupled within the holding cavity to separate the composition into isolated separation wells.

3. Cell Introduction: Cells from different individuals may then be delivered to each isolated separation well individually (e.g., using a pipette). The multi-well separation device may then be vibrated (e.g., by placing it on a shaker) to promote mixing of the cells with the composition comprising the drug.

4. Analysis: The effect of the drug on the cells in each separation well may be analyzed through live cell analysis. Bright field images or videos of the cells in each well may be acquired. If the cells are intrinsically fluorescent (e.g., due to a GFP gene transfected into the cells' genome), fluorescent images of the cells may be acquired. Additionally or alternatively, the media in each separation well may be sampled for further testing.

To observe the specific activities of the cells in response to the drug, the media in each well may be aspirated, and then the separation well structure may be removed from the holding cavity; or, the separation well structure may be removed from the holding cavity and then the media aspirated. Various assays may be performed on the cells in the holding cavity. For example, in a staining assay, instead of processing and staining the cells in each separation well, all the cells in the boundary well may be processed and stained at once, without the need for a robotic liquid handler or a multi-channel pipette. In a fluorescent assay, the fluorescent signals from the cells may be acquired. The effects of the drug on the cells of different individuals may be distinguished easily by the distinct spatial separation between each cell-aggregate due to the separation wells structure.

Example #5

As another example, the methods described herein could be used for parallel analysis of reagent effects on a bacterial culture.

1. Bacterial Culture: A gel comprising bacterial culture medium, such as a hydrogel (e.g., agar gel) may be deposited into a cavity. The cavity may be a holding cavity of the separation well devices described herein, or it may be a cavity of a fixed-wall plate, or the like. The gel may be deposited while in a polymerized form, or a pre-gel solution may be deposited into the cavity and then cured to form a gel. Target agents, such as bacteria, may be cultured on the surface of the gel, or may be incorporated into the gel.

2. Treatment: A reagent loading device as described herein may be loaded with one or more test libraries of reagents, such as a protein library, a nucleic acid library, a cell library, a microorganism library (e.g., a bacterial library, a fungi library), a plant library (e.g., algae), a virus library, a library of small molecule drugs or any chemical compounds (e.g., a kinase inhibitor library), an antibody library, or the like, or any combination of these. Alternatively, the reagent loading device may be preloaded with the one or more test libraries. The reagents may be in a liquid form, a gel form, or a solid form, and/or may be immobilized onto the closed tips of the reagent delivery device, such as via a hydrogel or a sol-gel. The reagent loading device may be lowered into the cavity such that the closed tips of the reagent loading device make contact with the surface of the gel in the cavity. The reagent loading device may be left in place or may be removed.

3. Analysis: The effects of each reagent on the bacteria culture on the gel surface may be analyzed.

We claim:

1. A chemical or biological assay device, comprising:
a substrate;
a separation seal; and
a removable separation well structure,
wherein the removable separation well structure comprises a plurality of walls defining a plurality of openings,
wherein the separation seal forms a leak-proof seal between a proximal surface of the substrate and a distal surface of the removable separation well structure, and
wherein the substrate is coupled to the removable separation well structure via the separation seal to form a plurality of separation wells such that each separation well is isolated from other separation wells.

2. The device of claim 1, further comprising:
a boundary wall, wherein a distal surface of the boundary wall is coupled to the proximal surface of the substrate to form a holding cavity.

3. The device of claim 2, further comprising:
a boundary seal, wherein the boundary seal forms a leak-proof seal with the distal surface of the boundary wall and the proximal surface of the substrate,
wherein the boundary wall is coupled to the substrate via the boundary seal to form the holding cavity.

4. The device of claim 1, further comprising:
a concentrating well structure located between the substrate and the removable separation well structure,
wherein the concentrating well structure comprises a plurality of openings, wherein each of the plurality of openings of said concentrating well structure corresponds to one of the plurality of openings defined by the removable separation well structure,
and wherein each of the plurality of openings of said concentrating well structure has a proximal end cross-sectional area and a distal end cross-sectional area, and wherein the proximal end cross-sectional area is greater than the distal end cross-sectional area.

5. The device of claim 3, wherein the boundary seal is located between a substrate holder and the substrate.

6. A method of performing a chemical or biological assay using the device of claim 1, comprising:
i) applying a target agent to the substrate;
ii) coupling the removable separation well structure to the substrate to form the plurality of separation wells, thereby dividing the target agent into a plurality of subpopulations, each subpopulation in one of the plurality of separation wells; and iii) applying a plurality of test agents to the plurality of subpopulations, wherein the effects of the plurality of test agents on the target agent are analyzed.

7. The method of claim 6, wherein the target agent is cells in a cell suspension, and wherein the plurality of test agents is a plurality of drug.

8. The method of claim 7, wherein applying the plurality of drugs to the plurality of subpopulations comprises simultaneously applying the plurality of drugs to the plurality of subpopulations using a reagent loading device comprising a plurality of protrusions.

9. The method of claim 6, wherein the target agent is cells in a hydrogel, and wherein the plurality of test agents is a plurality of drugs.

10. The method of claim 9, wherein applying the plurality of drugs to the plurality of subpopulations comprises simultaneously applying the plurality of drugs to the plurality of subpopulations.

11. A method of performing a chemical or biological assay using the device of claim 1, comprising:
   i) applying a cell suspension comprising cells to the substrate;
   ii) coupling the removable separation well structure to the substrate to form the plurality of separation wells, thereby dividing the cells into a plurality of subpopulations, each subpopulation in one of the plurality of separation wells;
   iii) uncoupling the removable separation well structure from the substrate;
   iv) applying a drug to the substrate;
   v) recoupling the removable separation well structure to the substrate, thereby re-dividing the cells into the plurality of subpopulations; and
   vi) applying a plurality of primary antibodies to the plurality of subpopulations;
   vii) applying a plurality of secondary antibodies to the plurality of subpopulations.

12. The method of claim 11, wherein applying the plurality of primary antibodies to the plurality of subpopulations comprises simultaneously applying the plurality of primary antibodies to the plurality of subpopulations using a reagent loading device comprising a plurality of protrusions, and wherein applying the plurality of secondary antibodies to the plurality of subpopulations comprises simultaneously applying the plurality of secondary antibodies to the plurality of subpopulations using a reagent loading device comprising a plurality of protrusions.

13. The method of claim 12, wherein the target agent is a drug, and wherein the plurality of test agents is a plurality of cell libraries.

14. The method of claim 13, wherein applying the plurality of cell libraries to the plurality of subpopulations comprises simultaneously applying one of the plurality of cell libraries to each of the plurality of wells using a reagent loading device comprising a plurality of protrusions.

15. The device of claim 1, wherein a separation well in the plurality of separation wells contains cells in a cell suspension.

16. The device of claim 1, wherein the substrate is coated with a protein, a hydrogel, a polymer, a chemical compound, a fixed cell, or a micro-organism.

17. The device of claim 2, wherein the boundary wall comprises a substrate holder lock and a separation well lock, wherein the removable separation well structure comprises a separation well clip, wherein the separation well lock interfaces with the separation well clip;

and wherein the substrate holder is configured to couple the substrate to the boundary wall to form a holding cavity when coupled, wherein the substrate holder comprises a boundary wall clip configured to couple the substrate holder to the boundary wall, wherein the substrate holder lock interfaces with the boundary wall clip of the substrate holder, and wherein the removable separation well structure is coupled within the holding cavity.

18. The device of claim 17, further comprising a concentrating well structure located between the substrate and the removable separation well structure.

* * * * *